United States Patent
Waldor et al.

(10) Patent No.: US 11,484,585 B2
(45) Date of Patent: Nov. 1, 2022

(54) LIVE ATTENUATED CHOLERA VACCINE WITH PROBIOTIC PROPERTIES

(71) Applicant: The Brigham and Women's Hospital, Inc., Boston, MA (US)

(72) Inventors: Matthew K. Waldor, Newton, MA (US); Troy Hubbard, Boston, MA (US); Gabriel Billings, Somerville, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/629,898

(22) PCT Filed: Jul. 12, 2018

(86) PCT No.: PCT/US2018/041846
§ 371 (c)(1),
(2) Date: Jan. 9, 2020

(87) PCT Pub. No.: WO2019/014462
PCT Pub. Date: Jan. 17, 2019

(65) Prior Publication Data
US 2020/0268868 A1    Aug. 27, 2020

Related U.S. Application Data

(60) Provisional application No. 62/680,286, filed on Jun. 4, 2018, provisional application No. 62/531,551, filed on Jul. 12, 2017.

(51) Int. Cl.
| | | |
|---|---|---|
| *A61K 39/106* | (2006.01) |
| *A01N 63/00* | (2020.01) |
| *A61K 48/00* | (2006.01) |
| *A61K 39/02* | (2006.01) |
| *A61P 1/12* | (2006.01) |
| *A61P 31/04* | (2006.01) |
| *C12N 9/22* | (2006.01) |
| *C12N 15/11* | (2006.01) |
| *C12N 1/20* | (2006.01) |
| *A61K 39/00* | (2006.01) |
| *C12R 1/63* | (2006.01) |

(52) U.S. Cl.
CPC .............. *A61K 39/107* (2013.01); *A61P 1/12* (2018.01); *A61P 31/04* (2018.01); *C12N 1/205* (2021.05); *C12N 9/22* (2013.01); *C12N 15/11* (2013.01); *A61K 2039/522* (2013.01); *C12N 2800/80* (2013.01); *C12R 2001/63* (2021.05)

(58) Field of Classification Search
CPC .................................................. A61K 39/107
See application file for complete search history.

(56) References Cited

U.S. PATENT DOCUMENTS

2015/0064138 A1 *   3/2015   Lu ..................... A61K 38/465
                                                         424/93.2

FOREIGN PATENT DOCUMENTS

| WO | WO01/68829 | * | 9/2001 |
| WO | WO 2001/068829 | | 9/2001 |
| WO | WO 2016/040030 | | 3/2016 |
| WO | WO 2016/113322 | | 7/2016 |
| WO | WO 2016/177682 | | 11/2016 |

OTHER PUBLICATIONS

Hoppner, Horm Re. 2002, 58 Suppl. 3:7-15 (Year: 2002).*
Lodish et al., Mol. Cell Biol., 3rd ed. Scientific American Books, NY, 1995 (Year: 1995).*
John et al., Infection and Immunity, 2000; 68(3): 1171-1175 (Year: 2000).*
EP Extended Search Report in European Appln. No. 18832883.0, dated Jun. 1, 2021, 13 pages.
Abel et al., "Analysis of bottlenecks in experimental models of infection," PLoS Pathogens, Jun. 2015, 11(6).
Abel et al., "Sequence tag-based analysis of microbial population dynamics," Nature Methods, Mar. 2015, 12(3):223-6.
Aktar et al., "O-specific polysaccharide-specific memory B cell responses in young children, older children, and adults infected with Vibrio cholerae O1 Ogawa in Bangladesh" Clinical and Vaccine Immunology, May 1, 2016. 23(5):427-35.
Ali et al., "Updated global burden of cholera in endemic countries," PLoS Neglected Tropical Diseases, Jun. 2015, 9(6).
Azman et al., "The impact of a one-dose versus two-dose oral cholera vaccine regimen in outbreak settings: a modeling study," PLoS Medicine, Aug. 25, 2015, 12(8).
Azman et al., "The incubation period of cholera: a systematic review," Journal of Infection, May 1, 2013, 66(5):432-8.
Balakrishnan, "Cholera in Yemen," The Lancet Infectious Diseases, Jul. 2017, 17(7):700.
Bashir et al., "A hybrid approach for the automated finishing of bacterial genomes," Nature Biotechnology. Jul. 2012, 30(7):701.
Böhles et al., "Vaccines against human diarrheal pathogens: current status and perspectives," Human Vaccines & Immunotherapeutics, Jun. 4, 2014, 10(6):1522-35.
Butterton et al., "Heterologous antigen expression in Vibrio cholerae vector strains," Infection and Immunity, Jul. 1, 1995, 63(7):2689-96.
Calain et al., "Can oral cholera vaccination play a role in controlling a cholera outbreak?," Vaccine. Jun. 23, 2004, 22(19):2444-51.
Chao et al., "The design and analysis of transposon insertion sequencing experiments," Nature Reviews Microbiology, Feb. 2016, 14(2):119.

(Continued)

*Primary Examiner* — Gary B Nickol
*Assistant Examiner* — Lakia J Jackson-Tongue
(74) *Attorney, Agent, or Firm* — Fish & Richardson P.C.

(57) ABSTRACT

Provided herein are genetically engineered *Vibrio cholerae* bacterial strains, compositions including the bacterial strains, and methods of using the same for the prevention of *Vibrio cholerae* infection in a subject.

20 Claims, 14 Drawing Sheets

Figure 1:
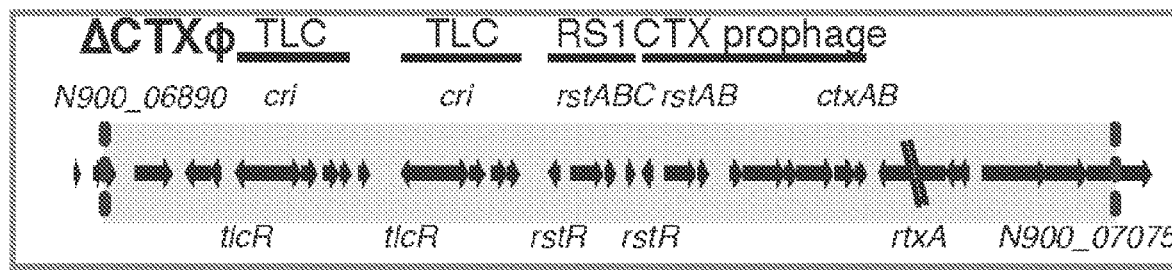

Specification includes a Sequence Listing.

(56) References Cited

OTHER PUBLICATIONS

Chen et al., "Single-dose live oral cholera vaccine CVD 103-HgR protects against human experimental infection with Vibrio cholerae O1 El Tor," Clinical Infectious Diseases, Jun. 1, 2016, 62(11):1329-35.
Chiang et al., "Construction of a mariner-based transposon for epitope-tagging and genomic targeting," Gene, Aug. 21, 2002, 296(1-2):179-85.
Chin et al., "The origin of the Haitian cholera outbreak strain," New England Journal of Medicine, Jan. 6, 2011, 364(1):33-42.
Clements et al., "Cholera," The Lancet, Mar. 13, 2017, 390, 1539-49.
Cohen et al., "Randomized, controlled human challenge study of the safety, immunogenicity, and protective efficacy of a single dose of Peru-15, a live attenuated oral cholera vaccine," Infection and Immunity, Apr. 1, 2002, 70(4):1965-70.
Duan et al., "Engineered bacterial communication prevents Vibrio cholerae virulence in an infant mouse model," Proceedings of the National Academy of Sciences, Jun. 22, 2010, 107(25):11260-4.
Farmer et al., "Meeting cholera's challenge to Haiti and the world: a joint statement on cholera prevention and care," PLoS Neglected Tropical Diseases, May 2011, 5(5), 13 pages.
Ferrieres et al., "Silent mischief: bacteriophage Mu insertions contaminate products of *Escherichia coli* random mutagenesis performed using suicidal transposon delivery plasmids mobilized by broad-host-range RP4 conjugative machinery," Journal of Bacteriology, Dec. 15, 2010, 192(24):6418-27.
Fullner et al., "The contribution of accessory toxins of Vibrio cholerae O1 El Tor to the proinflammatory response in a murine pulmonary cholera model." The Journal of Experimental Medicine, Jun. 3, 2002, 195(11):1455-62.
Gavin et al., "MARTX toxins as effector delivery platforms," Pathogens and Disease, Dec. 1, 2015, 73(9).
GenBank: CP006947.1. "Vibrio cholerae 01 str. KW3 chromosome I, complete sequence," updated Oct. 16, 2015, 2 pages.
Hill et al., "The International Scientific Association for Probiotics and Prebiotics consensus statement on the scope and appropriate use of the term probiotic," Nature Reviews Gastroenterology & Hepatology, Aug. 2014, 11(8):506-14.
Hsiao et al., "Members of the human gut microbiota involved in recovery from Vibrio cholerae infection," Nature, Nov. 2014, 515(7527):423-6.
Jackson et al., "Seroepidemiologic survey of epidemic cholera in Haiti to assess spectrum of illness and risk factors for severe disease," The American Journal of Tropical Medicine and Hygiene, Oct. 9, 2013, 89(4):654-64.
John et al., "In Vitro and In Vivo Analyses of Constitutive and In Vivo-Induced Promoters in Attenuated Vaccine and Vector Strains of Vibrio cholerae," Infection and Immunity, Mar. 1, 2000, 68(3):1171-5.
Kabir, "Critical analysis of compositions and protective efficacies of oral killed cholera vaccines." Clin. Vaccine Immunol. Sep. 1, 2014, 21(9):1195-205.
Kamp et al., "Gene fitness landscapes of Vibrio cholerae at important, stages of its life cycle," PLoS Pathogens, Dec. 2013, 9(12).
Kamruzzaman et al., "RS1 satellite phage promotes diversity of toxigenic Vibrio cholerae by driving CTX prophage loss and elimination of lysogenic immunity." Infection and Immunity, Sep. 1, 2014, 82(9):3636-43.
Kauffman et al., "Single-cell analysis of the plasmablast response to Vibrio cholerae demonstrates expansion of cross-reactive memory B cell," Mbio, Dec. 30, 2016, 7(6):e02021-16.
Kenner et al., "Peru-15, an improved live attenuated oral vaccine candidate for Vibrio cholerae O1." Journal of Infectious Diseases, Oct. 1, 1995, 172(4):1126-9.
Kim et al., "CTX prophages in Vibrio cholerae O1 strains." Journal of Microbiological Biotechnology, Jun. 2014, 24(6):725-31.
Lazar et al., "ToxR-independent expression of cholera toxin from the replicative form of CTXΦ," Infection and Immunity, Jan. 1, 1998, 66(1):394-7.
Luquero et al., "Use of Vibrio cholerae vaccine in an outbreak in Guinea," New England Journal of Medicine, May 29, 2014, 370(22):2111-20.
Martinez et al., "CTXφ replication depends on the histone-like HU protein and the UvrD helicase," PLoS Genetics, May 2015, 11(5).
Matias et al., "Antibody secreting cell responses following vaccination with bivalent oral cholera vaccine among haitian adults," PLoS Neglected Tropical Diseases, Jun. 2016, 10(6).
McLeod et al., "CTXφ and Vibrio cholerae: exploring a newly recognized type of phage-host cell relationship," Molecular Microbiology, Jul. 2005, 57(2):347-56.
Millet et al., "Insights into Vibrio cholerae intestinal colonization from monitoring fluorescently labeled bacteria," PLoS Pathogens, Oct. 2014, 10(10).
Olivier et al., Successful small intestine colonization of adult mice by Vibrio cholerae requires ketamine anesthesia and accessory toxins, PloS One, Oct. 2009. 4(10).
PCT International Preliminary Report on Patentability in International Appln. No. PCT/US18/41846, dated Jan. 14, 2020, 11 pages.
PCT International Search Report and Written Opinion in International Appln. No. PCT/US18/41846, dated Dec. 4, 2018, 16 pages.
Pritchard et al., "Artist: high-resolution genome-wide assessment of fitness using transposon-insertion sequencing," PLoS Genetics. Nov. 2014, 10(11).
Qadri et al., "Feasibility and effectiveness of oral cholera vaccine in an urban endemic setting in Bangladesh: a cluster randomised open-label trial," The Lancet, Oct. 3, 2015, 386(10001):1362-71.
Qadri et al.. "Peru-15, a live attenuated oral cholera vaccine, is safe and immunogenic in Bangladeshi toddlers and infants," Vaccine, Jan. 4, 2007, 25(2):231-8.
Reyburn et al., "The case for reactive mass oral cholera vaccinations," PLoS Neglected Tropical Diseases, Jan. 2011, 5(1).
Ritchie et al., "Back to the future: studying cholera pathogenesis using infant rabbits," Mbio. May 18, 2010, 1(1):e00047-10.
Rollenhagen et al., "Transcutaneous immunization with a synthetic hexasaccharide-protein conjugate induces anti-Vibrio cholerae lipopolysaccharide responses in mice," Vaccine, Aug. 6, 2009, 27(36):4917-22.
Rui et al., "Reactogenicity of live-attenuated Vibrio cholerae vaccines is dependent on flagellins," Proceedings of the National Academy of Sciences, Mar. 2, 2010, 107(9):4359-64.
Rutherford et al., "Bacterial quorum sensing: its role in virulence and possibilities for its control," Cold Spring Harbor Perspectives in Medicine, Nov. 1, 2012, 2(11):a012427.
Satchell, "Multifunctional-autoprocessing repeats-in-toxin (MARTX) Toxins of Vibrios," Microbiology Spectrum. Jun. 2015, 3(3).
Tarique et al., "Transcutaneous immunization with a Vibrio cholerae O1 Ogawa synthetic hexasaccharide conjugate following oral whole-cell cholera vaccination boosts vibriocidal responses and induces protective immunity in mice." Clin. Vaccine Immunol, Apr. 1, 2012, 19(4):594-602.
Thompson et al., "Use of recA as an alternative phylogenetic marker in the family Vibrionaceae," International Journal of Systematic and Evolutionary Microbiology, May 1, 2004, 54(3):919-24.
Waldor et al., "Lysogenic conversion by a filamentous phage encoding cholera toxin," Science, Jun. 28, 1996, 272(5270):1910-4.
Weil et al., "Clinical outcomes in household contacts of patients with cholera in Bangladesh," Clinical Infectious Diseases, Nov. 15, 2009, 49(10):1473-9.
Zhu et al., "Quorum-sensing regulators control virulence gene expression in Vibrio cholerae." Proceedings of the National Academy of Sciences. Mar. 5, 2002, 99(5):3129-34.
Bikard et al., "Exploiting CRISPR-Cas nuclease to produce sequence-specific antimicrobials," Nature Biotechnology, No. 2014, 32(11):1146-50.
Davis et al., "Filamentous phages linked to virulence of Vibrio cholerae," Current Opinion in Microbiology, Feb. 1, 2003, 6(1):35-42.
EP European Search Report in European Appln. No. 18832833.0, dated Mar. 1, 2021, 8 pages.

(56) References Cited

OTHER PUBLICATIONS

JP Japanese Office Action in Japanese Appln. No. 2020-501328, dated Jul. 26, 2022, 10 pages (with English translation).
Mahmoudi et al., "Malaria vaccine development: The need for novel approaches: A review article," Iranian Journal of Parasitology, Jan. 2018, 13(1).1.

* cited by examiner

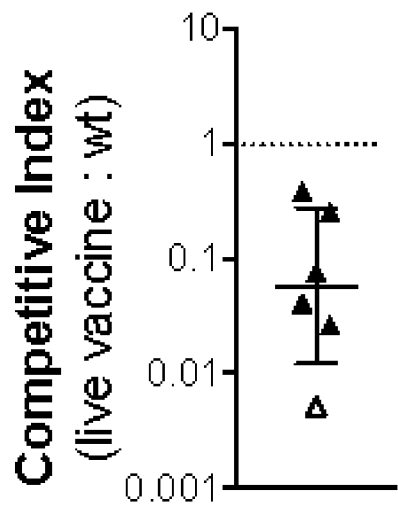
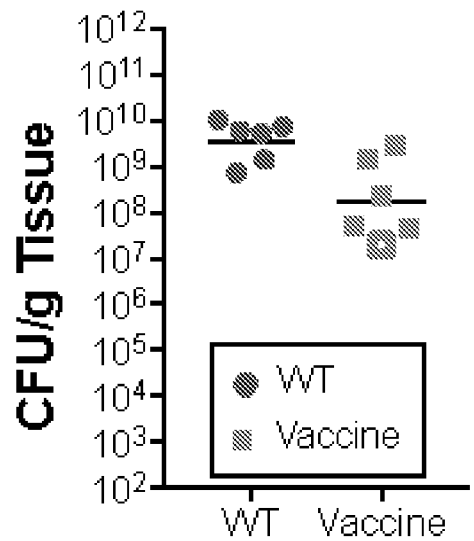
FIG. 4D  FIG. 4E
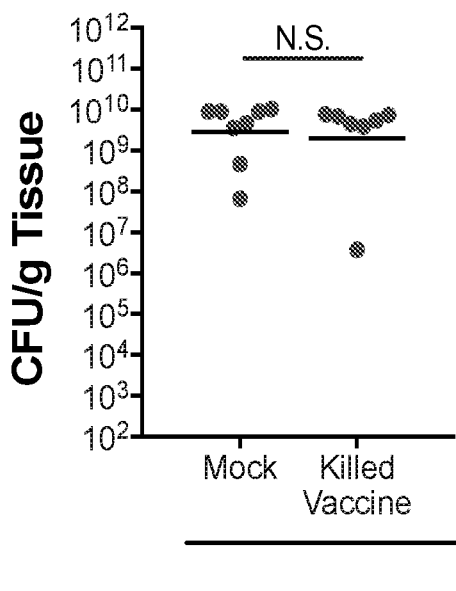
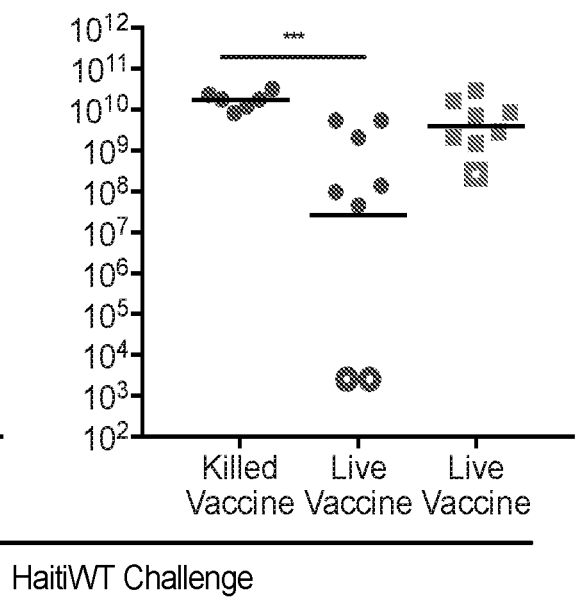
FIG. 5A  FIG. 5B

Sequential Inoculation: killed vaccine / live vaccine followed by wild type

Single Inoculation: transposon mutant library

Sequential Inoculation: live vaccine followed by transposon mutant library

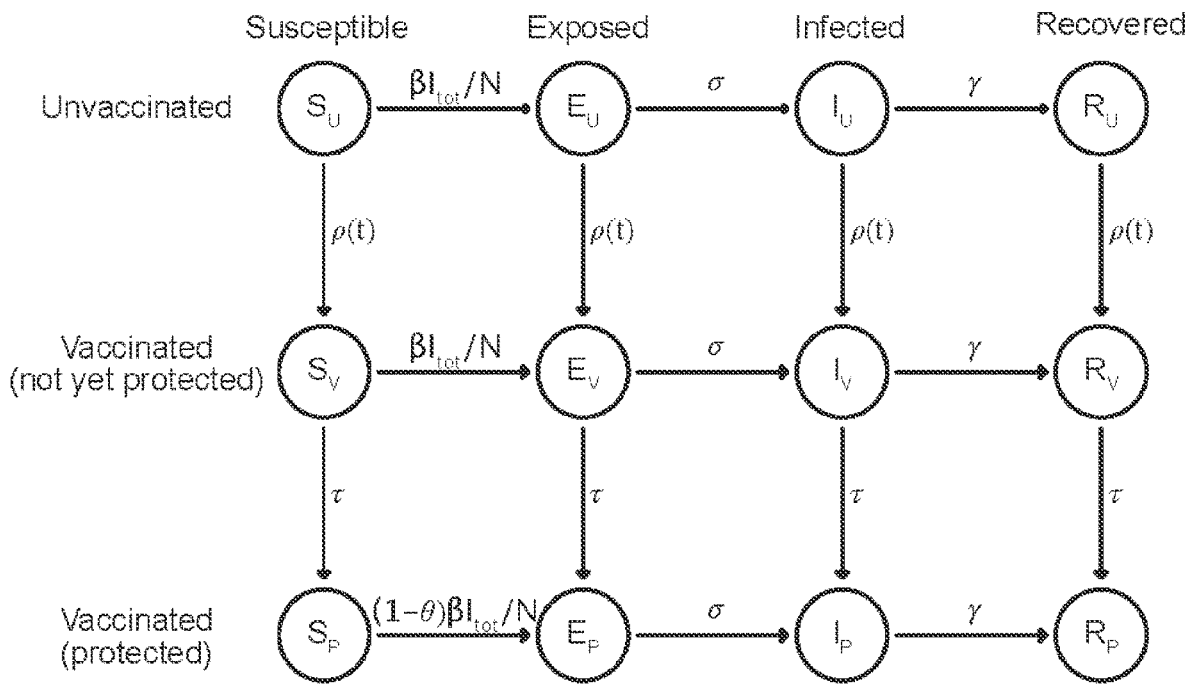

FIG. 10A

| Parameter description | Symbol | Value |
|---|---|---|
| Transmission parameter | β | 0.5-2.5 /day |
| Mean incubation period | 1/σ | 1.4 days |
| Mean period of infectiousness | 1/γ | 2 days |
| Time-dependent rate of vaccination | ρ(t) | See text |
| Mean time to protection | 1/τ | 1 day (fast vaccine) or 10 days (slow vaccine) |
| Vaccine efficacy | θ | 0.7 |
| Population size | N | 100000 |
| Fraction of population vaccinated | | 0.7 |
| Duration of vaccination campaign | | 1-21 days |
| Vaccination campaign triggering threshold (number of symptomatic cases) | | 100-10,000 |
| Fraction of infections that are symptomatic | | 0.25 |

FIG. 10B

LIVE ATTENUATED CHOLERA VACCINE WITH PROBIOTIC PROPERTIES

CROSS REFERENCE TO RELATED APPLICATIONS

This application is a national stage application of PCT/US2018/041846, filed Jul. 12, 2018, which claims the benefit of priority of U.S. Application No. 62/531,551, filed Jul. 12, 2017; and U.S. Application No. 62/680,286, filed Jun. 4, 2018. The content of each of the foregoing applications is hereby incorporated by reference in its entirety.

FEDERALLY SPONSORED RESEARCH OR DEVELOPMENT

This invention was made with Government support under Grant Nos. AI042347 and AI-120665, awarded by the National Institutes of Health. The Government has certain rights in the invention.

TECHNICAL FIELD

Described herein are genetically engineered *Vibrio cholerae* bacteria, pharmaceutical compositions including the bacteria, and methods of using the bacteria and/or a pharmaceutical composition including the bacteria to protect against disease caused by virulent strains of *Vibrio cholerae* through a combination of rapid probiotic protection and eliciting an adaptive immune response.

SEQUENCE LISTING

The instant application contains a Sequence Listing which has been filed electronically in ASCII format and is hereby incorporated by reference in its entirety. Said ASCII copy, created on Jul. 10, 2018, is named 29618-0175WO1_SL.txt and is 5.03 megabytes in size.

BACKGROUND

Cholera is a diarrheal disease caused by an infection with the Gram-negative bacterium *Vibrio cholerae*. The disease can be a rapidly fatal, and outbreaks often spread explosively. Efforts to fight the disease include oral rehydration and antibiotic therapy. However, the disease is a major public health hazard in developing and destabilized countries (see, e.g., Bohles et al. (2014) *Hum. Vaccin. Immunother.* 10(6): 1522-35). Vaccination campaigns deploying vaccines comprising killed *Vibrio cholerae* bacterial strains are currently underway. However, the utility of these vaccines for curtailing the spread of an ongoing epidemic (so-called 'reactive vaccination') depends on the time required for vaccinated subjects to become resistant to cholera. The protective immune responses elicited by current vaccines typically take days or weeks to manifest and often require multiple vaccine doses. Thus, there is a need for vaccines that can induce rapid protection against *Vibrio cholerae* after a single dose.

SUMMARY

Described herein are attenuated *V. cholerae* bacterial strains that act, in an unprecedented manner, both as probiotic agents, to rapidly protect against cholera, and as traditional vaccines, to elicit the long-lived protective immunity to cholera observed of existing cholera vaccines. The attenuated *V. cholerae* bacterial strains described herein, as HaitiV, are derived from a recent clinical isolate, include multiple genetic modifications, and exhibit robust, multi-day occupancy of the intestine that is suggestive/predictive of their potential to engender long-lived immunity to cholera in humans. Surprisingly, a single dose of the attenuated bacterial strains is capable of conferring protection against a lethal challenge within 24 hours of HaitiV-administration in the infant rabbit model of cholera. The observation of such rapid protection in a neonatal model of infection is inconsistent with the protective immunity elicited by traditional vaccines. Instead, the ability of live HaitiV to rapidly mediate colonization resistance and disease protection against multiple challenge strains indicates that HaitiV, unlike existing vaccines, confers probiotic protection against cholera. Moreover, mathematical modeling indicates that the unprecedented speed of HaitiV-mediated protection could dramatically improve the public health impact of reactive vaccination. Thus, administration of the bacterial strains described herein can be used to reduce the risk of cholera infection, in particular during an ongoing epidemic, by engendering both rapid and long-lived protection.

Moreover, an attenuated *V. cholerae* bacterial strain may be induced to revert into a virulent strain by reacquiring virulence genes, and methods of preventing and/or mitigating the possibility of HaitiV's reversion to toxigenicity are also provided. Of particular concern are the genes encoding cholera toxin, the pathogen's principal diarrheagenic factor, which are deleted from live cholera vaccines. Any means of horizontal gene transfer, including re-infection by the cholera toxin encoding bacteriophage (CTXΦ) or natural transformation, may be sufficient to induce vaccine reversion. Applicants have developed attenuated *V. cholerae* bacterial strains modified to include RNA-guided endonuclease systems capable of specifically targeting the ctxA gene, which encodes the active subunit of cholera toxin. This strategy provides a biosafety mechanism to prevent *V. cholerae* bacteria from reacquiring ctxA, by any means, including infection with the CTXΦ prophage. Furthermore, this strategy can be generalized to other attenuated vaccine strains (e.g., Vaxchora and Peru-15) by engineering the strains to produce anti-virulence factor CRISPR systems from plasmid-encoded or chromosomally-integrated constructs.

In one aspect, the disclosure provides a genetically engineered *Vibrio cholerae* bacterium having a deletion in a nucleic acid sequence encoding a cholera toxin subunit A; a heterologous nucleic acid sequence encoding a Cas9 nuclease molecule; and a heterologous nucleic acid sequence encoding a guide RNA (gRNA), wherein the gRNA includes a targeting domain which is complementary with a target nucleic acid sequence of ctxA.

In some embodiments, a genetically engineered *V. cholerae* bacterium provided herein has a deletion in the nucleic acid sequence encoding the cholera toxin subunit A that is located in a ctxA gene that was integrated into the genome of the bacterium.

In some embodiments, a genetically engineered *V. cholerae* bacterium provided herein has a deletion in a nucleic acid sequence of the core region of a CTXΦ genome that was integrated into the genome of the bacterium.

In some embodiments, a genetically engineered *V. cholerae* bacterium provided herein has a deletion in a nucleic acid sequence of the RS2 region of a CTXΦ genome that was integrated into the genome of the bacterium.

In some embodiments, a genetically engineered *V. cholerae* bacterium provided herein has a complete deletion of a CTXΦ genome that was integrated into the genome of the bacterium.

In another aspect, the disclosure provides a genetically engineered *Vibrio cholerae* bacterium having a heterologous nucleic acid sequence encoding a Cas9 nuclease molecule; and a heterologous nucleic acid sequence encoding a guide RNA (gRNA), wherein the gRNA includes a targeting domain which is complementary with a target nucleic acid sequence of CTXΦ.

In some embodiments, target nucleic acid sequence of the CTXΦ genome is located in a gene selected from the group consisting of rstR, rstA, rstB, psh, cep, orfU, ace, zot, ctxA and ctxB. In some embodiments, the target nucleic acid sequence of the CTXΦ genome is located in a ctxA gene. In some embodiments, the gRNA comprises or consists of the nucleic acid sequence 5'-cctgatgaaataaagcagtcgttttagagctagaaatagc aagttaaaataaggctagtccgttatcaacttgaaaaagtggcaccgagtcggtgc-3' (SEQ ID NO: 3).

In some embodiments, a genetically engineered *V. cholerae* bacterium provided herein has not previously had a copy of a CTXΦ genome integrated into the bacterial genome.

In some embodiments, a genetically engineered *V. cholerae* bacterium provided herein has a deletion in a nucleic acid sequence encoding a multifunctional-autoprocessing repeats-in-toxin (MARTX) toxin. In some embodiments, the nucleic acid sequence encoding the MARTX toxin is selected from the group consisting of rtxA, rtxB, rtxC, rtxD, and rtxE.

In some embodiments, a genetically engineered *V. cholerae* bacterium provided herein has a deletion in a nucleic acid sequence encoding a DNA-binding protein HU-beta. In some embodiments, the nucleic acid sequence encoding the DNA-binding protein HU-beta is a hupB gene.

In some embodiments, a genetically engineered *V. cholerae* bacterium provided herein has a deletion in a nucleic acid encoding a flagellin. In some embodiments, the nucleic acid sequence encoding a flagellin is selected from the group consisting of flaA, flaB, flaC, flaD, and FlaE.

In some embodiments, a genetically engineered *V. cholerae* bacterium provided herein includes a heterologous nucleic acid, wherein the heterologous nucleic acid includes a gene encoding cholera toxin subunit B that is operably-linked to a promoter. In some embodiments, the gene encoding cholera toxin subunit B is a ctxB gene. In some embodiments, the promoter is an inducible promoter. In some embodiments, the promoter is a $P_{htpg}$ promoter. In some embodiments, the promoter is a constitutive promoter.

In some embodiments, a genetically engineered *V. cholerae* bacterium provided herein has a deletion in a nucleic acid sequence encoding a RecA protein. In some embodiments, the nucleic acid sequence encoding the RecA protein is a recA gene.

In another aspect, the disclosure provides a genetically engineered *Vibrio cholerae* bacterium having a deletion in one or more nucleic acid sequences encoding a MARTX toxin selected from the group consisting of rtxA, rtxB, rtxC, rtxD, rtxE and rtxH; a deletion in one or more flagellin genes selected from the group consisting of flaA, flaB, flaC, flaD, and FlaE; a deletion in a recA gene; and a heterologous nucleic acid, wherein the heterologous nucleic acid includes a ctxB gene operably linked to a promoter (e.g., a constitutive promoter or an inducible promoter). In some embodiments, the bacterium includes a complete deletion of a CTXΦ genome that was integrated into the genome of the bacterium. In some embodiments, the bacterium has not previously had a copy of a CTXΦ prophage genome integrated into the bacterial genome.

In some embodiments, a genetically engineered *V. cholerae* bacterium provided herein includes a heterologous nucleic acid sequence encoding a Cas9 nuclease molecule; and a heterologous nucleic acid sequence encoding a guide RNA (gRNA), wherein the gRNA includes a targeting domain which is complementary with a target nucleic acid sequence of ctxA. In some embodiments, the target nucleic acid sequence of CTXΦ is located in a ctxA gene. In some embodiments, the gRNA comprises or consists of the nucleic acid sequence 5'-cctgatgaaataaagcagtcgttttagagctagaaatagcaagttaaaataaggct agtccgttatcaacttgaaaaagtggcaccgagtcggtgc-3' (SEQ ID NO: 3).

In some embodiments, a genetically engineered *V. cholerae* bacterium provided herein has a deletion in one or more of: a nucleic acid sequence encoding a product that confers resistance to trimethoprim, a nucleic acid sequence encoding a product that confers resistance to sulfamethoxazole, a nucleic acid sequence encoding a product that confers resistance to streptomycin, and a nucleic acid sequence encoding a product that confers resistance to chloramphenicol. In some embodiments, the gene encoding a product that confers resistance to trimethoprim is dfrA. In some embodiments, the gene encoding a product that confers resistance to sulfamethoxazole is sul2. In some embodiments, the gene encoding a product that confers resistance to streptomycin is strAB. In some embodiments, the gene encoding a product that confers resistance to chloramphenicol is floR.

In some embodiments, a genetically engineered *V. cholerae* bacterium provided herein is derived from a parental strain belonging to the El Tor biotype.

In some embodiments, a genetically engineered *V. cholerae* bacterium provided herein is derived from a Haiti parental strain.

In some embodiments, a genetically engineered *V. cholerae* bacterium provided herein includes a first bacterial chromosome including or consisting of the nucleic acid sequence of SEQ ID NO: 7. In some embodiments, a genetically engineered *V. cholerae* bacterium provided herein includes a second bacterial chromosome including or consisting of the nucleic acid sequence of SEQ ID NO: 51.

In one aspect, the disclosure provides a genetically engineered *Vibrio cholerae* bacterium, wherein the bacterium has mutations in the same genes, relative to its parental strain (e.g., a virulent parental strain), as the strain having ATCC deposit number PTA-125138.

In another aspect, the disclosure provides a genetically engineered *Vibrio cholerae* bacterium, wherein the bacterium is a *V. cholerae* strain having ATCC deposit number PTA-125138.

The disclosure also provides pharmaceutical compositions including a genetically engineered *Vibrio cholerae* bacterium provided herein and a pharmaceutically acceptable excipient.

The disclosure further provides methods of inducing a protective response in a subject against a virulent strain of *Vibrio cholerae*, including administering to the subject a genetically engineered *Vibrio cholerae* bacterium provided herein, or a pharmaceutical composition including the bacterium, thereby inducing the protective response against the virulent strain of *Vibrio cholerae* in the subject (e.g., a human subject). In some embodiments, the protective response is induced within 24 hours of administering the genetically engineered *Vibrio cholerae* bacterium or of the pharmaceutical composition to the subject.

Figure 5C:
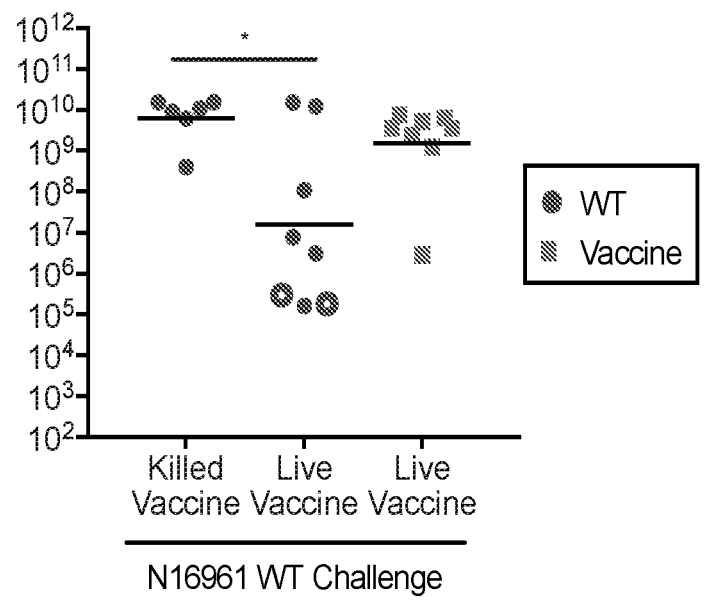
Figure 5D:
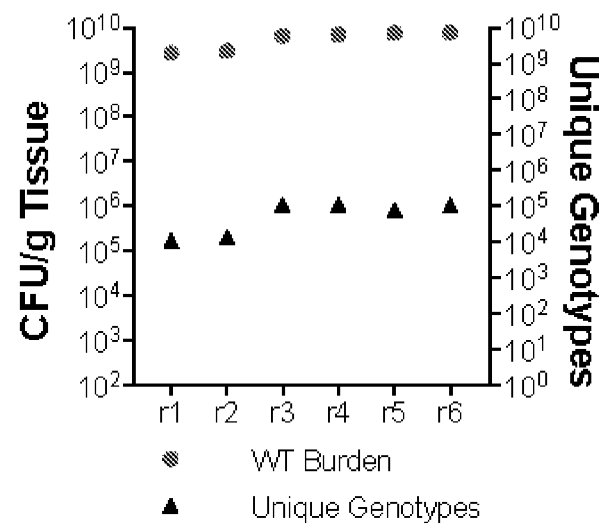
Figure 5E:
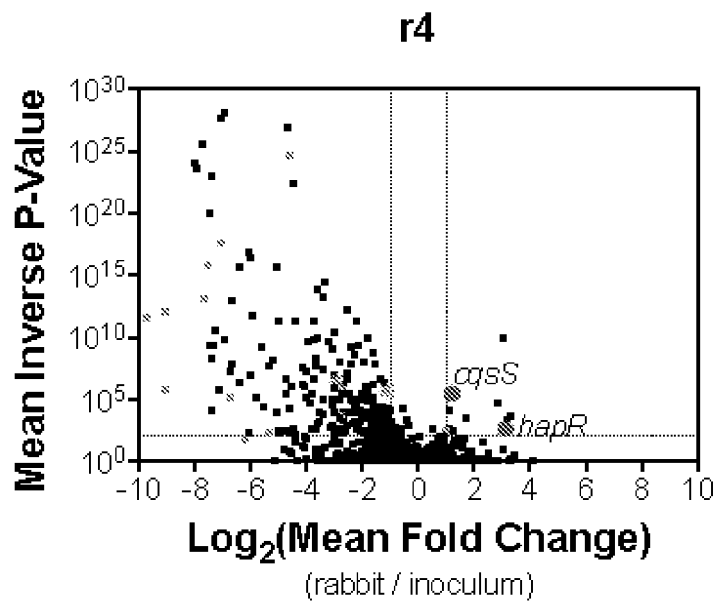
Figure 5F:
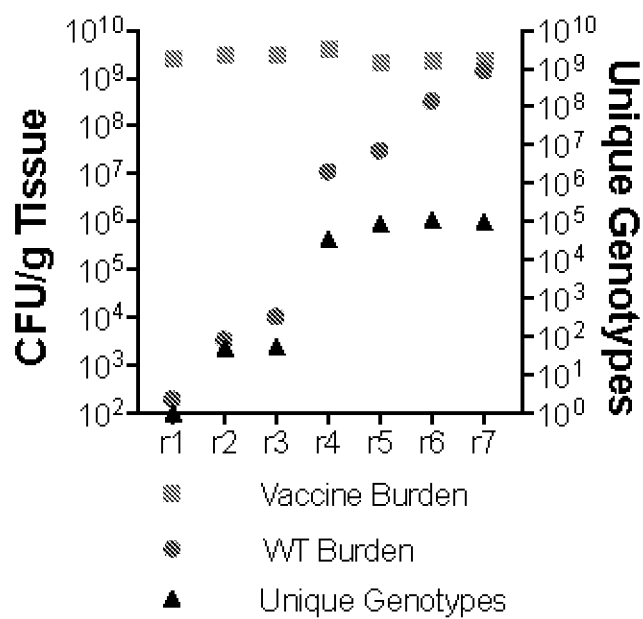
Figure 5G:
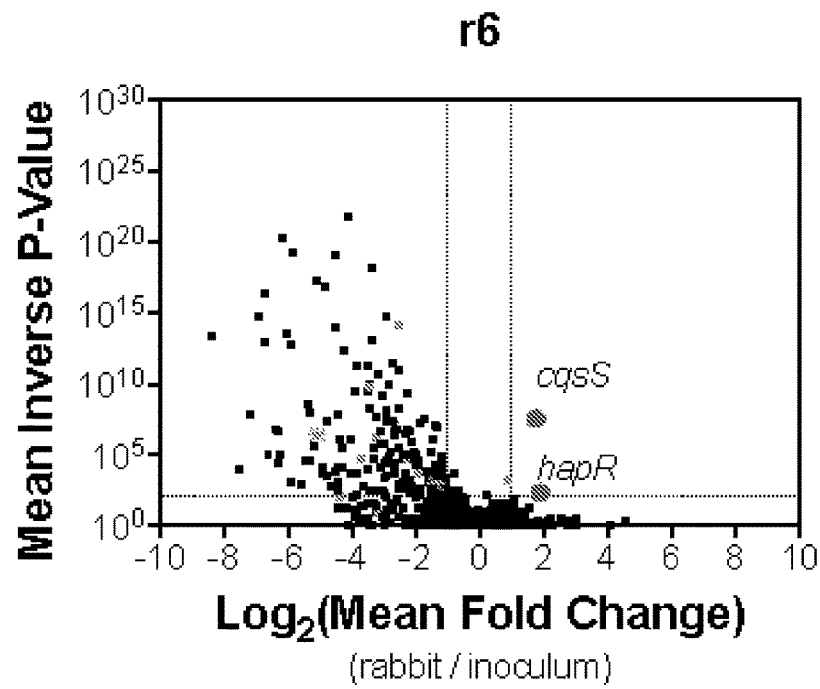

The disclosure also provides a genetically engineered *Vibrio cholerae* bacterium provided herein, for use in a method of inducing a protective response in a subject against a virulent strain of *Vibrio cholera*.

Also provided is a genetically engineered *Vibrio cholerae* bacterium provided herein, for use in a method of treating a subject who has a virulent strain of *Vibrio cholerae*.

In another aspect, the disclosure also provides a genetically engineered bacterium having a deletion of at least one virulence gene; a heterologous nucleic acid encoding a Cas9 nuclease molecule; and one or more heterologous nucleic acids encoding guide RNAs (gRNAs), wherein the gRNAs include a targeting domain that is complementary with a target nucleic acid sequence of the deleted virulence gene; wherein the Cas9 nuclease molecule is capable of binding to the gRNAs thereby forming a complex, and wherein the complex is capable of targeting and cleaving a nucleic acid sequence of the deleted virulence gene. In some embodiments, the bacterium is of a species selected from the group consisting of *Vibrio cholerae, Salmonella enterica, Shigella flexneri, Shigella sonnei, Shigella dysenteriae, Bordetella pertussis*, and *Clostridioides difficile*. In some embodiments, the virulence gene is selected from the group consisting of ctxA, aroA, aroQ, aroC, aroD, htrA, ssaV, cya, crp, phoP, phoQ, guaB, guaA, clpX, clpP, set, sen, virG/icsA, luc, aroA, msbB2, stxA, stxB, ampG, dnt, tcdA, and tcdB.

The disclosure also provides a pharmaceutical composition including a genetically engineered bacterium provided herein and a pharmaceutically acceptable excipient.

Also provided are methods of inducing a protective response in a subject against a virulent strain of bacterium described herein (e.g., *Vibrio cholerae, Salmonella enterica, Shigella flexneri, Shigella sonnei, Shigella dysenteriae, Bordetella pertussis*, and *Clostridioides difficile*), including administering to the subject a genetically engineered bacterium provided herein, or a pharmaceutical composition including the genetically engineered bacterium, thereby inducing the protective response against the virulent strain of bacterium in the subject (e.g., a human subject).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 depicts the deletion of the CTXΦ prophage and adjacent sequences, including the satellite prophages, TLC and RS1, and MARTX toxin genes (shadowed area is the deleted region).

FIG. 2 depicts the deletions in genes conferring resistance to trimethoprim (dfrA), sulfamethoxazole (sul2) streptomycin (strAB) and chloramphenicol (floR).

FIGS. 3A, 3B and 3C depict an anti-ctxA CRISPR system which provides immunity to CTXΦ infection. FIG. 3A depicts a *Streptococcus pyogenes* Cas9 along with sequence encoding a guide RNA targeting ctxA, integrated into the HaitiV lacZ locus. FIG. 3B is a schematic showing targeting of the CTXΦ genome by the anti-ctxA Cas9-sgRNA complex. FIG. 3C is a bar graph showing the transduction efficiency in HaitiV with/without the CRISPR system (CRISPR+/−) that were infected with either CTXΦ-IGKn (Target+; intergenic $Kan^R$ cassette, intact ctxA) or CTX-KnΦ (Target-; ctxA replaced by $Kan^R$ cassette), and the number of transductants was monitored. No detectable $Kan^R$ transductants shown as "*".

FIGS. 4A, 4B, 4C, 4D, and 4E show that HaitiV colonizes the infant rabbit intestine without causing cholera-like illness. FIG. 4A is a bar graph depicting the fluid accumulation ratios after littermates were inoculated with either wild type ("WT"; n=11) or HaitiV ("Vaccine"; n=10). Plots show mean and standard deviation derived from 2 litters. **$P<0.001$, unpaired t-test. FIG. 4B is a line graph showing the successive daily body weights of animals inoculated with approximately $10^9$ CFU HaitiV (n=10). FIG. 4C is a dot plot showing the WT CFU (circles) or HaitiV CFU (squares) recovered from rabbit distal small intestines (dSI) at Day 1 or 4 post-inoculation (2 litters/group). Lines indicate geometric means. Hollow points indicate limit of detection when no CFU were recovered. NS: $P>0.05$, Kruskall-Wallis test followed by Dunn's multiple comparisons test. FIG. 4D depicts the competitive indices (CI) of dSI bacteria 1 day post-inoculation with a 1:1 mixture of WT and HaitiV. Hollow points show the limit of detection when no vaccine CFU were recovered; lines and bars indicate geometric means and geometric standard deviation of CIs across 2 litters, (n=6). FIG. 4**E is a dot plot showing the WT CFU (circles) and HaitiV CFU (squares) recovered from co-inoculated animals; lines indicate geometric means.

FIGS. 5A, 5B, 5C, 5D, 5E, 5F, and 5G show that HaitiV mediates colonization resistance associated with variably-sized infection bottlenecks. FIG. 5A shows WT CFU (circles) recovered from dSI of animals 18 hours after inoculation with WT. Littermates were pretreated with sodium bicarbonate buffer (mock, n=8) or formalin-killed HaitiV (killed vaccine, n=7) 24 hours prior to WT challenge; geometric means of each group across 3 litters are shown. NS: $P>0.05$, Mann-Whitney test. FIG. 5B shows WT CFU (circles) or HaitiV CFU (squares) recovered from the dSI of animals 18 hours post-challenge with WT. Animals were pretreated with killed (n=6) or live (n=8) vaccine 24 hours prior to challenge. Hollow points indicate limit of detection when no CFU were recovered, and lines indicate the geometric mean of each group across 2 litters. *$P<0.001$, Mann-Whitney test. FIG. 5**C shows WT CFU (circles) or HaitiV CFU (squares) recovered from the dSI of animals 18 hours post-challenge with WT, of the N16961 strain. Animals were pretreated with killed (n=6) or live (n=8) vaccine 24 hours prior to challenge. Hollow points indicate limit of detection when no CFU were recovered, and lines indicate the geometric mean of each group across 2 litters. *$P<0.05$, Mann-Whitney test. FIG. 5D depicts the WT CFU (circles), and unique transposon mutants (triangles) recovered from the dSI of individual animals (rabbits r1 to r6) one day after inoculation of the transposon mutant library without pretreatment. FIG. 5F depicts the WT CFU (circles), HaitiV CFU (squares), and unique transposon mutants (triangles) recovered from the dSI of individual animals (rabbits r1 to r7) one day after inoculation of the transposon mutant library. Animals were pretreated with HaitiV 24 hours prior to challenge with the transposon mutant library. FIGS. 5E and 5G depict the results of Con-ARTIST (see Pritchard et al. (2014) *PLoS Genet.* 10: e1004782) analysis for single inoculation (rabbit r4; FIG. 5E) and sequential inoculation (rabbit r6; FIG. 5G) samples with the largest number of unique genotypes. The x-axis indicates the change in relative abundance of insertion mutants per gene in vivo, and the y-axis indicates the concordance of independent insertion mutants within each gene. Genes exhibiting a greater than 2-fold change ($Log_2$(mean fold change)<−1 or >1) across multiple mutants (mean inverse P-value>$10^2$) are considered depleted/enriched. Enriched mutants cqsS and hapR are indicated. Mutations in critical colonization factors, including toxin co-regulated pilus biogenesis (circles), and the associated transcriptional regulators toxR and toxS (asterisks), were depleted.

Figure 6A:
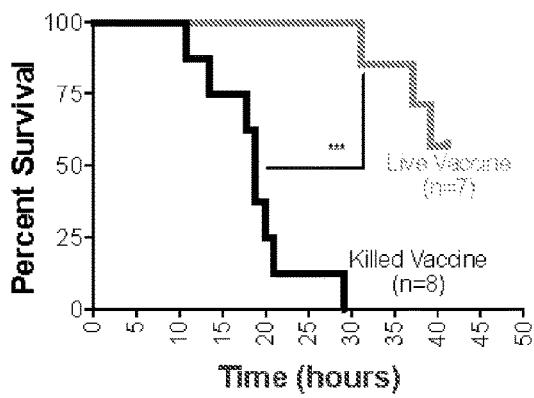
Figure 6B:
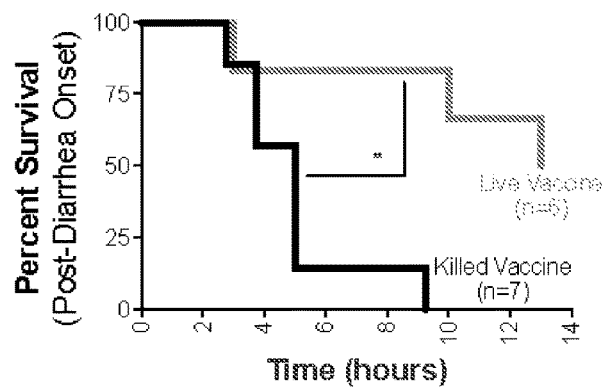
Figure 6C:
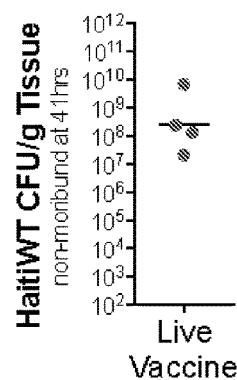
Figure 6D:
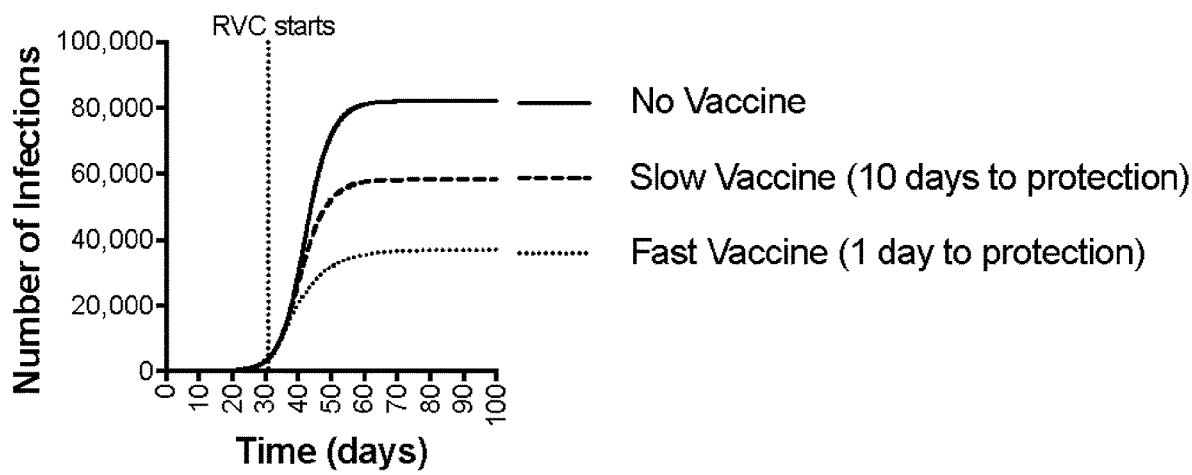

FIGS. 6A, 6B, 6C and 6D show that HaitiV colonization protects from disease following HaitiWT challenge, and modeling demonstrates the benefit of rapid protection during a cholera outbreak. FIG. 6A depicts survival curves tracking progression to moribund disease status in animals inoculated with WT at 0 hours after pretreatment (at t=−24 hours) with killed (black) or live vaccine (red). *P<0.001, Log-rank test. FIG. 6B depicts the disease progression from the onset of diarrhea to moribund status in animals (from FIG. 6A) that developed visible diarrhea. *P<0.001, Log-rank test. FIG. 6C depicts WT CFU (circles) recovered from dSI of animals (from FIG. 6A) that did not progress to moribund disease status. FIG. 6D depicts the effect of reactive vaccination on the number of cholera infections in a simulated outbreak ($R_0$=2.1) starting with a single infection in a population of 100,000 susceptible individuals where the reactive vaccination campaign (RVC) is triggered once the number of symptomatic individuals reaches 1000 (1% of the total population), indicated by the dashed line. The rollout of doses is modeled with a constant rate over 7 days until 70% of the population is vaccinated, as achieved by recent reactive vaccination campaigns. Modeling parameters are described in FIG. 10B FIG. 7 is a Western blot showing that HaitiV produces only the B subunit of cholera toxin. Cell-free supernatant from Haiti wild type ("Haiti WT") and HaitiV, as well as purified cholera toxin ("Purified CT"), was separated by polyacrylamide gel electrophoresis. Immunoblotting with polyclonal anti-CTX antibody revealed the presence of CT-B, but not CT-A, in the supernatant of HaitiV.

FIGS. 8A, 8B, 8C, and 8D show the results of Con-ARTIST analyses for single inoculation samples. The x-axes indicate the change in relative abundance of insertion mutants per gene in vivo, and the y-axes indicate the concordance of independent insertion mutants within each gene. Genes exhibiting a greater than 2-fold change (Log 2(mean fold change)<−1 or >1) across multiple mutants (mean inverse P-value>100) are considered depleted/enriched. cqsS and hapR are indicated. A subset of colonization factors, including toxin co-regulated pilus biogenesis components (circles) and the associated transcriptional regulators toxR and toxS (asterisks), are indicated also.

FIGS. 9A, 9B, 9C, and 9D show the results of Con-ARTIST analyses for sequential inoculation samples. The x-axes indicate the change in relative abundance of insertion mutants per gene in vivo, and the y-axes indicate the concordance of independent insertion mutants within each gene. Genes exhibiting a greater than 2-fold change (Log 2(mean fold change)<−1 or >1) across multiple mutants (mean inverse P-value>102) are considered depleted/enriched. cqsS and hapR are indicated. A subset of colonization factors, including toxin co-regulated pilus biogenesis components (circles) and the associated transcriptional regulators toxR and toxS (asterisks), are indicated also.

FIG. 10A depicts an overview of the SEIR cholera transmission model with delayed vaccine effect. Circles indicate the subpopulations of the model (Susceptible, Exposed, Infectious, Recovered, with subscripts U: unvaccinated, V: vaccinated, but not yet protected, and P: Protected), while arrows indicate transitions between sub-populations. FIG. 10B is a list of parameters used in modeling.

FIGS. 11A and 11B show the impact of transmission potential ($R_0$) and either rollout rate (FIG. 11A) or triggering threshold (FIG. 11B) of the vaccination campaign on the relative protection (fractional reduction in cases) of a fast-acting vaccine over a slow-acting vaccine.

FIGS. 12A, 12B, 12C, and 12D are graphs depicting the vibriocidal activity of sera from mice inoculated with HaitiV or CVD103-HgR*. FIG. 12A is a graph depicting the vibriocidal response of sera from C57BL/6 mice inoculated with HaitiV against a serotype Inaba *V. cholerae* strain. FIG. 12B is a graph depicting the vibriocidal response of sera from Swiss-Webster mice inoculated with either HaitiV (black circles) or CVD103-HgR* (empty squares and dashed lines) against a serotype Inaba *V. cholerae* strain. FIG. 12C is a graph depicting the vibriocidal response of sera from C57BL/6 mice inoculated with HaitiV against a serotype Ogawa *V. cholerae* strain. FIG. 12D is a graph depicting the vibriocidal response of sera from Swiss-Webster mice inoculated with either HaitiV (black circles) or CVD103-HgR* (empty squares and dashed lines) against a serotype Ogawa *V. cholerae* strain. Bold black dashes above the x-axis indicate time points at which animals were orogastrically inoculated with HaitiV or CVD103-HgR*. The dashed line along the y-axis indicates the assay limit of detection.

FIGS. 13A, 13B, 13C, and 13D are graphs depicting the IgA and IgG response against O-antigen-specific polysaccharide (OSP) from a serotype Ogawa *V. cholerae* strain over time in mice inoculated with HaitiV or CVD103-HgR*. FIG. 13A is a graph depicting the anti-OSP IgA response in C57BL/6 mice inoculated with HaitiV against OSP from a serotype Ogawa *V. cholerae* strain. FIG. 13B is a graph depicting the anti-OSP IgA response in Swiss-Webster mice inoculated with either HaitiV (black circles) or CVD103-HgR* (empty squares and dashed lines) against OSP from a serotype Ogawa *V. cholerae* strain. FIG. 13C is a graph depicting the anti-OSP IgG response in C57BL/6 mice inoculated with HaitiV against OSP from a serotype Ogawa *V. cholerae* strain. FIG. 13D is a graph depicting the anti-OSP IgG response in Swiss-Webster mice inoculated with either HaitiV (black circles) or CVD103-HgR* (empty squares and dashed lines) against OSP from a serotype Ogawa *V. cholerae* strain. Bold black dashes above the x-axis indicate time points at which animals were orogastrically inoculated with HaitiV or CVD103-HgR*.

FIGS. 14A, 14B, 14C, and 14D are graphs depicting the IgA and IgG response against O-antigen-specific polysaccharide (OSP) from a serotype Inaba *V. cholerae* strain over time in mice inoculated with HaitiV or CVD103-HgR*. FIG. 14A is a graph depicting the anti-OSP IgA response in C57BL/6 mice inoculated with HaitiV against OSP from a serotype Inaba *V. cholerae* strain. FIG. 14B is a graph depicting the anti-OSP IgA response in Swiss-Webster mice inoculated with either HaitiV (black circles) or CVD103-HgR* (empty squares and dashed lines) against OSP from a serotype Inaba *V. cholerae* strain. FIG. 14C is a graph depicting the anti-OSP IgG response in C57BL/6 mice inoculated with HaitiV against OSP from a serotype Inaba *V. cholerae* strain. FIG. 14D is a graph depicting the anti-OSP IgG response in Swiss-Webster mice inoculated with either HaitiV (black circles) or CVD103-HgR* (empty squares and dashed lines) against OSP from a serotype Inaba *V. cholerae* strain. Bold black dashes above the x-axis indicate time points at which animals were orogastrically inoculated with HaitiV or CVD103-HgR*.

DETAILED DESCRIPTION

Genetically Engineered Bacteria

Provided herein is a genetically engineered *Vibrio cholerae* bacterium that may be used to induce protection from virulent *V. cholerae* within 24 hours of its administration to a subject. Vaccination with live attenuated *V. cholerae* bacterial strains is a promising strategy for inducing a protective immune response against the bacterium. The genes (ctxA and ctxB) encoding the main virulence factor in *V. cholerae*, cholera toxin (CT), are deleted from many live attenuated *V. cholerae* vaccine candidates but carried by CTXΦ, a filamentous bacteriophage that infects *V. cholerae*, integrating its genome into the *V. cholerae* chromosome and/or replicating extra-chromosomally as a plasmid. Thus, there is a significant risk that CTXΦ infection of an attenuated strain of *V. cholerae* may induce the strain to revert to a virulent state; other means of gene acquisition, including natural transformation, can also mediate reversion. Methods of preventing and/or mitigating the possibility of acquisition of cholera toxin, e.g., by CTXΦ infection or transformation by attenuated *V. cholerae* bacterial strains are highly desirable to ensure the biosafety of vaccines including the attenuated *V. cholerae* strains.

In some embodiments, the bacterium is attenuated (i.e., has reduced virulence as compared to a parental strain from which it was derived). The bacterium may include one or more of the genetic modifications described herein in order to achieve attenuated state. The genetic modifications include, but are not limited to, a complete or partial deletion of a gene, and genetic modifications that alter the ability of the bacteria to express the gene (e.g., alterations to a promoter element that render it inoperable).

In some embodiments, the bacterium is of the genus *Vibrio*. In some embodiments, the bacterium is of the species *Vibrio cholerae*. Any *V. cholerae* strain, including clinical isolates, can be used as described herein. In some embodiments, the *V. cholerae* bacterium belongs to the O1 serogroup. In some embodiments, the *V. cholerae* bacterium belongs to the O1 serogroup and is of the classical biotype. In some embodiments, the *V. cholerae* bacterium belongs to the O1 serogroup and is of the El Tor biotype. In some embodiments, the *V. cholerae* bacterium belongs to the O1 serogroup and is of the variant El Tor biotype. In some embodiments, the *V. cholerae* bacterium belongs to the O139 serogroup. In some embodiments, the *V. cholerae* bacterium belongs to the Inaba serotype. In some embodiments, the *V. cholerae* bacterium belongs to the Ogawa serotype. In some embodiments, the *V. cholerae* bacterium belongs to the Hikojima serotype. In some embodiments, the *V. cholerae* bacterium is derived from a Haitian clinical isolate. In some embodiments, the *V. cholerae* bacterium is derived from a strain selected from the group consisting of O395, N16961, B33, D34122, D34642, and D34755. In some embodiments, the *V. cholerae* bacterium is derived from an H1 strain (also known as KW3 strain (see NCBI Ref. Seq. GCF_000275645.1 and Ref. Seq. GCF_001318185.1)). Virulent *V. cholerae* strains encode two major virulence factors: cholera toxin (CT) and the toxin co-regulated pilus (TCP) that are encoded by the lysogenic bacteriophage CTXΦ and a chromosomal pathogenicity island, respectively. The bacteriophage CTXΦ can convert a non-pathogenic strain of *V. cholerae* into a pathogenic strain through phage infection, a process by which the phage genome integrates into the host genome or is maintained as a plasmid, both of which provide the host bacterium with virulence genes.

The CTXΦ genome is approximately 6.9 kb in size and is organized into two functionally distinct regions (see e.g., McLeod et al. (2005) *Mol. Microbiol.* 57(2): 347-56; and Kim et al. (2014) *J. Microbiol. Biotechnol.* 24(6): 725-31). The first region, repeat sequence 2 (RS2) includes three genes: rstR, rstA and rstB. rstA and rstB encode the proteins RstA and RstB, respectively, which are required for CTX DNA replication and integration into the bacterial chromosome. rstR encodes the repressor protein RstR. The second region, referred to as the core region, includes the genes psh, cep, orfU (gIII), ace, zot, and ctxAB. The psh, cep, orfU, ace, and zot genes encode the proteins Psh, Cep, OrfU (pIII$^{CTX}$), Ace, and Zot, respectively, which are required for phage packaging and secretion. The ctxAB is an operon includes the ctxA and ctxB genes which encode the protein subunits of cholera toxin, CtxA and CtxB, respectively. Together, ctxA and ctxB encode the Cholera toxin (CT) virulence factor that consists of one CT-A subunit and five CT-B subunits.

In some embodiments, the *V. cholerae* bacterium described herein includes one or more genetic alterations in order to reduce, inhibit and/or alter the expression of one or more CTXΦ genome genes that are integrated in the bacterial genome in order to reduce the virulence of the bacterium. The genetic alterations include, but are not limited to a deletion, mutation, insertion in the open reading frame of a CTXΦ genome gene to alter the expression and function of the gene product, or in a promoter or transcriptional regulatory element in order to inhibit the expression of the gene. In some embodiments, the *V. cholerae* bacterium includes a deletion of all copies of the integrated CTXΦ genome and the adjacent (and related) RS1 element, a satellite phage that can be packaged by CTXΦ. In some embodiments, the *V. cholerae* bacterium includes a deletion in a nucleic acid sequence of an integrated CTXΦ genome gene. In some embodiments, the *V. cholerae* bacterium has been genetically modified to completely delete a nucleic acid sequence including or consisting of a CTXΦ genome that was incorporated into the bacterial chromosome. In some embodiments, the *V. cholerae* bacterium has been genetically modified to partially delete a nucleic acid sequence including a CTXΦ genome that was incorporated into the bacterial chromosome. In some embodiments, the *V. cholerae* bacterium has been genetically modified to delete a nucleic acid sequence including or consisting of the RS2 region of a CTXΦ genome that was incorporated into the bacterial chromosome. In some embodiments, the *V. cholerae* bacterium has been genetically modified to delete a nucleic acid sequence including or consisting of the core region of a CTXΦ genome that was incorporated into the bacterial chromosome. In some embodiments, the *V. cholerae* bacterium has been genetically modified to delete a nucleic acid sequence including or consisting of a gene selected from the group consisting of rstR, rstA, rstB, psh, cep, orfU (gIII), ace, zot, ctxA and ctxB. In some embodiments, the *V. cholerae* bacterium has been genetically modified to delete a nucleic acid sequence including or consisting of a ctxA gene. In some embodiments, the *V. cholerae* bacterium has been genetically modified to delete a nucleic acid sequence including or consisting of a ctxB gene. In some embodiments, the *V. cholerae* bacterium has been genetically modified to delete a nucleic acid sequence including or consisting of a ctxAB operon. In some embodiments, the *V. cholerae* bacterium has been genetically modified to delete an attB (attachment) site where CTXΦ phage integrates.

In some embodiments, the *V. cholerae* bacterium includes one or more genetic alterations in order to reduce, inhibit and/or alter the expression of one or more RS1 satellite phage genes and/or one or more TCL satellite phage genes that are integrated in the bacterial genome. Integrated copies of the CTXΦ prophage genome are often flanked by copies of the RS1 satellite phage and the TLC satellite phage. The TLC satellite phage is involved in altering the *V. cholerae* genome to enhance the integration of the CTXΦ and RS1 phages, while the RS1 phage uses some of the CTXΦ-encoded proteins for packaging and secretion (see, e.g., Samruzzaman et al. (2014) *Infect. Immun.* 82(9): 3636-43. In some embodiments, the *V. cholerae* bacterium includes a partial deletion of an integrated copy of the RS1 phage genome. In some embodiments, the *V. cholerae* bacterium includes a complete deletion of an integrated copy of the RS1 phage genome. In some embodiments, the *V. cholerae* bacterium includes a partial deletion of an integrated copy of an RS1 phage gene. In some embodiments, the *V. cholerae* bacterium includes a complete deletion of an integrated copy of an RS1 phage gene. In some embodiments, the *V. cholerae* bacterium includes a partial deletion of an integrated copy of the TLC phage genome. In some embodiments, the *V. cholerae* bacterium includes a complete deletion of an integrated copy of the TLC phage genome. In some embodiments, the *V. cholerae* bacterium includes a partial deletion of an integrated copy of an TLC phage gene. In some embodiments, the *V. cholerae* bacterium includes a complete deletion of an integrated copy of an TLC phage gene.

In some embodiments, the *V. cholerae* bacterium includes a genetic modification that renders the bacterium incapable of facilitating the replication of CTXΦ. For example, the DNA binding protein HUβ promotes replication of the plasmid form of CTXΦ in *V. cholerae* (see, Martinez et al. (2015) *PLoS Genetics* 11(5): e1005256, the entire contents of which are expressly incorporated herein by reference). In *V. cholerae*, HUβ is encoded by hupB (also known as VC1919). Thus, in some embodiments, the *V. cholerae* bacterium includes a genetic alteration that alters the function and/or expression of hupB. In some embodiments, the *V. cholerae* bacterium includes a partial deletion of the hupB gene. In some embodiments, the *V. cholerae* bacterium includes a complete deletion of the hupB gene.

In some embodiments, the *V. cholerae* bacterium includes a genetic modification that renders the bacterium incapable of producing and/or secreting a multifunctional-autoprocessing repeats-in-toxin (MARTX) toxin. The MARTX toxin rtx gene loci in *V. cholerae* consists of two divergently transcribed operons rtxHCA and rtxBDE. In *V. cholerae*, the MARTX toxin, RtxA, is encoded by the gene rtxA, and facilitates bacterial colonization of the intestine (see, e.g., Satchell et al. (2015) *Microbiol. Spectr.* 3(3) and Fullner et al. (2002) *J. Exp. Med.* 195(11): 1455-62; and Olivier et al. (2009) *PLoS One* 4(10): e7352, the entire contents of each of which are incorporated herein by reference). Adjacent gene rtxC encodes the putative acytltransferase rtxC, while rtxH encodes a hypothetical protein with uncharacterized function (see Gavin and Satchell (2015) *Pathog. Dis.* 73(9): ftv092, the entire contents of which are incorporated herein by reference). The genes of the rtxBDE operon encode a dedicated MARTX toxin Type 1 secretion system (T1SS), whereby rtxB and rtxE encode the ATPase proteins RtxB and RtxE, respectively, and rtxD encodes the transmembrane protein RtxD which acts in concert with the outer membrane porin TolC to secrete RtxA from the bacterial cytoplasm to the extracellular environment (see Gavin and Satchell (2015)). In some embodiments, the *V. cholerae* bacterium includes a genetic alteration that alters the function of the MARTX toxin. In some embodiments, the *V. cholerae* bacterium includes a partial deletion of the rtxA gene. In some embodiments, the *V. cholerae* bacterium includes a complete deletion of the rtxA gene. In some embodiments, the *V. cholerae* bacterium includes a partial deletion of the rtxB gene. In some embodiments, the *V. cholerae* bacterium includes a complete deletion of the rtxB gene. In some embodiments, the *V. cholerae* bacterium includes a partial deletion of the rtxC gene. In some embodiments, the *V. cholerae* bacterium includes a complete deletion of the rtxC gene. In some embodiments, the *V. cholerae* bacterium includes a partial deletion of the rtxD gene. In some embodiments, the *V. cholerae* bacterium includes a complete deletion of the rtxD gene. In some embodiments, the *V. cholerae* bacterium includes a partial deletion of the rtxE gene. In some embodiments, the *V. cholerae* bacterium includes a complete deletion of the rtxE gene. In some embodiments, the *V. cholerae* bacterium includes a partial deletion of the rtxH gene. In some embodiments, the *V. cholerae* bacterium includes a complete deletion of the rtxH gene. In some embodiments, the *V. cholerae* bacterium includes a partial deletion of the rtxHCA operon. In some embodiments, the *V. cholerae* bacterium includes a complete deletion of the rtxHCA operon. In some embodiments, the *V. cholerae* bacterium includes a partial deletion of the rtxBDE operon. In some embodiments, the *V. cholerae* bacterium includes a complete deletion of the rtxBDE operon.

In some embodiments, the *V. cholerae* bacterium includes a genetic modification to reduce the reactogenicity of the bacterium after administration to a subject (e.g., a human subject). Some attenuated oral *V. cholerae* vaccine strains have induced reactogenicity symptoms that included non-choleric diarrhea and abdominal cramps; however, *V. cholerae* strains lacking flagellin-encoding genes have been demonstrated to exhibit reduced reactogenicity in animal models (see, e.g., Rui et al. (2010) *Proc. Nat'l. Acad. Sci. USA* 107(9): 4359-64, the entire contents of which are expressly incorporated herein by reference.) *V. cholerae* includes two operons, flaAC and flaDBE, which include five flagellin-encoding genes. In some embodiments, the *V. cholerae* bacterium includes a genetic alteration that alters the function of at least one gene encoding a flagellin. In some embodiments, the *V. cholerae* bacterium includes a partial deletion in a gene encoding a flagellin. In some embodiments, the *V. cholerae* bacterium includes a complete deletion in a gene encoding a flagellin. In some embodiments, the *V. cholerae* bacterium includes a complete or partial deletion in a flagellin gene selected from the group consisting of flaA, flaB, flaC, flaD, and flaE. In some embodiments, the *V. cholerae* bacterium includes a complete or partial deletion of the flaAC operon. In some embodiments, the *V. cholerae* bacterium includes a complete or partial deletion of the flaBDE operon. In some embodiments, the *V. cholerae* bacterium includes a complete or partial deletion of both the flaAC operon and the flaBDE operon.

In some embodiments, the *V. cholerae* bacterium includes a deletion in an antibiotic resistance gene to prevent the dispersal of the antibiotic resistance genes to other bacteria. In some embodiments, the *V. cholerae* bacterium includes a partial deletion in an antibiotic resistance gene. In some embodiments, the *V. cholerae* bacterium includes a complete deletion in an antibiotic resistance gene. In some embodiments, the antibiotic resistance gene is selected from the group consisting of floR (which confers resistance to chloramphenicol), strAB (which confers resistance to streptomycin), sul2 (which confers resistance to sulfisoxazole and sulfamethoxazole), and dfrA (which confers resistance to trimethoprim). In some embodiments, the *V. cholerae* bacterium includes a complete deletion of each of the following antibiotic resistance genes: floR, strAB, dfrA, and sul2.

In some embodiments, the *V. cholerae* bacterium includes a genetic modification that renders the bacterium incapable of producing RecA. The gene recA encodes the multifunctional protein RecA, which is involved in homologous recombination, DNA repair, and the SOS response (see, e.g., Thompson et al. (2004) *Int. J. Syst. Evol. Microbiol.* 54 (Pt. 3): 919-24, the entire contents of which are expressly incorporated herein by reference). In some embodiments, the *V. cholerae* bacterium includes a deletion in the recA gene. In some embodiments, the deletion is a partial deletion. In some embodiments, the deletion is a complete deletion. Without wishing to be bound by any particular theory, deletion of recA prevents homologous recombination-dependent gene acquisition by the *V. cholerae* bacterium and its ability to resolve mutations that arise from environmental exposure such as UV light.

In some embodiments, the *V. cholerae* bacterium includes a heterologous nucleic acid or a heterologous gene. The term "heterologous nucleic acid" or "heterologous gene" refers to a nucleic acid that is not normally found in a given cell in nature (e.g., a nucleic acid that is exogenously introduced into a given cell; or a nucleic acid that has been introduced into the host cell in a form that is different from the corresponding native nucleic acid). It will be readily understood by those of skill in the art that a heterologous nucleic acid may comprise a gene that is codon-optimized for use in a *V. cholerae* bacterium described herein.

In some embodiments, the *V. cholerae* bacterium includes a heterologous nucleic acid encoding an antigenic polypeptide. In some embodiments, the expression of the nucleic acid encoding the antigenic polypeptide is operably-linked to a constitutive promoter. In some embodiments, the nucleic acid encoding the antigenic polypeptide is operably-linked to an inducible promoter. In some embodiments, the heterologous nucleic acid encoding an antigenic polypeptide is integrated in the bacterial genome. In some embodiments, the heterologous nucleic acid encoding an antigenic polypeptide is present on a plasmid. In some embodiments, the antigenic polypeptide is the cholera toxin subunit CtxB. Expression of the cholera toxin CtxB subunit by the *V. cholerae* bacterium described herein may be particularly advantageous as it may promote the induction of an anti-CtxB immune response in a subject to whom the bacterium is administered, thereby resulting in immunoprotection against *V. cholerae* and enterotoxigenic *E. coli* (ETEC) (see, e.g., Kauffman et al. (2016) *mBio* 7(6): e02021-16, the entire contents of which are expressly incorporated herein by reference). Thus, in some embodiments, the *V. cholerae* bacterium includes a heterologous nucleic acid comprising the *V. cholerae* ctxB gene. In some embodiments, the *V. cholerae* bacterium includes a heterologous nucleic acid comprising the *V. cholerae* ctxB gene is operably linked to an inducible promoter (e.g., a $P_{htpg}$ promoter). In some embodiments, the *V. cholerae* bacterium includes a heterologous nucleic acid comprising the *V. cholerae* ctxB gene is operably linked to an inducible promoter. In some embodiments, the heterologous nucleic acid comprising the *V. cholerae* ctxB gene is present on the bacterial chromosome. In some embodiments, the *V. cholerae* bacterium includes the mutation N900_11550::Phtpg-ctxB. In some embodiments, the *V. cholerae* bacterium includes a heterologous nucleic acid encoding CtxB integrated into the chromosome at a locus homologous to the N900_11550 locus of HaitiWT (Bioproject Accession No. PRJNA215281; Biosample Accession No. SAMN04191514). In some embodiments, the *V. cholerae* bacterium includes a heterologous nucleic acid encoding CtxB integrated into the chromosome at a locus homologous to the N900_RS07040 locus of HaitiWT. In some embodiments, the *V. cholerae* bacterium includes a heterologous nucleic acid encoding CtxB integrated into the chromosome at a locus homologous to the N900_RS07045 locus of HaitiWT.

In some embodiments, the *V. cholerae* bacterium includes a bacterial chromosome, wherein the bacterial chromosome includes or consists of the nucleic acid sequence of SEQ ID NO: 7. In some embodiments, the *V. cholerae* bacterium includes a bacterial chromosome, wherein the bacterial chromosome includes or consists of the nucleic acid sequence of SEQ ID NO: 51. In some embodiments, the *V. cholerae* bacterium includes a first bacterial chromosome and a second bacterial chromosome, wherein the first bacterial chromosome includes or consists of the nucleic acid sequence of SEQ ID NO: 7, and the second bacterial chromosome includes or consists of the nucleic acid sequence of SEQ ID NO: 51. In some embodiments, the *V. cholerae* bacterium has mutations in the same genes, relative to its parental strain, as the strain having ATCC deposit number PTA-125138. In some embodiments, the *Vibrio cholerae* bacterium is a *V. cholerae* strain having ATCC deposit number PTA-125138 (described herein as HaitiV).

Programmable RNA-Guided Nuclease Systems

The disclosure further provides recombinant bacterial strains comprising a programmable RNA-guided nuclease system that specifically targets a gene (e.g., a virulence gene) that was previously deleted from the bacterial strain. By targeting the gene that was deleted from the bacterial strain, reversion of a virulent phenotype by the recombinant bacterium may be prevented and/or ameliorated (e.g., by preventing re-acquisition of the gene). The use of programmable RNA-guided nuclease systems as described herein is particularly useful in live attenuated vaccine bacterial strains in order to maintain the attenuated phenotype of the strains.

Any attenuated bacterial strain can be modified to express a programmable RNA-guided nuclease system to prevent and/or ameliorate reversion to a virulent phenotype. For example, live attenuated bacterial strains of the species *V. cholerae*, *Salmonella enterica*, *Shigella flexneri*, *Shigella sonnei*, *Shigella dysenteriae*, *Bordetella pertussis*, and *Clostridioides difficile* (previously *Clostridium difficile*) can be genetically-manipulated to express a programmable RNA-guided nuclease system targeting a gene that is deleted in the strain (i.e., as compared to the strain from which the attenuated bacterial strain was derived). Exemplary live attenuated bacterial strains and a description of the virulence genes that are deleted in the strains are provided in Table 1. Exemplary sequences of the virulence genes that are deleted in these live attenuated bacterial strains are provided in Table 2. Each of the bacterial strains provided in Table 1 can be genetically modified as described herein to include a RNA-guided nuclease system that specifically targets at least one of the genes that has been deleted in the strain. For example, in some embodiments, the bacterial strain is a *V. cholerae* strain including a deletion in a ctxA gene, as well as a programmable RNA-guided nuclease system (e.g., a heterologous nucleic acid sequence encoding a Cas9 nuclease molecule and a heterologous nucleic acid sequence encoding a guide RNA (gRNA)) targeting a ctxA gene. In some embodiments, the bacterial strain is a *S. enterica* strain including a deletion in at least one virulence gene selected from aroC, aroD, htrA, ssaV, cya, crp, phoP, phoQ, guaB, guaA, clpX, and clpP, as well as a programmable RNA-guided nuclease system targeting at least one of the deleted virulence genes (e.g., aroC, aroD, htrA, ssaV, cya, crp, phoP, phoQ, guaB, guaA, clpX, and clpP). In some embodiments, the bacterial strain is a *S. flexneri* strain including a deletion in at least one virulence gene selected from guaB, guaA, set, sen, virG/icsA, luc, aroA, and msbB2, as well as a programmable RNA-guided nuclease system targeting at least one of the deleted virulence genes (e.g., guaB, guaA, set, sen, virG/icsA, luc, aroA, and msbB2). In some embodiments, the bacterial strain is a *S. dysenteriae* strain including a deletion in at least one virulence gene selected from guaB, guaA, sen, stxA, stxB, and msbB2, as well as a programmable RNA-guided nuclease system targeting at least one of the deleted virulence genes (e.g., guaB, guaA, sen, stxA, stxB, and msbB2). In some embodiments, the bacterial strain is a *S. sonnei* strain including a deletion in a stxA gene and/or a stxB gene, as well as a programmable RNA-guided nuclease system targeting the deleted virulence gene (e.g., stxA and/or stxB). In some embodiments, the bacterial strain is a *B. pertussis* strain including a deletion in a dnt gene, a aroA gene and/or an aroQ gene, as well as a programmable RNA-guided nuclease system targeting the deleted virulence gene (e.g., dnt, aroA and/or aroQ). In some embodiments, the bacterial strain is a *C. difficile* strain including a deletion in a tcdA gene and/or a tcdB gene, as well as a programmable RNA-guided nuclease system targeting the deleted virulence gene (e.g., tcdA and/or tcdB).

In some embodiments, the bacterium is a *V. cholerae* bacterium having a programmable RNA-guided nuclease system that specifically targets a CTXΦ nucleic acid, thereby preventing or interrupting one or more of the following processes: the insertion of CTXΦ genetic material into the bacterial genome, the replication of CTXΦ, the assembly of CTXΦ, and/or the release of CTXΦ from the bacterium; or killing the bacterium comprising an integrated copy of the CTXΦ genome. In some embodiments, the programmable RNA-guided nuclease system targets a ctxA gene.

Relevant nuclease systems that may be used include, but are not limited to: zinc finger nucleases, transcription activator-like effector nucleases (TALENs), CRISPR from *Prevotella* and *Francisella* 1 (Cpf1) nucleases, meganucleases, and CRISPR/Cas9 nuclease systems. As used herein, the term "edits" in reference to a programmable RNA-guided nuclease system includes mutations such as, a point mutation, an insertion, a deletion, a frameshift, or a missense mutation at a target nucleic acid. The RNA-guided nuclease system includes guide RNAs comprising a sequence that is complementary to the sequence of a nucleic acid (i.e., a targeting domain) in the virulence gene (e.g., a gene present in a CTXΦ genome such as ctxA), and a sequence (e.g., a PAM sequence or a direct repeat sequence) that is targetable by a nuclease molecule (e.g., a Cas9 nuclease molecule). The term guide RNA ("gRNA"), as used herein, includes any RNA molecule (e.g., gRNA, crRNA, tracrRNA, sgRNA, and others) guiding a nuclease molecule to a target nucleic acid. Upon successful targeting, the nuclease molecule cleaves the nucleic acid in the virulence gene (e.g., ctxA). By specifically targeting the virulence gene with a programmable RNA-guided nuclease system, the reversion of an attenuated bacterium (e.g., an attenuated *Salmonella enterica* or *V. cholerae* bacterium) to a virulent bacterium may be prevented and/or ameliorated. The term "prevention" refers to any reduction, no matter how slight (e.g., need not be 100% reduction), of the risk that an attenuated bacterium to revert to a virulent form.

In some embodiments, the bacterium includes a heterologous nucleic acid encoding a Cas9 nuclease molecule. Although the present examples exemplify the use of a *Streptococcus pyogenes* Cas9 nuclease molecule (SpCas9), other Cas9 nuclease molecules from other species can also be used (e.g., *Staphylococcus aureus* Cas9 nuclease molecule (SaCas9)), as discussed below. The sequences of multiple Cas9 nuclease molecules, as well as their respective PAM sequences, are known in the art (see, e.g., Kleinstiver et al. (2015) *Nature* 523 (7561): 481-5; Hou et al. (2013) *Proc. Natl. Acad. Sci. U.S.A.*; Fonfara et al. (2014) *Nucleic Acids Res.* 42: 2577-90; Esvelt et al. (2013) *Nat. Methods* 10: 1116-21; Cong et al. (2013) *Science* 339: 819-23; and Horvath et al. (2008) *J. Bacteriol.* 190: 1401-12; PCT Publication Nos. WO 2016/141224, WO 2014/204578, and WO 2014/144761; U.S. Pat. No. 9,512,446; and US Publication No. 2014/0295557; the entire contents of each of which are incorporated herein by reference). Variants of the SpCas9 system can also be used (e.g., truncated sgRNAs (Tsai et al. (2015) *Nat. Biotechnol.* 33: 187-97; Fu et al. (2014) *Nat. Biotechnol.* 32: 279-84), nickase mutations (Mali et al. (2013) *Nat. Biotechnol.* 31: 833-8 (2013); Ran et al. (2013) *Cell* 154: 1380-9), FokI-dCas9 fusions (Guilinger et al. (2014) *Nat. Biotechnol.* 32: 577-82; Tsai et al. (2014) *Nat. Biotechnol.* 32: 569-76; and PCT Publication No. WO 2014/144288; the entire contents of each of which are incorporated herein by reference). The nucleases can include one or more of SpCas9 D1135E variant; SpCas9 VRER variant; SpCas9 EQR variant; SpCas9 VQR variant; *Streptococcus thermophilus* Cas9 nuclease molecule (StCas9); *Treponema denticola* Cas9 nuclease molecule (TdCas9); or *Neisseria meningitidis* Cas9 nuclease molecule (NmCas9), as well as variants thereof that are at least 80%, 85%, 90%, 95%, 96%, 97%, 98%, 99% or 100% identical thereto that retain at least one function of the enzyme from which they are derived, e.g., the ability to complex with a gRNA, bind to target DNA specified by the gRNA, and alter the sequence (e.g., cleave) of the target DNA.

In some embodiments, the bacterium (e.g., a *V. cholerae* bacterium) includes a heterologous nucleic acid encoding a Cpf1 nuclease molecule. Cpf1 is a Cas protein that can be programmed to cleave target DNA sequences (Zetsche et al. (2015) *Cell* 163: 759-71; Schunder et al. (2013) *Int. J. Med. Microbiol.* 303: 51-60; Makarova et al. (2015) *Nat. Rev. Microbiol.* 13: 722-36; Fagerlund et al. (2015) *Genome Biol.* 16: 251). In some embodiments, the Cpf1 nuclease molecule is *Acidaminococcus* sp. BV3L6 (AsCpf1; NCBI Reference Sequence: WP_021736722.1), or a variant thereof. In some embodiments, the Cpf1 nuclease molecule is *Lachnospiraceae bacterium* ND2006 (LbCpf1; GenBank Acc No. WP_051666128.1) or a variant thereof. Unlike SpCas9, Cpf1 requires only a single 42-nt crRNA, which has 23 nt at its 3' end that are complementary to the protospacer of the target DNA sequence (Zetsche et al. (2015)). Furthermore, whereas SpCas9 recognizes an NGG PAM sequence that is 3' of the protospacer, AsCpf1 and LbCp1 recognize TTTN PAMs that are found 5' of the protospacer (Zetsche et al. (2015)). In some embodiments, the Cpf1 nuclease molecule is a variant of a wild-type Cpf1 molecule that is at least 80%, 85%, 90%, 95%, 96%, 97%, 98%, 99% or 100% identical to a wild-type Cpf1 nuclease molecule, and retains at least one function of the enzyme from which it was derived, e.g., the ability to complex with a gRNA, bind to target DNA specified by the gRNA, and alter the sequence (e.g., cleave) of the target DNA To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch algorithm (see Needleman and Wunsch (1970) *J. Mol. Biol.* 48: 444-53) which has been incorporated into the GAP program in the GCG software package, using a Blossum 62 scoring matrix with a gap penalty of 12, a gap extend penalty of 4, and a frameshift gap penalty of 5.

The amino acid sequence of wild type SpCas9 is as follows:

(SEQ ID NO: 1)
MDKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

ENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD

The amino acid sequence of wild type SaCas9 is as follows:

(SEQ ID NO: 2)
MKRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLSE

EEFSAALLHLAKRRGVHNVNEVEEDTGNELSTKEQISRNSKALEEKYVAEL

QLERLKKDGEVRGSINRFKTSDYVKEAKQLLKVQKAYHQLDQSFIDTYIDL

LETRRTYYEGPGEGSPFGWKDIKEWYEMLMGHCTYFPEELRSVKYAYNADL

YNALNDLNNLVITRDENEKLEYYEKFQIIENVFKQKKKPTLKQIAKEILVN

EEDIKGYRVTSTGKPEFTNLKVYHDIKDITARKEIIENAELLDQIAKILTI

YQSSEDIQEELTNLNSELTQEEIEQISNLKGYTGTHNLSLKAINLILDELW

HINDNQIAIFNRLKLVPKKVDLSQQKEIPTTLVDDFILSPVVKRSFIQSIK

VINAIIKKYGLPNDIIIELAREKNSKDAQKMINEMQKRNRQTNERIEEIIR

TTGKENAKYLIEKIKLHDMQEGKCLYSLEAIPLEDLLNNPFNYEVDHIIPR

SVSFDNSFNNKVLVKQEENSKKGNRTPFQYLSSSDSKISYETFKKHILNLA

KGKGRISKTKKEYLLEERDINRFSVQKDFINRNLVDTRYATRGLMNLLRSY

FRVNNLDVKVKSINGGFTSFLRRKWKFKKERNKGYKHHAEDALIIANADFI

FKEWKKLDKAKKVMENQMFEEKQAESMPEIETEQEYKEIFITPHQIKHIKD

FKDYKYSHRVDKKPNRELINDTLYSTRKDDKGNTLIVNNLNGLYDKDNDKL

KKLINKSPEKLLMYHHDPQTYQKLKLIMEQYGDEKNPLYKYYEETGNYLTK

YSKKDNGPVIKKIKYYGNKLNAHLDITDDYPNSRNKVVKLSLKPYRFDVYL

DNGVYKFVTVKNLDVIKKENYYEVNSKCYEEAKKLKKISNQAEFIASFYNN

DLIKINGELYRVIGVNNDLLNRIEVNMIDITYREYLENMNDKRPPRIIKTI

ASKTQSIKKYSTDILGNLYEVKSKKHPQIIKKG.

In some embodiments, the bacterium includes a heterologous nucleic acid sequence encoding a gRNA, wherein the gRNA includes a targeting domain which is complementary with a target nucleic acid sequence of a virulence gene (e.g., a CTXΦ genome gene such as ctxA). In some embodiments, the gRNA includes a targeting domain which is complementary with a target nucleic acid sequence present on a virulence gene listed in Table 2 (e.g., ctxA, aroD, or htrA). Methods of designing and making gRNAs with specificity for particular targets are known in the art and are described, for example, in Prykhozhij et al. (2015) *PLos One* 10(3): e0119372; Doench et al. (2014) *Nat. Biotechnol.* 32(12):

1262-7; and Graham et al. (2015) *Genome Biol.* 16: 260, each of which are expressly incorporated herein by reference.

V. cholerae Having Programmable RNA-Guided Nuclease Systems

In some embodiments, the virulence gene is a CTXΦ gene and the bacterium is an attenuated *V. cholerae* bacterium. Without wishing to be bound by any particular theory, by specifically targeting a nucleic acid sequence of the CTXΦ genome, it is possible to prevent integration of the CTXΦ genome into the *V. cholerae* bacterial genome and/or maintenance of the CTXΦ genome as a plasmid, either of which may cause the bacterium to adapt and/or revert to a virulent state. The gRNA may comprise a targeting domain complementary with a target nucleic acid sequence present in the CTXΦ genome; however, it is preferable that the gRNA specifically target the nucleic acid sequence of the CTXΦ genome and not a bacterial genome nucleic acid sequence. In some embodiments, the gRNA includes a targeting domain complementary with a target nucleic acid sequence present in a CTXΦ gene (e.g., rstR, rstA, rstB, psh, cep, orfU (gIII), ace, zot, ctxA and ctxB). It is particularly desireable to target ctxA. In some embodiments, the gRNA includes a targeting domain complementary with a target nucleic acid sequence present in a ctxA gene. In some embodiments, the gRNA includes the nucleic acid sequence: 5'-cctgat-gaaataaagcagtcgttttagagctagaaatagcaagt-taaaataaggctagtccgttatcaacttgaaaaagtgg caccgagtcggtgc-3' (SEQ ID NO: 3; targeting sequence specific for ctxA highlighted in bold). In some embodiments, the gRNA includes the nucleic acid sequence 5'-tttttgtcgat-tatcttgctgttctagagagcgggagctcaagttagaataaggctagtccgtat-tcagtgcgggagcacgg caccgattcggtgc-3' (SEQ ID NO: 4; targeting sequence specific for rstA highlighted in bold). In some embodiments, the gRNA includes the nucleic acid sequence 5'-taaacaaagggagcattatagttggagaggcatgagaatgc-caagttccaataaggctagtccgtacacacctaggaga ctaggggcaccgagtcggtgc-3' (SEQ ID NO: 5; targeting sequence specific for ctxA highlighted in bold).

As described above, in some embodiments, the genetically engineered *V. cholerae* bacterium may include a heterologous nucleic acid, wherein the heterologous nucleic acid includes a ctxB gene. Without wishing to be bound by any particular theory, expression of CtxB may induce an anti-ctxB immune response in a subject. This anti-ctxB immune response may protect against diarrheal disease caused by either a virulent *V. cholerae* bacterial strain and/or enterotoxigenic *E. coli* (ETEC) (see, e.g., Kauffman et al. (2016) *MBio.* 7(6): e 02021-16). One of skill in the art will readily appreciate that if the bacterium includes a heterologous nucleic acid comprising a ctxB gene as well as a gRNA comprising a targeting domain complementary with a target nucleic acid sequence present in a ctxB gene, either the heterologous nucleic acid comprising the ctxB gene, or the nucleic acid encoding the gRNA may be genetically engineered such that the gRNA does not target the heterologous nucleic acid comprising the ctxB gene. For example, the heterologous nucleic acid comprising the ctxB gene may be modified to replace a codon sequence with a synonymous codon sequence such that it is not complementary to the gRNA targeting domain sequence.

TABLE 1

Exemplary Live Vaccine Strains

| Bacterial Pathogen | Strain | Vaccine Name | Gene Deletions | Exemplary Sequence(s) from Table 2 | Reference |
|---|---|---|---|---|---|
| *Vibrio cholerae* | VC O1 Inaba 569B | CVD103-HgR | 550 bp of ctxA gene | A | Pastor et al. (2013) *Vaccine* 31: 4069-78. |
| *Vibrio cholerae* | VC strain C7258 El Tor Ogawa | *V. cholerae* 638 | CTX prophage deletion | A | |
| *Vibrio cholerae* | VC O1, El Tor Inaba s | Peru-15 | Cholera toxin encoding core deletion, recA region modification | A | |
| *Salmonella enterica Typhi* | ISP1820 | CVD 906 | ΔaroC ΔaroD | B, C | Tennant and Levine (2015) *Vaccine* 33 Suppl. 3: C36-41. |
| *Salmonella enterica Typhi* | Ty2 | CVD 908 | ΔaroC ΔaroD | B, C | |
| *Salmonella enterica Typhi* | ISP1820 | CVD 906-htrA | ΔaroC ΔaroD ΔhtrA | B, C, D | |
| *Salmonella enterica Typhi* | Ty2 | CVD 908-htrA | ΔaroC ΔaroD ΔhtrA | B, C, D | |
| *Salmonella enterica Typhi* | Ty2 | CVD 909 | ΔaroC ΔaroD Ptac-tviA | B, C | |
| *Salmonella enterica Typhi* | Ty2 | Typhella (M01ZH09) 3927 | ΔaroC ΔssaV | B, E | |
| *Salmonella enterica Typhi* | Ty2 | X3927 | Δcya Δcrp | F, G | |

TABLE 1-continued

Exemplary Live Vaccine Strains

| Bacterial Pathogen | Strain | Vaccine Name | Gene Deletions | Exemplary Sequence(s) from Table 2 | Reference |
|---|---|---|---|---|---|
| Salmonella enterica Typhi | Ty2 | Ty800 | ΔphoPQ | H, I | |
| Salmonella enterica Paratyphi A | ATCC 9150 | CVD 1902 | ΔguaBA ΔclpX | J, K, L | |
| Salmonella enterica Paratyphi A | MGN9772 | MGN10028 | ΔphoPQ | H, I | |
| Salmonella enterica Paratyphi B | CMF 6999 | CVD 2005 | ΔguaBA ΔclpX | J, K, L | |
| Salmonella enterica Typhimurium | I77 | CVD 1921 | ΔguaBA ΔclpP | J, K, M | |
| Salmonella enterica Typhimurium | D65 | CVD 1931 | ΔguaBA ΔclpX | J, K, L | |
| Salmonella enterica Enteritidis | R11 | CVD 1941 | ΔguaBA ΔclpP | J, K, M | |
| Salmonella enterica Enteritidis | R11 | CVD 1944 | ΔguaBA ΔclpX | J, K, L | |
| Shigella flexneri | 2457T | CVD 1207 | ΔguaBA Δset Δsen ΔvirG | N, O, P, Q, R | Mani et al. (2016) |
| Shigella flexneri | 2457T | CVD 1208 | ΔguaBA Δset Δsen | N, O, P, Q | Vaccine 34: 2887-94. |
| Shigella flexneri | 2457T | CVD 1208S | ΔguaBA Δset Δsen | N, O, P, Q | |
| Shigella flexneri | J17B | CVD 1213 | ΔguaBA | N, O | |
| Shigella flexneri | CCH060 | CVD 1215 | ΔguaBA | N, O | |
| Shigella flexneri | 2457T | SC602 | ΔicsA Δluc | R, S | |
| Shigella flexneri | 2457T | CVD 1203 | ΔaroA ΔvirG | R, T | |
| Shigella sonnei | Moseley | WRSs1 | ΔvirG | R | |
| Shigella sonnei | Moseley | WRSs2 | ΔvirG ΔsenA ΔsenB | Q, R | |
| Shigella sonnei | Moseley | WRSs3 | ΔvirG ΔsenA ΔsenB ΔmsbB2 | Q, R, U | |
| Shigella dysenteriae | 1617 | CVD 1251 | ΔguaBA | N, O | |
| Shigella dysenteriae | 1617 | CVD 1254 | ΔstxAB | V, W | |
| Shigella dysenteriae | 1617 | CVD 1255 | ΔguaBA Δsen ΔstxAB | N, O, V, W | |
| Shigella dysenteriae | 1617 | CVD 1256 | ΔguaBA Δsen ΔstxAB::mLpp-stxB | N, O, V, W | |
| Shigella dysenteriae | 1617 | CVD 1257 | ΔguaBA Δsen ΔstxAB::trc-stxB | N, O, V, W | |
| Shigella dysenteriae | 1617 | CVD 1258 | ΔguaBA Δsen ΔstxAB pOmpC-StxB | N, O, V, W | |
| Shigella dysenteriae | 1617 | CVD 1259 | ΔguaBA Δsen ΔstxAB pTrc-StxB | N, O, V, W | |
| Bordetella pertussis | 12822 | BPZE1 | ΔampG::Ec_ampG Δptx::ptx* Δdnt | X, Y | Locht (2017) |
| Bordetella pertussis | CN2992 FS | aroA | aroA | Z | Vaccine pii: |
| Bordetella pertussis | BP1 | aroA | aroA | Z | S0264-410X(17) |

TABLE 1-continued

Exemplary Live Vaccine Strains

| Bacterial Pathogen | Strain | Vaccine Name | Gene Deletions | Exemplary Sequence(s) from Table 2 | Reference |
|---|---|---|---|---|---|
| *Bordetella pertussis* | ATCC 9340 | aroQBP | aroQ::kan | AA | 31619-5 (doi: 10.1016/j.vaccine.2017) |

TABLE 2

Deleted Virulence Genes from Exemplary Live Vaccine Strains

| Exemplary Sequences | Virulence Gene | Nucleotide Accession | Start | Stop | Strand | Protein | Organism | Assembly |
|---|---|---|---|---|---|---|---|---|
| A | ctxA | NC_002505.1 | 1567338 | 1568114 | − | WP_001881225.1 | *Vibrio cholerae* O1 biovar El Tor str. N16961 | GCF_000006745.1 |
| | ctxA | NC_009456.1 | 566372 | 567148 | + | WP_001881225.1 | *Vibrio cholerae* O395 | GCF_000016245.1 |
| | ctxA | NC_009457.1 | 1115147 | 1115923 | − | WP_001881225.1 | *Vibrio cholerae* O395 | GCF_000016245.1 |
| | ctxA | NC_012582.1 | 1646566 | 1647342 | − | WP_001881225.1 | *Vibrio cholerae* O395 | GCF_000021625.1 |
| | ctxA | NC_012583.1 | 696794 | 697570 | − | WP_001881225.1 | *Vibrio cholerae* O395 | GCF_000021625.1 |
| B | aroC | NC_003198.1 | 2449561 | 2450646 | − | WP_000918475.1 | *Salmonella enterica* subsp. *enterica* serovar *Typhi* str. CT18 | GCF_000195995.1 |
| | aroC | NC_004631.1 | 554066 | 555151 | + | WP_000918475.1 | *Salmonella enterica* subsp. *enterica* serovar Typhi str. Ty2 | GCF_000007545.1 |
| | aroC | NC_016832.1 | 554020 | 555105 | + | WP_000918475.1 | *Salmonella enterica* subsp. *enterica* serovar Typhi str. P-stx-12 | GCF_000245535.1 |
| | aroC | NC_021176.1 | 554066 | 555151 | + | WP_000918475.1 | *Salmonella enterica* subsp. *enterica* serovar Typhi str. Ty21a | GCF_000385905.1 |
| | aroC | NZ_AJGK01000087.1 | 3952 | 5037 | − | WP_000918475.1 | *Salmonella enterica* subsp. *enterica* serovar Typhi str. BL196 | GCF_000256015.1 |
| C | aroD | NC_003198.1 | 1681680 | 1682438 | + | WP_000860215.1 | *Salmonella enterica* subsp. *enterica* serovar Typhi str. CT18 | GCF_000195995.1 |
| | aroD | NC_004631.1 | 1298692 | 1299450 | − | WP_000860215.1 | *Salmonella enterica* subsp. enterica serovar Typhi str. Ty2 | GCF_000007545.1 |
| | aroD | NC_016832.1 | 1297665 | 1298423 | − | WP_000860215.1 | *Salmonella enterica* subsp. *enterica* serovar Typhi str. P-stx-12 | GCF_000245535.1 |
| | aroD | NC_021176.1 | 1298692 | 1299450 | − | WP_000860215.1 | *Salmonella enterica* subsp. enterica serovar Typhi str. Ty21a | GCF_000385905.1 |
| | aroD | NZ_AESR01000018.1 | 161153 | 161911 | − | WP_000860215.1 | *Salmonella enterica* subsp. *enterica* serovar Montevideo str. SARB31 | GCF_000238555.1 |
| D | htrA | NC_003198.1 | 241500 | 242927 | + | WP_000753959.1 | *Salmonella enterica* subsp. *enterica* serovar *Typhi* str. CT18 | GCF_000195995.1 |
| | htrA | NC_004631.1 | 241491 | 242918 | + | WP_000753959.1 | *Salmonella enterica* subsp. *enterica* serovar Typhi str. Ty2 | GCF_000007545.1 |

TABLE 2-continued

Deleted Virulence Genes from Exemplary Live Vaccine Strains

| Exemplary Sequences | Virulence Gene | Nucleotide Accession | Start | Stop | Strand | Protein | Organism | Assembly |
|---|---|---|---|---|---|---|---|---|
| | htrA | NC_016832.1 | 241500 | 242927 | + | WP_000753959.1 | Salmonella enterica subsp. enterica serovar Typhi str. P-stx-12 | GCF_000245535.1 |
| | htrA | NC_021176.1 | 241491 | 242918 | + | WP_000753959.1 | Salmonella enterica subsp. enterica serovar Typhi str. Ty21a | GCF_000385905.1 |
| | htrA | NZ_AJGK01000045.1 | 8167 | 9594 | + | WP_000753959.1 | Salmonella enterica subsp. enterica serovar Typhi str. BL196 | GCF_000256015.1 |
| E | ssaV | NC_003198.1 | 1631029 | 1633074 | − | WP_001258227.1 | Salmonella enterica subsp. enterica serovar Typhi str. CT18 | GCF_000195995.1 |
| | ssaV | NC_004631.1 | 1348062 | 1350107 | + | WP_001258227.1 | Salmonella enterica subsp. enterica serovar Typhi str. Ty2 | GCF_000007545.1 |
| | ssaV | NC_016832.1 | 1347035 | 1349080 | + | WP_001258227.1 | Salmonella enterica subsp. enterica serovar Typhi str. P-stx-12 | GCF_000245535.1 |
| | ssaV | NC_021176.1 | 1348062 | 1350107 | + | WP_001258227.1 | Salmonella enterica subsp. enterica serovar Typhi str. Ty21a | GCF_000385905.1 |
| | ssaV | NZ_AJGK01000084.1 | 82395 | 84440 | + | WP_001258227.1 | Salmonella enterica subsp. enterica serovar Typhi str. BL196 | GCF_000256015.1 |
| F | cya | NC_003197.2 | 4146380 | 4148926 | + | WP_000281718.1 | Salmonella enterica subsp. enterica serovar Typhimurium str. LT2 | GCF_000006945.2 |
| | cya | NC_003198.1 | 3472059 | 3474605 | − | WP_000281718.1 | Salmonella enterica subsp. enterica serovar Typhi str. CT18 | GCF_000195995.1 |
| | cya | NC_004631.1 | 3457717 | 3460263 | − | WP_000281718.1 | Salmonella enterica subsp. enterica serovar Typhi str. Ty2 | GCF_000007545.1 |
| | cya | NC_010102.1 | 4091813 | 4094359 | + | WP_000281718.1 | Salmonella enterica subsp. enterica serovar Paratyphi B str. SPB7 | GCF_000018705.1 |
| | cya | NC_011080.1 | 4112677 | 4115223 | + | WP_000281718.1 | Salmonella enterica subsp. enterica serovar Newport str. SL254 | GCF_000016045.1 |
| G | crp | NC_003198.1 | 4213325 | 4213957 | − | WP_000242746.1 | Salmonella enterica subsp. enterica serovar Typhi str. CT18 | GCF_000195995.1 |
| | crp | NC_004631.1 | 4197972 | 4198604 | − | WP_000242746.1 | Salmonella enterica subsp. enterica serovar Typhi str. Ty2 | GCF_000007545.1 |
| | crp | NC_016832.1 | 4186495 | 4187127 | − | WP_000242746.1 | Salmonella enterica subsp. enterica serovar Typhi str. P-stx-12 | GCF_000245535.1 |
| | crp | NC_021176.1 | 4197969 | 4198601 | − | WP_000242746.1 | Salmonella enterica subsp. enterica serovar Typhi str. Ty21a | GCF_000385905.1 |
| | crp | NZ_AJGK01000029.1 | 11626 | 12258 | − | WP_000242746.1 | Salmonella enterica subsp. enterica serovar Typhi str. BL196 | GCF_000256015.1 |
| H | phoP | NC_003198.1 | 1228174 | 1228848 | − | WP_000986523.1 | Salmonella enterica subsp. enterica serovar Typhi str. CT18 | GCF_000195995.1 |

TABLE 2-continued

Deleted Virulence Genes from Exemplary Live Vaccine Strains

| Exemplary Sequences | Virulence Gene | Nucleotide Accession | Start | Stop | Strand | Protein | Organism | Assembly |
|---|---|---|---|---|---|---|---|---|
| | phoP | NC_004631.1 | 1752335 | 1753009 | + | WP_000986523.1 | Salmonella enterica subsp. enterica serovar Typhi str. Ty2 | GCF_000007545.1 |
| | phoP | NC_016832.1 | 1749370 | 1750044 | + | WP_000986523.1 | Salmonella enterica subsp. enterica serovar Typhi str. P-stx-12 | GCF_000245535.1 |
| | phoP | NC_021176.1 | 1752335 | 1753009 | + | WP_000986523.1 | Salmonella enterica subsp. enterica serovar Typhi str. Ty21a | GCF_000385905.1 |
| | phoP | NZ_AJGK01000079.1 | 6353 | 7027 | + | WP_000986523.1 | Salmonella enterica subsp. enterica serovar Typhi str. BL196 | GCF_000256015.1 |
| I | phoQ | NC_003198.1 | 1226711 | 1228174 | − | WP_001031689.1 | Salmonella enterica subsp. enterica serovar Typhi str. CT18 | GCF_000195995.1 |
| | phoQ | NC_004631.1 | 1753009 | 1754472 | + | WP_001031689.1 | Salmonella enterica subsp. enterica serovar Typhi str. Ty2 | GCF_000007545.1 |
| | phoQ | NC_016832.1 | 1750044 | 1751507 | + | WP_001031689.1 | Salmonella enterica subsp. enterica serovar Typhi str. P-stx-12 | GCF_000245535.1 |
| | phoQ | NC_021176.1 | 1753009 | 1754472 | + | WP_001031689.1 | Salmonella enterica subsp. enterica serovar Typhi str. Ty21a | GCF_000385905.1 |
| | phoQ | NZ_AJGK01000079.1 | 7027 | 8490 | + | WP_001031689.1 | Salmonella enterica subsp. enterica serovar Typhi str. BL196 | GCF_000256015.1 |
| J | guaB | NC_003198.1 | 2589318 | 2590790 | − | WP_001132127.1 | Salmonella enterica subsp. enterica serovar Typhi str. CT18 | GCF_000195995.1 |
| | guaB | NC_021812.2 | 3113815 | 3115287 | − | WP_001132127.1 | Salmonella enterica subsp. enterica serovar Heidelberg str. CFSAN002069 | GCF_000430085.2 |
| | guaB | NC_021814.1 | 890857 | 892329 | + | WP_001132127.1 | Salmonella enterica subsp. enterica serovar Typhimurium var. 5-str. CFSAN001921 | GCF_000430145.2 |
| | guaB | NZ_AHUK01000009.1 | 71638 | 73110 | + | WP_001132127.1 | Salmonella enterica subsp. enterica serovar Dublin | GCF_000336035.1 |
| | guaB | AE014613.1 | 414059 | 415531 | + | AA068066.1 | Salmonella enterica subsp. enterica serovar Typhi str. Ty2 | GCA_000007545.1 |
| K | guaA | NC_003198.1 | 2587671 | 2589248 | − | WP_000138293.1 | Salmonella enterica subsp. enterica serovar Typhi str. CT18 | GCF_000195995.1 |
| | guaA | NC_004631.1 | 415601 | 417178 | + | WP_000138293.1 | Salmonella enterica subsp. enterica serovar Typhi str. Ty2 | GCF_000007545.1 |
| | guaA | NC_011083.1 | 2679482 | 2681059 | − | WP_000138293.1 | Salmonella enterica subsp. enterica serovar Heidelberg str. SL476 | GCF_000020705.1 |
| | guaA | NC_011149.1 | 2590289 | 2591866 | − | WP_000138293.1 | Salmonella enterica subsp. enterica serovar Agona str. SL483 | GCF_000020885.1 |
| | guaA | NC_011205.1 | 2751892 | 2753469 | − | WP_000138293.1 | Salmonella enterica subsp. enterica serovar Dublin str. CT_02021853 | GCF_000020925.1 |

TABLE 2-continued

Deleted Virulence Genes from Exemplary Live Vaccine Strains

| Exemplary Sequences | Virulence Gene | Nucleotide Accession | Start | Stop | Strand | Protein | Organism | Assembly |
|---|---|---|---|---|---|---|---|---|
| L | clpX | NC_003198.1 | 496233 | 497504 | + | WP_000130316.1 | Salmonella enterica subsp. enterica serovar Typhi str. CT18 | GCF_000195995.1 |
| | clpX | NC_004631.1 | 2483597 | 2484868 | − | WP_000130316.1 | Salmonella enterica subsp. enterica serovar Typhi str. Ty2 | GCF_000007545.1 |
| | clpX | NC_016832.1 | 2480497 | 2481768 | − | WP_000130316.1 | Salmonella enterica subsp. enterica serovar Typhi str. P-stx-12 | GCF_000245535.1 |
| | clpX | NC_021176.1 | 2483597 | 2484868 | − | WP_000130316.1 | Salmonella enterica subsp. enterica serovar Typhi str. Ty21a | GCF_000385905.1 |
| | clpX | NZ_AJGK01000075.1 | 9768 | 11039 | − | WP_000130316.1 | Salmonella enterica subsp. enterica serovar Typhi str. BL196 | GCF_000256015.1 |
| M | clpP | NC_003197.2 | 503211 | 503834 | + | WP_000122257.1 | Salmonella enterica subsp. enterica serovar Typhimurium str. LT2 | GCF_000006945.2 |
| | clpP | NC_003198.1 | 495358 | 495981 | + | WP_000122257.1 | Salmonella enterica subsp. enterica serovar Typhi str. CT18 | GCF_000195995.1 |
| | clpP | NC_004631.1 | 2485120 | 2485743 | − | WP_000122257.1 | Salmonella enterica subsp. enterica serovar Typhi str. Ty2 | GCF_000007545.1 |
| | clpP | NC_006905.1 | 547568 | 548191 | + | WP_000122257.1 | Salmonella enterica subsp. enterica serovar Choleraesuis str. SC-B67 | GCF_000008105.1 |
| | clpP | NC_010102.1 | 2614575 | 2615198 | − | WP_000122257.1 | Salmonella enterica subsp. enterica serovar Paratyphi B str. SPB7 | GCF_000018705.1 |
| N | guaB | AE005674.2 | 2622056 | 2623522 | − | AAN44054.2 | Shigella flexneri 2a str. 301 | GCA_000006925.2 |
| | guaB | AE014073.1 | 2615645 | 2617111 | − | AAP17881.1 | Shigella flexneri 2a str. 2457T | GCA_000007405.1 |
| | guaB | CP004056.1 | 2623964 | 2625430 | − | AIL36801.1 | Shigella flexneri 2003036 | GCA_000743955.1 |
| | guaB | CP004057.1 | 2647737 | 2649203 | − | AIL41744.1 | Shigella flexneri Shi06HN006 | GCA_000743995.1 |
| | guaB | CP007037.1 | 2619532 | 2620998 | − | AKK55078.1 | Shigella flexneri G1663 | GCA_001021855.1 |
| O | guaA | AE005674.2 | 2620410 | 2621987 | − | AAN44053.1 | Shigella flexneri 2a str. 301 | GCA_000006925.2 |
| | guaA | AE014073.1 | 2613999 | 2615576 | − | AAP17880.1 | Shigella flexneri 2a str. 2457T | GCA_000007405.1 |
| | guaA | CP001383.1 | 2658104 | 2659681 | − | ADA74893.1 | Shigella flexneri 2002017 | GCA_000022245.1 |
| | guaA | CP004056.1 | 2622318 | 2623895 | − | AIL36800.1 | Shigella flexneri 2003036 | GCA_000743955.1 |
| | guaA | CP004057.1 | 2646091 | 2647668 | − | AIL41743.1 | Shigella flexneri Shi06HN006 | GCA_000743995.1 |
| P | set | CP020339.1 | 2383407 | 2387525 | − | ASQ58270.1 | Shigella flexneri 4c | GCA_002240095.1 |
| | set | CP020342.1 | 1888927 | 1893045 | + | ASQ62198.1 | Shigella flexneri 1a | GCA_002240115.1 |
| | set | CP020086.1 | 1341206 | 1345324 | + | ASQ80894.1 | Shigella flexneri 1a | GCA_002240135.1 |
| | set | CELV01000023.1 | 726 | 4844 | + | CFW93500.1 | Shigella flexneri 2a | GCA_001078805.1 |
| | set | NC_004337.2 | 3067737 | 3071855 | − | NP708747.3 | Shigella flexneri 2a str. 301 | GCF_000006925.2 |
| Q | sen | Z54211.1 | 228 | 1925 | − | CAA90938.1 | Shigella flexneri | N/A |
| | sen | CELV01000168.1 | 436 | 2133 | − | CEP59611.1 | Shigella flexneri 2a | GCA_001078805.1 |
| R | virG/icsA | AF386526.1 | 149644 | 152952 | + | AAL72293.1 | Shigella flexneri 2a str. 301 | GCA_000006925.2 |
| | virG/icsA | CP001384.1 | 148306 | 151614 | + | ADA76922.1 | Shigella flexneri 2002017 | GCA_000022245.1 |

TABLE 2-continued

Deleted Virulence Genes from Exemplary Live Vaccine Strains

| Exemplary Sequences | Virulence Gene | Nucleotide Accession | Start | Stop | Strand | Protein | Organism | Assembly |
|---|---|---|---|---|---|---|---|---|
| | virG/icsA | CP012138.1 | 69094 | 72402 | + | AMN60991.1 | Shigella flexneri 2a | GCA_001580175.1 |
| | virG/icsA | CP012142.1 | 146971 | 150279 | + | AMN66151.1 | Shigella flexneri 4c | GCA_001579965.1 |
| | virG/icsA | CELV01000134.1 | 745 | 4053 | − | CEP59383.1 | Shigella flexneri 2a | GCA_001078805.1 |
| S | luc | CP012137.1 | 3863156 | 3864880 | + | AMN59975.1 | Shigella flexneri 2a | GCA_001580175.1 |
| | luc | CP012140.1 | 3884571 | 3886295 | + | AMN64802.1 | Shigella flexneri 4c | GCA_001579965.1 |
| | luc | CELV01000103.1 | 2191 | 3915 | + | CEP59060.1 | Shigella flexneri 2a | GCA_001078805.1 |
| | luc | ADUV01000056.1 | 8414 | 10138 | − | EFS11898.1 | Shigella flexneri 2a str. 2457T | GCA_000183785.2 |
| | luc | AFHA01000080.1 | 89681 | 91405 | − | EGJ80976.1 | Shigella flexneri K-671 | GCA_000213435.2 |
| T | aroA | AE005674.2 | 941164 | 942447 | + | AAN42533.1 | Shigella flexneri 2a str. 301 | GCA_000006925.2 |
| | aroA | AE014073.1 | 945133 | 946416 | + | AAP16419.1 | Shigella flexneri 2a str. 2457T | GCA_000007405.1 |
| | aroA | CP000266.1 | 948101 | 949384 | + | ABF03130.1 | Shigella flexneri 5 str. 8401 | GCA_000013585.1 |
| | aroA | CP001383.1 | 950854 | 952137 | + | ADA73251.1 | Shigella flexneri 2002017 | GCA_000022245.1 |
| | aroA | CP004057.1 | 937946 | 939229 | + | AIL39820.1 | Shigella flexneri Shi06HN006 | GCA_000743995.1 |
| U | msbB2 | NC_002698.1 | 186010 | 186954 | + | WP_004996485.1 | Shigella flexneri 5a str. M9OT | (not assembled) |
| | msbB2 | NC_004851.1 | 194662 | 195606 | + | WP_004996485.1 | Shigella flexneri 2a str. 301 | GCF_000006925.2 |
| | msbB2 | NC_007607.1 | 89045 | 89989 | + | WP_004996485.1 | Shigella dysenteriae Sd197 | GCF_000012005.1 |
| | msbB2 | NC_019197.1 | 60218 | 61162 | − | WP_004996485.1 | Shigella flexneri | (not assembled) |
| | msbB2 | NZ_AMJQ01000012.1 | 6035 | 6979 | + | WP_004996485.1 | Shigella dysenteriae S6205 | GCF_000815495.1 |
| V | sbcA | NZ_LRRZ01000024.1 | 29025 | 29972 | + | WP_000691354.1 | Shigella sonnei | GCF_001689325.1 |
| | sbcA | CP021144.1 | 168684 | 169631 | + | ARR38645.1 | Shigella sonnei | GCA_002142635.1 |
| | sbcA | CP019689.1 | 4375543 | 4376490 | + | ARS08249.1 | Shigella sonnei | GCA_002150905.1 |
| | sbcA | AJ132761.1 | 94 | 1041 | + | CAA10763.1 | Shigella sonnei | (not assembled) |
| | sbcA | LRSA01000144.1 | 17112 | 18059 | − | OCC38201.1 | Shigella sonnei | GCA_001688545.1 |
| W | stxB | CP021144.1 | 169641 | 169910 | + | ARR38646.1 | Shigella sonnei | GCA_002142635.1 |
| | stxB | CP019689.1 | 4376500 | 4376769 | + | ARS08250.1 | Shigella sonnei | GCA_002150905.1 |
| | stxB | AJ132761.1 | 1051 | 1320 | + | CAA10764.1 | Shigella sonnei | (not assembled) |
| | stxB | LRSA01000144.1 | 16833 | 17102 | − | OCC38200.1 | Shigella sonnei | GCA_001688545.1 |
| | stxB | LRSB01000051.1 | 16789 | 17058 | − | OCC40513.1 | Shigella sonnei | GCA_001688555.1 |
| X | ampG | CP010323.1 | 51278 | 52489 | + | AJB24935.1 | Bordetella pertussis 137 | GCA_000812165.1 |
| | ampG | HE965805.1 | 3509999 | 3511210 | − | CCJ64643.1 | Bordetella pertussis 18323 | GCA_000306945.1 |
| | ampG | AXSU02000044.1 | 5852 | 7063 | + | ETH01795.1 | Bordetella pertussis 2250905 | GCA_000479635.2 |
| | ampG | AXST02000095.1 | 150 | 1361 | + | ETH04444.1 | Bordetella pertussis 2356847 | GCA_000479655.2 |
| | ampG | AXSS02000025.1 | 156 | 1367 | + | ETH09488.1 | Bordetella pertussis 2371640 | GCA_000479735.2 |
| Y | dnt | NZ_NXFD01000089.1 | 8703 | 13097 | − | WP_010931478.1 | Bordetella pertussis | GCF_002406875.1 |
|

TABLE 2-continued

Deleted Virulence Genes from Exemplary Live Vaccine Strains

| Exemplary Sequences | Virulence Gene | Nucleotide Accession | Start | Stop | Strand | Protein | Organism | Assembly |
|---|---|---|---|---|---|---|---|---|
| | dnt | NZ_CFWW01000036.1 | 2110 | 6504 | + | WP_010931478.1 | Bordetella pertussis | GCF_001333495.1 |
| Z | aroA | NC_002929.2 | 986558 | 987886 | + | WP_010930099.1 | Bordetella pertussis Tohama I | GCF_000195715.1 |
| | aroA | NC_017223.1 | 1010147 | 1011475 | + | WP_010930099.1 | Bordetella pertussis CS | GCF_000212975.1 |
| | aroA | NC_018518.1 | 1405318 | 1406646 | + | WP_010930099.1 | Bordetella pertussis 18323 | GCF_000306945.1 |
| | aroA | NZ_ADKR01000103.1 | 10731 | 12059 | + | WP_010930099.1 | Bordetella pertussis B0558 | GCF_000193515.1 |
| | aroA | NZ_ADKS01000376.1 | 10733 | 12061 | + | WP_010930099.1 | Bordetella pertussis B1193 | GCF_000193535.1 |
| AA | aroQ | NC_002927.3 | 4677939 | 4678373 | − | WP_003814953.1 | Bordetella bronchiseptica RB50 | GCF_000195675.1 |
| | aroQ | NC_002928.3 | 4243092 | 4243526 | − | WP_003814953.1 | Bordetella parapertussis 12822 | GCF_000195695.1 |
| | aroQ | NC_002929.2 | 3189581 | 3190015 | − | WP_003814953.1 | Bordetella pertussis Tohama I | GCF_000195715.1 |
| | aroQ | NC_017223.1 | 3229800 | 3230234 | − | WP_003814953.1 | Bordetella pertussis CS | GCF_000212975.1 |
| | aroQ | NC_018518.1 | 3117828 | 3118262 | − | WP_003814953.1 | Bordetella pertussis 18323 | GCF_000306945.1 |
| BB | tcdA | AM180355.1 | 795843 | 803975 | + | CAJ67494.1 | Clostridioides difficile 630 | GCA_000009205.2 |
| | tcdA | FULU01000004.1 | 183105 | 191237 | + | SJ024242.1 | Clostridioides difficile VRECD0137 | GCA_900164045.1 |
| | tcdA | FUMVV01000003.1 | 126069 | 134201 | + | SJP00148.1 | Clostridioides difficile VRECD0039 | GCA_900164375.1 |
| | tcdA | FUOD01000003.1 | 183261 | 191393 | + | SJQ51066.1 | Clostridioides difficile VRECD0053 | GCA_900164815.1 |
| | tcdA | FUOR01000003.1 | 408706 | 416838 | − | SJQ80390.1 | Clostridioides difficile VRECD0100 | GCA_900164945.1 |
| CC | tcdB | AM180355.1 | 787393 | 794493 | + | CAJ67492.1 | Clostridioides difficile 630 | GCA_000009205.2 |
| | tcdB | AVGL01000018.1 | 25017 | 32117 | + | EQE11947.1 | Clostridioides difficile CD13 | GCA_000448885.2 |
| | tcdB | AVIE01000188.1 | 409 | 7509 | + | EQF85571.1 | Clostridioides difficile CD196 | GCA_000449605.2 |
| | tcdB | AVLC01000039.1 | 15891 | 22991 | + | EQI61286.1 | Clostridioides difficile Y266 | GCA_000451185.2 |
| | tcdB | AVMNO1000011.1 | 46819 | 53919 | + | EQJ95904.1 | Clostridioides difficile P49 | GCA_000451945.2 |

Methods of Use

A further aspect encompasses methods of using a genetically engineered bacterium provided herein (e.g., a genetically engineered *V. cholerae* bacterium). For instance, in some embodiments provided herein are methods for modulating a subject's immune system by administering a genetically engineered described herein to the subject (e.g., orally). The method includes administering to the subject (e.g., a human subject) an effective amount of a composition comprising a genetically engineered bacterium described herein. One of skill in the art will appreciate that an effective amount of a composition is an amount that will generate the desired response (e.g., a protective response, a mucosal response, a humoral response, or a cellular response). The response can be quantitated by methods known in the art.

In some embodiments, provided herein are methods of inducing a protective response against a virulent strain of *Vibrio cholerae* in a subject, the method comprising administering a genetically modified *V. cholerae* bacterium described herein, or a pharmaceutical composition comprising a genetically modified *V. cholerae* bacterium described herein. In some embodiments, the protective response is developed within about 12 hours, about 18 hours, about 24 hours, about 36 hours, about 48 hours, about 60 hours, about 72 hours, or about 84 hours after administration of the genetically modified bacterium of the pharmaceutical composition to the subject. In some embodiments, the protective immune response is developed within 12 hours, 18 hours, 24 hours, 36 hours, 48 hours, 60 hours, 72 hours, 84 hours, or more after administration of the genetically modified bacterium of the pharmaceutical composition to the subject.

In a further embodiment, the genetically engineered *V. cholerae* bacteria described herein may be used in a method for ameliorating one or more symptoms of cholera in a host in need thereof. Cholera symptoms include diarrhea, nausea, vomiting, and dehydration. The method includes administering an effective amount of a composition comprising a genetically engineered *V. cholerae* bacterium described herein.

The genetically engineered bacteria described herein and compositions comprising the bacteria may be administered to any subject. Exemplary vaccine composition formulations comprising the genetically engineered bacteria and methods of administration are detailed below.

Pharmaceutical Compositions

Pharmaceutical compositions comprising a genetically engineered bacterium described herein may optionally comprise one or more possible pharmaceutically acceptable excipients, such as carriers, preservatives, cryoprotectants (e.g., sucrose and trehalose), stabilizers, adjuvants, and other substances. For example, when the composition includes genetically engineered bacteria that are alive, excipients are chosen such that the live bacterium is not killed, or such that the ability of the bacteria to effectively colonize a subject is not compromised by the use of excipients. Suitable pharmaceutical carriers are known in the art and, for example, include liquid carriers, such as normal saline and other non-toxic salts at or near physiological concentrations, and solid carriers, such as talc and sucrose. In some embodiments, the pharmaceutical composition includes an adjuvant. In some embodiments, the pharmaceutical composition may be a in a form suitable for aerosolized administration to a subject. In some embodiments, the pharmaceutical formulation is in a freeze-dried form (i.e., lyophilized form). In some embodiments, the pharmaceutical formulation is a gelatin capsule. Suitable pharmaceutical carriers and adjuvants and the preparation of dosage forms are described in, *Remington's Pharmaceutical Sciences*, 17th Edition, (Gennaro, Ed., Mack Publishing Co., Easton, Pa., 1985), which is herein incorporated by reference.

Administration of the genetically engineered bacteria described herein to a subject can be by any known technique, including, but not limited to oral administration, rectal administration, vaginal administration, or nasal administration.

The dosages of the genetically engineered bacteria that is administered to a subject can and will vary depending on the genetically engineered bacterium, the route of administration, and the intended subject, as will be appreciated by one of skill in the art. Generally speaking, the dosage need only be sufficient to elicit a protective host response in the subject. For example, typical dosages for oral administration could be about $1 \times 10^7$ to $1 \times 10^{10}$ colony forming units (CFU) depending upon the age of the subject to whom the bacteria will be administered. Administering multiple dosages of the genetically engineered bacteria may also be used as needed to provide the desired level of protection.

Kits comprising a genetically engineered bacterium or a pharmaceutical composition described herein are also provided. In some embodiments, the kit further includes instructions for use. In some embodiments, the pharmaceutical composition is lyophilized such that addition of a hydrating agent (e.g., buffered saline) reconstitutes the composition to generate a pharmaceutical composition suitable for administration to a subject (e.g., orally).

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The invention is further described in the following examples, which do not limit the scope of the invention described in the claims.

Example 1. A Genetically Engineered *Vibrio cholerae* Bacterial Strain Confers Resistance Against Virulent Strains of *V. cholerae* within One Day of Administration The massive and ongoing cholera epidemics in Yemen and Haiti illustrate that this ancient diarrheal disease remains a significant threat to public health (Balakrishnan (2017) *Lancet Infect. Dis.* 17, 700-1; and Ali et al. (2015) *PLoS Negl. Trop Dis.* 9, e0003832). Cholera results from ingesting water or food contaminated by *Vibrio cholerae*, a Gram-negative bacterial pathogen. *V. cholerae* colonizes the small intestine where it produces cholera toxin, which induces profuse watery diarrhea and consequent dehydration that can be rapidly fatal in the absence of rehydration therapy (Clemens et al. (2017) *Lancet* 390(10101): 1539-49). Public health interventions to limit cholera dissemination are critical because of the otherwise rampant spread of cholera epidemics, particularly in association with disruptions in sanitation infrastructure and water supplies. Oral cholera vaccines (OCVs) consisting of killed whole *V. cholerae* cells have modest protective efficacy in endemic regions (Qadri et al. (2015) *Lancet* 386(10001): 1362-71), and these vaccines were recently deployed during outbreaks in non-endemic areas as part of 'reactive vaccination' programs aimed at blocking the spread of cholera (see, e.g., Luquero et al. (2014) *N. Engl. J. Med.* 370(22): 2111-20). However, optimal efficacy of killed OCVs requires 2 refrigerated doses administered 14 days apart (see, e.g., Kabir (2014) *Clin. Vaccine Immunol.* 21(9): 1195-1205), and these features may limit the capacity of the killed OCVs to rapidly constrain ongoing outbreaks in destabilized or resource-limited settings. Single dose live attenuated OCVs showed efficacy in challenge studies (see e.g., Chen et al. (2016) *Clin. Infect. Dis.* 62(11): 1329-35) and early phase clinical trials in endemic regions (Qadri et al. (2007) *Vaccine* 25(2): 231-8), and reactive vaccination with a live attenuated OCV may have contributed to a decrease in the incidence of cholera during an outbreak (see Calain et al. (2004) *Vaccine* 22(19): 2444-51). However, no live OCVs are based on globally predominant 'variant' El Tor strains, like that responsible for the 2010 Haitian cholera outbreak (see Chin et al. (2011) *N. Engl. J. Med.* 364(1): 33-42). Furthermore, no killed or live attenuated OCV has been shown to mediate rapid (e.g., within 24 hours of administration) protection against cholera; instead current vaccines are thought to require the time necessary to elicit a protective adaptive immune response (a minimum of 1 week), to engender protection against cholera. This example describes the generation of a new live attenuated cholera vaccine based on the Haitian outbreak strain which was found to rapidly protect infant rabbits against lethal cholera-like illness within one day of administration.

Materials and Methods

The following materials and methods were used in this Example.

Study Design

The aim of this study was to design a new live attenuated cholera vaccine candidate, assess the strain's capacity to safely colonize the intestine, determine whether the strain could protect animals from cholera-like illness shortly after its administration, and quantify the potential impact of observed protection parameters on the incidence of cholera infection during an epidemic. The vaccine candidate was derived, from an isolate of the globally predominant *V. cholerae* strain, via sequential allelic exchange steps (see Genetic manipulations), and mutations were verified by whole genome sequencing (see Whole genome sequencing). Studies of intestinal colonization and cholera-like illness were conducted, in compliance with federal and institutional guidelines regarding the use of animals in research, using the infant rabbit model of infection (see Infant rabbit infection studies). 1-2 day old animals were allocated to treatment groups randomly, and within-litter (i.e., co-housed and age-matched) controls were used to minimize the impacts of litter-to-litter variation. For studies of disease progression, assessors were unaware of the treatment administered to each group, and animals found dead within 10 hours of challenge were excluded due to physical trauma consistent with maternal rejection. Transposon-insertion sequencing studies were conducted using the ARTIST pipeline, which models and compensates for experimental noise and offers recommendations for the imposition of effect size thresholds (see Transposon-insertion sequencing analysis). Lastly, modeling incorporating a variable time to vaccine protection into a set of previously published parameters for disease transmission was performed (see Modeling of cholera outbreaks).

Statistical Analysis

Comparisons of two samples were performed using two-sided testing ($\alpha=0.05$) for a t test (fluid accumulation ratios), a Mann-Whitney U test for nonparametric data (bacterial burden), or a log-rank test (survival curve). Comparisons of three samples were performed using the Kruskall-Wallis test followed by Dunn's multiple comparisons test (bacterial burden).

Strains, Media, and Culture Conditions

Table 3 contains a list of strains used in this study. Unless otherwise noted, *V. cholerae* and *E. coli* were grown in lysogeny broth (LB: 10 g/L tryptone, 5 g/L yeast extract, 5 g/L NaCl) with shaking (250 RPM) at 37° C. Recipient strains in phage transduction assays were grown in AKI media (15 g/L peptone, 4 g/L yeast extract, 5 g/L NaCl, autoclaved, then supplemented with freshly made, sterile-filtered 0.3% $NaHCO_3$).

Antibiotics and substrates were used in the following concentrations unless otherwise noted: streptomycin (Sm) (200 μg/mL), carbenicillin (50 μg/mL), chloramphenicol (20 μg/mL), SXT (160 μg/mL sulfamethoxazole, 32 μg/mL trimethoprim), kanamycin (Kn) (50 μg/mL) and 5-Bromo-4-Chloro-3-Indolyl β-D-Galactopyranoside (X-Gal 60 mg/mL).

TABLE 3

Strains and plasmids used in this study

| Strain Identifier | Species | Strain | Plasmid | Resistance | Source |
|---|---|---|---|---|---|
| GB5 | *V. cholerae* | N16961 | | Sm | (10) |
| MKW1161 | *V. cholerae* | Haiti isolate#1-H1 (HaitiWT) | | SXT | (10) |
| MKW1866 | *V. cholerae* | Haiti Δctx | | SXT | This study |
| MKW1867 | *V. cholerae* | Haiti ΔctxΔflaBDE | | SXT | This study |
| MKW1908 | *V. cholerae* | Haiti Δctx ΔflaABCDE | | SXT | This study |
| MKW2156 | *V. cholerae* | Haiti Δctx ΔflaABCDE ΔdfrA ΔfloR ΔstreAB Δsul2 | | | This study |
| MKW2158 | *V. cholerae* | Haiti Δctx ΔflaABCDE ΔdfrA ΔfloR ΔstreAB Δsul2 N900_11550::PhtpG-ctxB | | | This study |
| MKW2159 | *V. cholerae* | Haiti Δctx ΔflaABCDE ΔdfrA ΔfloR ΔstreAB Δsul2 N900_11550::PhtpG-ctxB | | Sm | This study |
| MKW2174 | *V. cholerae* | Haiti Δctx ΔflaABCDE ΔdfrA ΔfloR ΔstreAB Δsul2 N900_11550::PhtpG-ctxB ΔhupB | | Sm | This study |
| GB79 | *V. cholerae* | Haiti Δctx ΔflaABCDE ΔdfrA ΔfloR ΔstreAB Δsul2 N900_11550::PhtpG-ctxB ΔhupB lacZ::cas9-sgRNA ctxA | | Sm | This study |

TABLE 3-continued

Strains and plasmids used in this study

| Strain Identifier | Species | Strain | Plasmid | Resistance | Source |
|---|---|---|---|---|---|
| GB82 | V. cholerae | Haiti Δctx ΔflaABCDE ΔdfrA ΔfloR ΔstreAB Δsul2 N900_11550::PhtpG-ctxB ΔhupB lacZ::cas9-sgRNA_ctxA ΔrecA (HaitiV) | | Sm | This study |
| | E. coli | Dh5alpha λpir | | | |
| | E. coli | MFD λpir | | | (31) |
| | E. coli | | pRK600 | Chlor | |
| MKW1865 | E. coli | MFD λpir | pCVD442 Δctx (HAITI) | Carb | This study |
| MKW1909 | E. coli | MFD λpir | pCVD442 ΔflaAC(Haiti) | Carb | This study |
| YM82 | E. coli | SM10λir | pCVD ΔflaBDE | Carb | (32) |
| MKW2241 | E. coli | MFD λpir | pCVD442 ΔdfrA | Carb | This study |
| MKW2240 | E. coli | MFD λpir | pCVD442 ΔfloR-strAB-sul2 | Carb | This study |
| FD25 | E. coli | MFD λpir | pCVD442 N900_11550::Phtpg-ctxB | Carb | This study |
| MKW2168 | E. coli | MFD λpir | pCVD442 ΔhupB | Carb | This study |
| GB50 | E. coli | Dh5alpha λpir | pJL1 lacZ::cas9-sgRNA_ctxA | Carb | This study |
| MKW2167 | E. coli | MFD λpir | pCVD442 ΔrecA | Carb | This study |
| | E. coli | SM10λir | pCVD442 ΔcqsS | Carb | This study |
| | E. coli | SM10λir | pJL1 | Carb | (34) |
| | E. coli | SM10λir | pSC189 | Carb | (36) |

Genetic Manipulations

All gene deletions and replacements were constructed via homologous recombination using the suicide vector pCVD442, DH5α-λpir and donor strains MFD-λpir (see Ferrieres et al. (2010) J. Bacteria 192(24): 6418-27) or SM10-λpir (Table 3). For all deletions, approximately 500-700 bp homology regions upstream and downstream of the respective ORF were amplified using the primer combinations described below and cloned into XbaI-digested pCVD442 using isothermal assembly.

For derivation of HaitiV from the HaitiWT strain, first, the CTXΦ prophage and surrounding sequences were deleted using primers TDPsCTX1/TDPsCTX2 and TDPsCTX3/TDPsCTX4 to amplify homology regions upstream of the rtx toxin transporter at the 5' end and upstream of a putative dehydrogenase on the 3' end of this region. This results in a deletion of a 42,650 bp fragment that includes the entire CTXΦ prophage, which includes ctxAB, the CTX attachment site, the RS1 and TLC satellite prophages and the MARTX toxin genes rtxABCDE. The knockout was validated via polymerase chain reaction (PCR) using primers TD1027/TDP1028.

Next, the flaBDE operon was deleted as previously described in Millet et al. (2014) PLoS Pathog. 10(10): e1004405. The flaAC operon deletion plasmid was constructed using primers TDP1172/1174 (upstream homology) and TDP1173a/TDP1173 (downstream homology). Subsequently, the SXT ICE-encoded antibiotic resistance loci, dfrA, sul2, strAB, and floR were deleted using primers TDP1193/TDP1194+TDP1195/1196 (dfrA, trimethoprim resistance) and TDP1287/TDP1288+TDP1291/TDP1292 (sulfamethoxazole, streptomycin and chloramphenicol resistance loci). Whole genome sequencing revealed that the second crossover in the allele exchange process occurred not between the homologous regions included in the suicide plasmid, but rather between duplicate sequences flanking the flor/sul region of the chromosome (N900_11210 and N900_11260). An $Sm^R$ mutant of the vaccine precursor strain was isolated by plating on streptomycin (1000 μg/mL), and the $rpsL^{K43R}$ SNV was confirmed by Sanger sequencing.

Figure 7:
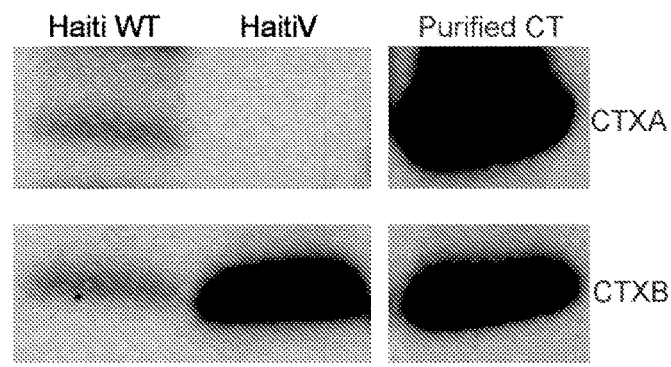
Figure 8A:
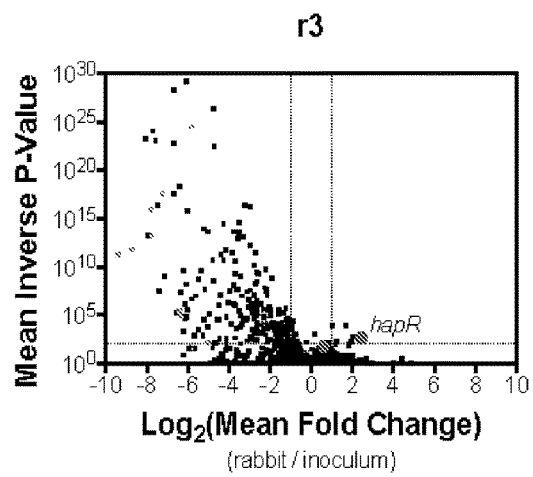
Figure 8B:
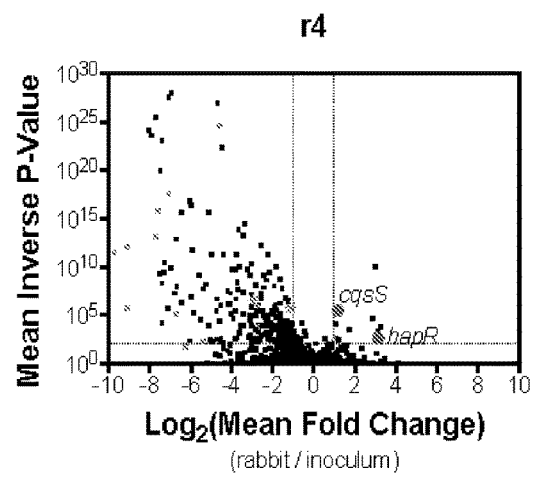
Figure 8C:
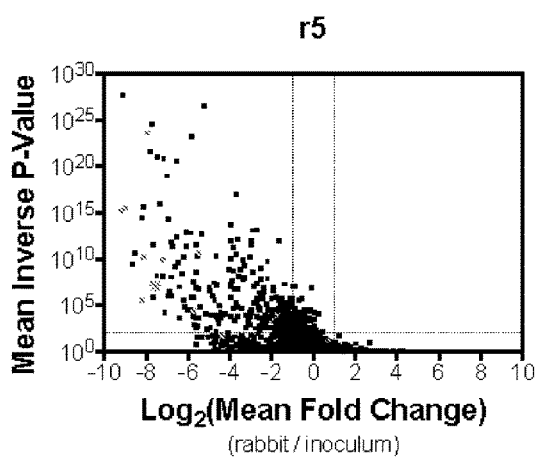
Figure 8D:
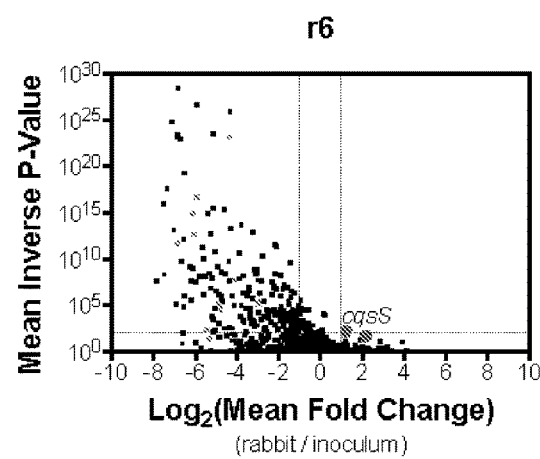
Figure 9A:
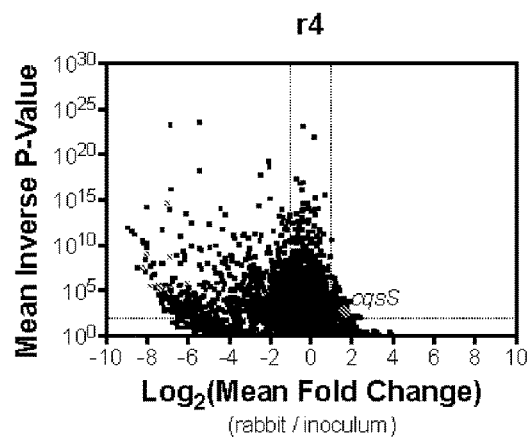
Figure 9B:
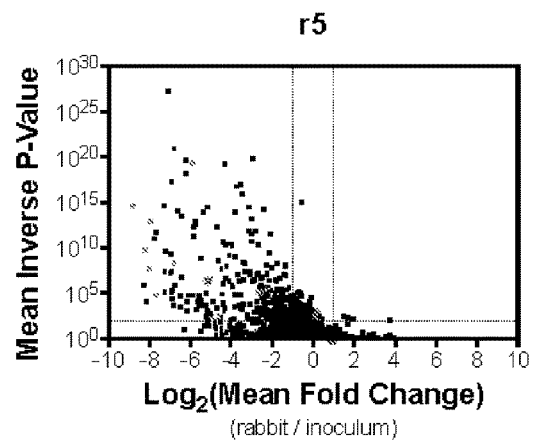
Figure 9C:
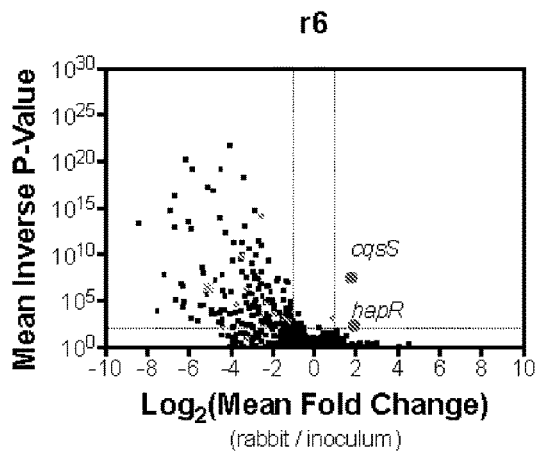
Figure 9D:
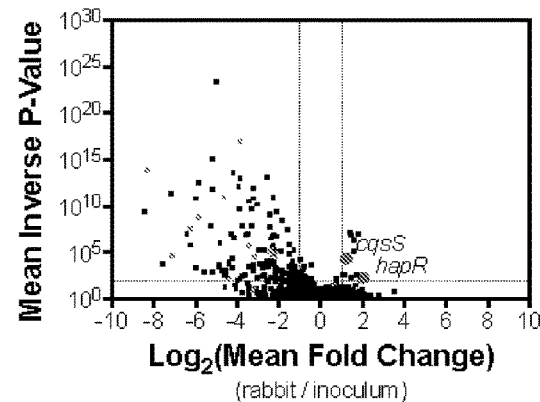

For CtxB overexpression, the htpG promoter was amplified from Peru-15 (see Kenner et al. (1995) J. Infect. Dis. 172(4): 1126-9) using primers FD54/FD103 (adding the strong ribosome binding site AGGAGG (SEQ ID NO: 6)) and ctxB was amplified from HaitiWT, which contains the ctxB7 allele, using primers FD33/FD34. Homologous regions flanking the intergenic region of the validated neutral locus vc0610/N900_11550 (see Abel et al. (2015) Nat. Methods 12(3): 223-6) were amplified with primer pairs FD30/FD31 and FD73/FD74. These fragments were then cloned into pCVD442 in a one-step isothermal assembly reaction. CtxB overexpression was confirmed by Western blot on cell-free supernatants from cultures grown in AKI conditions described above. (Abcam ab123129, anti-cholera toxin; FIG. 7).

Next, the hupB deletion plasmid was constructed using primer pairs Vc-hupB5-F1/Vc-hupB5-R1 and VC-hupB3-F1/Vc-hupB3-R1. The deletion was verified with primers VC-hupB-SF2/Bc-hupB-SR2.

For the cas9-sgRNA module, cas9 was amplified from plasmid DS_SpCas9 (addgene.org/48645/) with primers TDP1747/TDP1748. The sgRNA region was amplified from gBlock 'VC_3x_sgRNA_gBlock' (Table 4) with primers TDP1761/TDP1762. Both fragments were combined and cloned in to the StuI site of pJL1 (Butterton (1995) Infect

*Immun* 63: 2689-96) via isothermal assembly. Sequencing revealed that a recombination event during assembly had removed 2 of 3 sgRNAs, leaving a single guide targeting ctxA. This suicide vector was introduced to the vaccine strain via triparental mating with the helper plasmid pRK600.

TABLE 4

Oligonucleotides used in this study

| Primer number | Primer name | Sequence |
|---|---|---|
| | CTX | |
| TDPsCTX 1 | ctxAfwpCVD | AGGTATATGTGATGGGTTAAAAAGGATCGATCCTTG CTCTCTTGTAGTACCACACTCATAT (SEQ ID NO: 8) |
| TDPsCTX 2 | ctxArev | TCATCATTATTACTCGAGTGCGGCCGCATTACGACGT TTTTGACCGAAGCCG (SEQ ID NO: 9) |
| TDPsCTX 3 | ctxAfw | TAATGCGGCCGCACTCGAGTAATAATGATGAGCTCA ACATTACTCGCCTCAAAAACT (SEQ ID NO: 10) |
| TDPsCTX 4 | ctxArevpCVD | CCGGGAGAGCTCGATATCGCATGCGGTACCTCTAGG CGATCAGAGCCAAGCGTAAG (SEQ ID NO: 11) |
| TDP1027 | ctxAHaitifw | AAGCCGTGGGGAAGTCCTTC (SEQ ID NO: 12) |
| TDP1028 | ctxAHaitirev | CGCTGTCACTGTATAACAATGGAAAGTG (SEQ ID NO: 13) |
| | flaAC | |
| TDP1172 | FlaACfw3rdpCVD | AGGTATATGTGATGGGTTAAAAAGGATCGATCCTAC CTGCCATTACATCGATGATTTGAGC (SEQ ID NO: 14) |
| TDP1173 | FlaAcrev3rdpCVD | CCGGGAGAGCTCGATATCGCATGCGGTACCTCTAGC ATCAAGTTCTGTTCTCGCACAAGC SEQ ID NO: 15) |
| TDP1173a | flaACfw | TAATGCGGCCGCACTCGAGTAATAATGATGATCGCT CATATGGCTTAAGCGCAT (SEQ ID NO: 16) |
| TDP1174 | FlaAcrev3rdLINK | TCATCATTATTACTCGAGTGCGGCCGCATTACATCAA GTTCTGTTCTCGCACAAGC (SEQ ID NO: 17) |
| | dfrA/trim | |
| TDP1193 | trimfwpCVD | AGGTATATGTGATGGGTTAAAAAGGATCGATCCTTT TACAGCCTGACTAGGTTCTTGCTC (SEQ ID NO: 18) |
| TDP1194 | trimrev | TTATCATGCGGCCGCACTCGAGTAATGATAAGCGGA GCTTAACTCAGTGGGG (SEQ ID NO: 19) |
| TDP1195 | trimdwnFW | TTATCATTACTCGAGTGCGGCCGCATGATAAAGTTAT TATGTAGACCTCTCAGTAACATCCG (SEQ ID NO: 20) |
| TDP1196 | trimrevpCVD | CCGGGAGAGCTCGATATCGCATGCGGTACCTCTAGA AGACGATAGCGCAAAGCGC (SEQ ID NO: 21) |
| | sul2/strAB/floR | |
| TDP1287 | florfwpCVD | AGGTATATGTGATGGGTTAAAAAGGATCGATCCTCA ACCGGCTTCGGGCAAC (SEQ ID NO: 22) |
| TDP1288 | florrev | TTATCATTACTCGAGTGCGGCCGCATGATAAATTAA GGAATACCGGGCGACGT (SEQ ID NO: 23) |
| TDP1291 | sulfafw2 | TTATCATTACTCGAGTGCGGCCGCATGATAAGATGC CGAAAATGATGAGCGATTTATTCAT (SEQ ID NO: 24) |
| TDP1292 | sulfarevpCVD2 | CCGGGAGAGCTCGATATCGCATGCGGTACCTCTAGT GAGAATAGTAATTTCGTTTTTGATGGCCAT (SEQ ID NO: 25) |
| | ctxB Overexpression | |
| FD54 | hptGpromfw | ATCTCTTTTGAGTTGTGTCCTAATC (SEQ ID NO: 26) |
| FD103 | re_htpGrev_RBS_ ctxB | AAAACACCAAATTTTAATTTAATCATGGACGTCCTCC TATTCAGCCGTACCCGATTTAGCA (SEQ ID NO: 27) |
| FD33 | newctxBfw | ATGATTAAATTAAAATTTGGTGTTTTTTTTACAGTTT TACTATCTTCAG (SEQ ID NO: 28) |
| FD34 | 2ndctxBrev0610 down | GCAATCCAAGACGCTTGGTGAGAGTTAATTTGCCAT ACTAATTGCGGCAATC (SEQ ID NO: 29) |
| FD30 | new0610downfw | CTCTCACCAAGCGTCTTGGATTGC (SEQ ID NO: 30) |
| FD31 | 0610downrevpCVD | CCGGGAGAGCTCGATATCGCATGCGGTACCTCTAGG GCGTGTTCGCTTCTAGCCTATTGG (SEQ ID NO: 31) |
| FD73 | pCVDfwmid0610 | AGGTATATGTGATGGGTTAAAAAGGATCGATCCTAT GAGCCGTTTTCCAATATCGATACTCAAG (SEQ ID NO: 32) |
| FD74 | vc0610preSTOPrev htpG | GATTAGGACACAACTCAAAAGAGATGGCGAAAGCG AGCACGC (SEQ ID NO: 33) |
| | hupB | |
| | Vc_hupB5-F1 | AGGTATATGTGATGGGTTAAAAAGGATCGATCCTAA GTGCGGGTATCGCCATGTGTAC (SEQ ID NO: 34) |

TABLE 4-continued

Oligonucleotides used in this study

| Primer number | Primer name | Sequence |
|---|---|---|
| | Vc_hupB5-R1 | GCAGAAAAGTGCAAAATCTTCATTCAAATGTGATTC CCCTTTGGTCACCCTT (SEQ ID NO: 35) |
| | Vc_hupB3-F1 | AAGGGTGACCAAAGGGGAATCACATTTGAATGAAG ATTTTGCACTTTTCTGC (SEQ ID NO: 36) |
| | Vc_hupB3-R1 | GGAGAGCTCGATATCGCATGCGGTACCTCTAGCAAT TGACGAACTTGCTCATCACT (SEQ ID NO: 37) |
| | Vc-hupB-SF2 | GTTGCCTTGGAGCAAGACCC (SEQ ID NO: 38) |
| | Vc-hupB-SR2 | CGATGCTGTTCACGCCTTCG (SEQ ID NO: 39) | cas9-sgRNA_ctxA

| Primer number | Primer name | Sequence |
|---|---|---|
| TDP1747 | Cas9fwpJL1 | GTGATGATTGGTACCAGATCTTAATTAAGGTGCAGG AAGCAACGGCCC (SEQ ID NO: 40) |
| TDP1748 | Cas9rev | TCAGTCACCTCCTAGCTGACTCAAATC (SEQ ID NO: 41) |
| TDP1761 | gblockfwCas9 | CACGCATTGATTTGAGTCAGCTAGGAGGTGACTGAA AGAGGAGAAAGGATCTATCGACCAC (SEQ ID NO: 42) |
| TDP1762 | gBlockrevpJL1 | CGGGGATTGGTACCGCGGCCGCTCTAGAGGTGAGG GCTGAACCTCTTTGCA (SEQ ID NO: 43) |
| | VC_3x_sgRNA_gBlock' | AAGAGGAGAAAGGATCTATCGACCACTACCTCGACC CTGATGAAATAAAGCAGTCGTTTTAGAGCTAGAAAT AGCAAGTTAAAATAAGGCTAGTCCGTTATCAACTTG AAAAAGTGGCACCGAGTCGGTGCAAAAAGAGTATT GACTTAAAGTCTAACCTATAGGCATAATTATTTCATC ACTATTTTTGTCGATTATCTTGCTGTTCTAGAGAGCG GGAGCTCAAGTTAGAATAAGGCTAGTCCGTATTCAG TGCGGGAGCACGGCACCGATTCGGTGCAAAAAATTT ATTTGCTTTTTATCCCTTGCGGCGATATAATGTGTGG ATAGAACTAAACAAAGGGAGCATTATAGTTGGAGA GGCATGAGAATGCCAAGTTCCAATAAGGCTAGTCCG TACACACCTAGGAGACTAGGGGCACCGAGTCGGTGC TCGGCAGGCTGAATGCAAAGAGGTTCAGCCTCTCA (SEQ ID NO: 44) | recA

| Primer number | Primer name | Sequence |
|---|---|---|
| | Vc_recA5-F1 | AGGTATATGTGATGGGTTAAAAAGGATCGATCCTGT GACACAATGAAACAGAAGCGAG (SEQ ID NO: 45) |
| | Vc_recA5-R1 | CTTTGCATTCAGCCTGCCGAGTGATAGGTAATTGTGT CGAAATCGG (SEQ ID NO: 46) |
| | Vc_recA3-F1 | CCGATTTCGACACAATTACCTATCACTCGGCAGGCT GAATGCAAAG (SEQ ID NO: 47) |
| | Vc_recA3-R1 | CCGGGAGAGCTCGATATCGCATGCGGTACCTCTAGT CTCTTCCGCAAACTGAATGTGTG (SEQ ID NO: 48) |
| | Vc-recA-SF2 | TGAGCATCTCGCAGCAGATC (SEQ ID NO: 49) |
| | Vc-recA-SR2 | GTTGTAAGGCACTTTGTCGGC (SEQ ID NO: 50) |

Finally, a recA deletion plasmid was constructed using primer pairs Vc-recA5-F1/Vc-recA5-R1 and Vc-recA3-F1/Vc-recA3-R1; the deletion was verified with primers Vc-recA-SF2/Vc-recA-SR2.

Whole Genome Sequencing

Genomic DNA from HaitiWT and HaitiV was prepared using the Nextera XT library preparation kit (ILLUMINA) and sequenced on a MiSeq (Reagent kit v2, 2×250). The genomic sequence of the bacterial chromosomes of HaitiV are provided herein as SEQ ID NOs: 7 and 51. The HaitiV strain was deposited with the American Type Culture Collection (ATCC), located at 10801 University Boulevard, Manassas, Va. 20110, USA on Jun. 22, 2018 under the terms of the Budapest Treaty and assigned ATCC Patent Deposit Designation PTA-125138. Each sample was mapped to its putative genome and variants identified using GATK3.6.

CTXΦ Transduction Assay

Supernatant from *Vibrio cholerae* O395 strains harboring CTXΦ-IGKn (a phage whose genome includes ctxA (see, e.g., Lazar and Walder (1998) *Infect. Immun.* 66: 394-7) or CTX-KnΦ (a phage whose genome lacks ctxA (see, e.g., Waldor and Mekalanos (1996) *Science* 272(5270): 1910-4) (grown at 30° C. in LB to an $OD_{600}$ of 1.0) was concentrated (approximately 50-fold; Ultracel-100K centrifugal filter, MILLIPORE) and filtered (0.22 μm filter, MILLIPORE) to get a cell-free phage supernatant. In order to induce expression of TCP (the phage receptor) in the strains being assayed for CTXΦ susceptibility, overnight LB cultures were back-diluted 1:100 into 10 mL AKI in 16×150 mm glass culture tubes and incubated without shaking for 4 hours at 37° C. All but 1 mL of the culture was then discarded, and the culture was moved to a shaker (250 rpm) for aerobic culture at 37° C. for an additional 2 hours. Recipient cultures were washed once by centrifugation, mixed 2:1 with phage supernatant, and incubated at room temperature for 20 minutes. Serial dilutions were then plated on LB and LB+Kanamycin (100 μg/mL) agar plates, and transduction efficiency was calculated as $(CFU/mL)_{Kan100}/(CFU/mL)_{LB}$.

Generation of HaitiWT-Tn Library

*E. coli* SM10λpir bearing the pir-dependent Himar transposon vector pSC189 (Chiang and Rubin (2002) *Gene* 296(1-2): 179-85) were conjugated with recipient HaitiWT to generate a transposon-insertion library. Overnight cultures of each strain were grown aerobically at 37° C. and then diluted 1:100 in media at 37° C. After 4 hours of outgrowth, 4 mL of each culture was pelleted and washed once with LB. Cultures were then mixed in a 1:1 ratio, pelleted and re-suspended in 800 µL LB. 50 µL of the mix was spotted onto 0.45 µm filters on LB agar plates for a total of 16 conjugation reactions. Reactions were incubated at 37° C. for 4 hours, after which filters were vortexed in LB (1 mL/filter) to re-suspend attached bacteria. Suspensions were plated onto 245 mm² LB+Sm/Kan agar plates to select for $V.$ $cholerae$ trans-conjugants (2 mL suspension/plate). Plates were incubated at 30° C. overnight to enumerate bacterial colonies. The library consisted of ~300,000 colonies and was scraped into LB+25% glycerol. The $OD_{600}$ was adjusted to approximately 10 and aliquots were stored at −80° C. for downstream use.

Infant Rabbit Infection Studies

Infant rabbit studies were conducted according to protocols approved by the Brigham and Women's Hospital Committee on Animals (Institutional Animal Care and Use Committee protocol number 2016N000334, Animal Welfare Assurance of Compliance number A4752-01) and in accordance with the recommendations in the Guide for the Care and Use of Laboratory Animals of the National Institutes of Health and the Animal Welfare Act of the United States Department of Agriculture.

To prepare bacteria for inoculation, overnight cultures were diluted 1:100 in 100 mL LB and cultured with aeration at 37° C. until late-log phase ($OD_{600}$ 0.5 to 0.9). Approximately $2 \times 10^{10}$ CFU were pelleted by centrifugation at 6,000 rpm, the supernatant was removed, and cell pellets were re-suspended in 10 mL of 2.5% sodium bicarbonate solution (2.5 g in 100 mL water; pH 9.0) to a final cell density of approximately $2 \times 10^9$ CFU/mL. For co-infection studies, approximately $1 \times 10^{10}$ CFU were pelleted by centrifugation at 6,000 rpm, the supernatant was removed, cell pellets were re-suspended in 5 mL 2.5% sodium bicarbonate solution, and the resulting suspensions were combined to yield a 1:1 mixture at a cell density of approximately $2 \times 10^9$ CFU/mL. For studies using the HaitiWT transposon library, a 1 mL frozen stock of the library ($OD_{600}$=10) was transferred to 100 mL LB to an initial $OD_{600}$ of 0.1. The library was then cultured with aeration at 37° C. to $OD_{600}$ 0.8 (approximately 2 hours) and approximately $2 \times 10^9$ CFU/mL cell suspension in 2.5% sodium bicarbonate solution was prepared as described above. Preparation of formalin-killed vaccine required the following additional steps: cell pellets were re-suspended in 8 mL of 10% formalin, the formalin suspension was centrifuged at 6,000 rpm, the supernatant was removed, cells were re-suspended in 5 volumes of 1× phosphate buffered saline (40 mL 1×PBS) to wash away excess formalin, the PBS suspension was centrifuged at 6,000 rpm, the supernatant was removed, and cells were re-suspended in 10 mL of 2.5% sodium bicarbonate solution. This procedure eliminated all viable $V.$ $cholerae$. For all experiments, the final cell suspension was serially diluted in 1×PBS and plated in triplicate on LB+Sm/X-Gal, and incubated at 30° C. overnight to enumerate the precise dose. For co-infection studies, the disruption of lacZ in HaitiV enabled enumeration of HaitiWT and HaitiV CFU, blue and white colonies, respectively. For studies using the HaitiWT transposon library, approximately $2 \times 10^{10}$ CFU of the library inoculum were plated on LB+Sm200/Kan50 and incubated at 30° C. overnight to generate a representative sample of the library inoculum used for subsequent statistical comparisons.

Figure 4A:
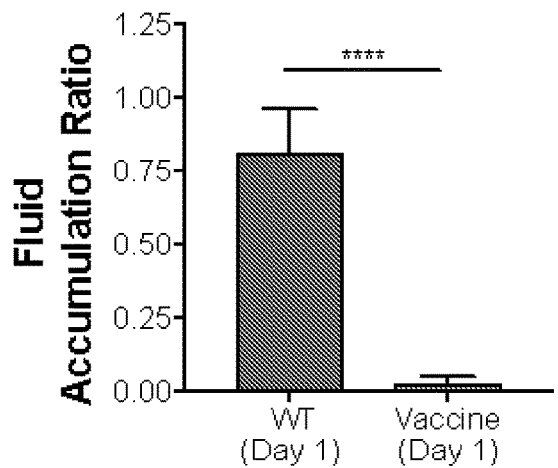

Infant rabbit infections were performed as previously described (Ritchie et al. (2010) $MBio$. 1(1): e00047-10) with minor modifications detailed below. All experiments were conducted using 1-4 day old New Zealand White Rabbits, and animals were co-housed with littermates and a lactating dam for the duration of all studies, which varied in length based on the phenotypes assessed. Animals were obtained from either Pine Acre Rabbitry (Norton, Mass., USA) or Charles River Canada, and phenotypes were consistent across animals from both vendors. Animal studies were always conducted using within-litter controls to minimize the impacts of litter-to-litter variation. Initial studies of HaitiWT and HaitiV colonization (FIG. 4A-C) were conducted following intraperitoneal injection of ranitidine-hydrochloride (2 µg/g body weight) to reduce stomach acidity, however, this treatment was omitted from all subsequent studies because it had no discernible impact on HaitiWT or HaitiV colonization. Animals were oro-gastrically inoculated with approximately $10^9$ CFU (500 µL of a $2 \times 10^9$ CFU/mL bacterial suspension) using a size 5 French catheter (Arrow International, Reading, Pa., USA). One-day-old animals were used for single-inoculation and co-inoculation studies. These animals, were typically euthanized approximately 18 hours post-inoculation; however, longitudinal studies of HaitiV colonization were conducted by inoculating 1 day old animals and monitoring their condition through approximately 90 hours post-inoculation. For sequential inoculation studies, 1 day old animals were inoculated with one of 3 treatments: "mock"—500 µL 2.5% sodium bicarbonate solution, "killed vaccine"—500 µL of a $2 \times 10^9$ CFU/mL suspension of formalin-killed HaitiV, or "live vaccine"—500 µL of a $2 \times 10^9$ CFU/mL suspension of HaitiV. 24 hours later, the same animals were inoculated with approximately $10^9$ CFU (500 µL of a $2 \times 10^9$ CFU/mL suspension of the challenge strain: HaitiWT: FIGS. 5A, 5B, 6A-C; N16961: FIG. 5C; or HaitiTn: FIGS. 5D and 5F). For sequential inoculation studies that report bacterial burden, animals were euthanized approximately 18 hours after challenge, with the exception of FIG. 6C.

At necropsy, the entire intestinal tract was removed, cecal fluid was extracted using a 26½ gauge needle and transferred to a pre-weighed Eppendorf tube. 2-3 cm sections of the distal small intestine, along with the entire cecum, were placed in pre-weighed homogenization tubes containing 1 mL sterile PBS and two 3.2 mm stainless steel beads (BioSpec Products Inc., Bartlesville, Okla., USA) and all filled tubes were weighed. The mass of fluid recovered from the cecum was divided by the mass of the cecum to obtain a fluid accumulation ratio (FAR). The tubes containing tissue were homogenized for 2 minutes on a mini-bead-beater-16 (BioSpec Products Inc., Bartlesville, Okla., USA), serially diluted in 1×PBS, and plated. Plates were incubated at 30° C. overnight and the number of observed colonies was divided by the appropriate dilution ratio and the mass of the corresponding tissue/fluid sample to yield a measure of CFU/g tissue. Homogenates were plated on LB+Sm200/X-Gal60 to enumerate total burden (i.e., HaitiWT+HaitiV) and on LB+SXT to enumerate HaitiWT burden alone. For co-inoculation or sequential inoculation studies, the absence of a HaitiV-specific selectable marker prevented the enumeration of HaitiV CFU unless the burden of HaitiV was comparable to HaitiWT (i.e., within 100-fold). Similarly, for studies utilizing the N16961 WT strain, which is sensitive to SXT, the number of blue colonies on LB+Sm200/X-Gal60 was used to enumerate WT burden. For co-inoculation studies, a competitive index was calculated as:

$$\text{Competitive Index} = \frac{HaitiV\ CFU \div HaitiWT\ CFU_{distal\ small\ intestine}}{(HaitiV\ CFU \div HaitiWT\ CFU)_{inoculum}}$$

For studies using the HaitiWT transposon library, the terminal 10 cm of the distal small intestine were obtained at necropsy, weighed, and homogenized as described above. The homogenate was serially diluted in 1×PBS and plated on LB+Sm200/X-Gal60 to enumerate total burden and LB+Sm200/Kan50 to enumerate the burden of HaitiTn. The remaining 900 µL of undiluted tissue homogenate were plated on LB+Sm200/Kan50 to recover representative samples of the in vivo passaged HaitiTn library that were used for subsequent analyses of sites of transposon insertion.

Colonization data were not reported for animals that reached a moribund state of disease in studies of disease progression, because the interval between inoculation and euthanasia, which varies substantially in these studies, is likely to impact bacterial burden. Instead, animals were euthanized upon assessment of moribund status characterized by a combination of visible diarrhea (staining of the ventral surface), dehydration (skin tenting), weight loss, lethargy (minimal movement), and decreased body temperature (cold to the touch). These assessments were carried out in a blinded fashion as to whether animals received killed vaccine or live vaccine. One animal progressed to moribund status without developing visible diarrhea, explaining the differences in sample sizes between FIGS. 6A and 6B).

Transposon-Insertion Sequencing Analysis

The transposon-insertion libraries were characterized by massively parallel sequencing; sequence data were processed and mapped to the *V. cholerae* H1 genome (see, e.g., Bashir et al. (2012) *Nat. Biotechnol.* 30(7): 701-7) as previously described (see Pritchard et al. (2014) *PLoS Genet.* 10(11): e1004782). Higher complexity libraries (>30,000 unique genotypes) were compared to the input libraries using the ARTIST pipeline. Data were corrected for origin proximity using a LOESS correction of 100,000 bp windows. The inoculum data sets were independently normalized relative to intestinal data sets using Con-ARTIST's multinomial distribution-based random samplings (n=100). A modified version of Con-ARTIST's Mann-Whitney U function was used to compare the intestinal data sets to their 100 simulated control data sets. Thresholds of mean informative sites>5|Log$_2$(mean fold change)|>1, mean inverse P-value>100 were imposed to identify loci for which corresponding insertion mutants are significantly enriched or depleted in the intestinal data sets relative to the inoculum.

Modeling of Cholera Outbreaks

Our model, adapted from a previous study (Azman (2015) *PLoS Med.* 12: e1001867), is depicted schematically in FIG. 10A. Parameters for disease transmission have been previously published (FIG. 10B). The vaccine rollout was modeled as proceeding at a constant number of doses per day over the duration of the campaign (7 days in FIGS. 6D, 11B; varied in FIG. 11A) until 70% of the total population was vaccinated. The campaign was triggered when the number of symptomatic cases (estimated as 25% of total infections in a previously-susceptible population; see Jackson et al. (2013) *Am. J. Trop. Med. Hyg.* 89: 654-64) exceeded a threshold (1,000 people in FIG. 6D, 11A; varied in FIG. 11B). The transmission rate (β) used for simulations was calculated assuming a basic reproductive (R$_0$) number in the range of 1 to 5, consistent with previous cholera outbreaks, with R$_0$=β/γ. Consistent with previous modeling studies (Azman et al. (2013) *J. Infect.* 66: 432-8), the average duration of infectiousness (1/γ) estimated in a household transmission study was assumed (Weil et al. (2009) *Clin. Infect. Dis.* 49: 1473-9). To compare the impact of using a fast vaccine, such as HaitiV, over a slower-acting alternative with equal efficacy against infection, an average time to onset of protection of 1 day versus 10 days (1/τ) after receipt of a single dose was assumed. A "leaky" mode of vaccine action reducing the rate of acquisition by 70% (θ) was modeled. Ordinary differential equations were solved in MATLAB R2016b (Mathworks, Natick, Mass.) using the ode45 function, with initial conditions of a single exposed individual in an otherwise susceptible population. For this model, the system of differential equation is:

$$\lambda = \beta(I_U + I_V + I_P)/N$$

$$\frac{dS_U}{dt} = -\lambda S_U - \rho(t)S_U/N_U$$

$$\frac{dE_U}{dt} = \lambda S_U - \sigma E_U - \rho(t)E_U/N_U$$

$$\frac{dI_U}{dt} = \sigma E_U - \gamma I_U - \rho(t)I_U/N_U$$

$$\frac{dR_U}{dt} = \gamma I_U - \rho(t)R_U/N_U$$

$$\frac{dS_V}{dt} = -\lambda S_V + \rho(t)S_U/N_U - \tau S_V$$

$$\frac{dE_V}{dt} = \lambda S_V - \sigma E_V + \rho(t)E_U/N_U - \tau E_V$$

$$\frac{dI_V}{dt} = \sigma E_V - \gamma I_V + \rho(t)I_U/N_U - \tau I_V$$

$$\frac{dR_V}{dt} = \gamma I_V + \rho(t)R_U/N_U - \tau R_V$$

$$\frac{dS_P}{dt} = -\lambda(1-\theta)S_P + \tau S_V$$

$$\frac{dE_P}{dt} = \lambda(1-\theta)S_P - \sigma E_P + \tau E_V$$

$$\frac{dI_P}{dt} = \sigma E_P - \gamma I_P + \tau E_V$$

$$\frac{dR_P}{dt} = \gamma I_P + \tau R_V$$

Results

Generation of the Genetically Engineered *Vibrio cholerae* Bacterial Strain HaitiV for Use as a Live Attenuated Vaccine Nine different modifications were generated to derive the new vaccine, HaitiV (Table 5), and whole genome sequencing was used to confirm that the mutations were present. Mutations were engineered to ensure biosafety, to a degree unprecedented among cholera vaccines, while maintaining HaitiV's capacity for intestinal colonization so that, like wild type *V. cholerae* and some previously tested live vaccine candidates (Cohen et al. (2002) *Infect. Immun.* 70: 1965-70; and Chen et al. (2016) *Clin. Infect. Dis.* 62(11): 1329-35), it would likely impart long-term immunity after a single oral dose. To ensure the safety of HaitiV, we removed the bacteriophage (CTXΦ) encoding cholera toxin (CT) (Waldor and Mekalanos (1996) *Science* 272(5270): 1910-4) (FIG. 1), the pathogen's principal virulence factor, and provided stringent impediments to toxigenic reversion. The boundaries of the CTXΦ deletion result in the removal of a sequence necessary for its chromosomal integration, as well as the gene encoding the multifunctional MARTX toxin, rtxA (see Fullner et al. (2002) *J. Exp. Med.* 195(11): 1455-

Figure 2:
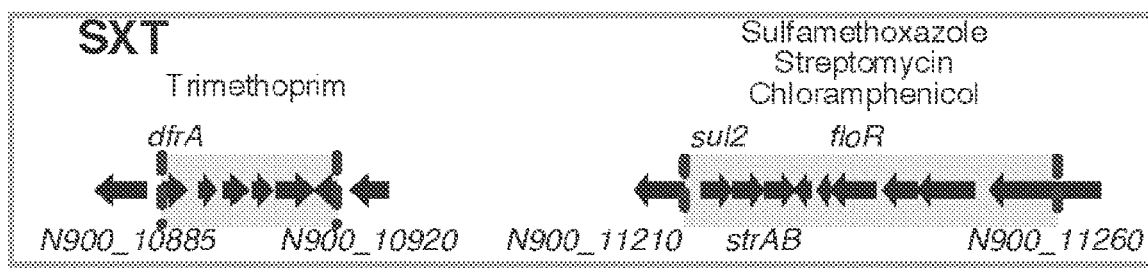
Figure 3A:
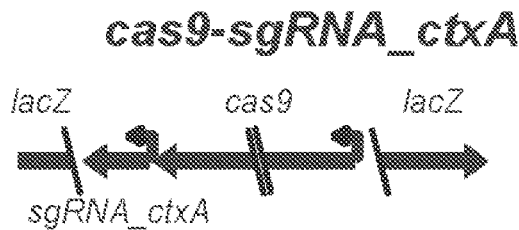
Figure 3B:
Figure 3C:
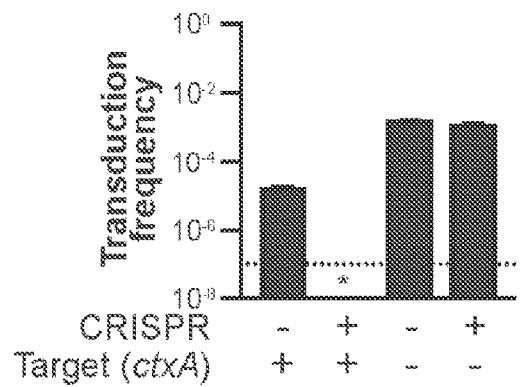
Figure 4B:
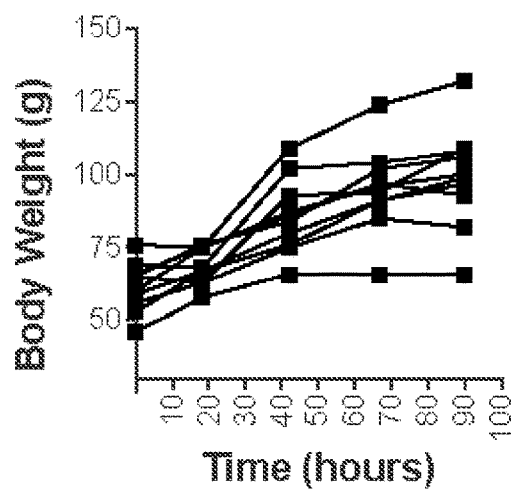

62). Additionally, HaitiV lacks hupB, a gene necessary for episomal maintenance of CTXΦ (see Martinez et al. (2015) *PLoS Genet.* 11(5): e1005256). HaitiV also encodes a CRISPR/Cas9 system specifically targeting the toxin gene ctxA. CTXΦ bearing intact ctxA was unable to infect the vaccine bearing this system, whereas a CTXΦ variant lacking ctxA showed no such barrier to infection (FIGS. 3A-3C). Additional vaccine engineering included steps to 1) reduce potential vaccine reactogenicity by deleting the 5 flagellins of *V. cholera* (see Rui et al. (2010) *Proc. Natl. Acad. Sci. U.S.A.* 107(9): 4359-64); 2) eliminate the vaccine's capacity to transfer genes, conferring resistance to antibiotics, that lie within the SXT Integrative Conjugative Element (ICE) (FIG. 2); 3) allow the vaccine to produce the non-toxic B subunit of CT (FIG. 7), which may elicit protection against diarrheal disease caused by enterotoxigenic *E. coli* as well as *V. cholerae* (Kauffman et al. (2016) *MBio.* 7(6): e 02021-16); and 4) minimize potential gene acquisition by deleting recA, thereby markedly reducing the strain's capacity for DNA recombination. The genetic alterations in the HaitiV live attenuated cholera vaccine are summarized in Table 5.

lated with HaitiV continued to gain weight up to 90HPI, providing further indication that HaitiV inoculation is not detrimental to overall health or development of the animals (FIG. 4B).

Figure 4C:
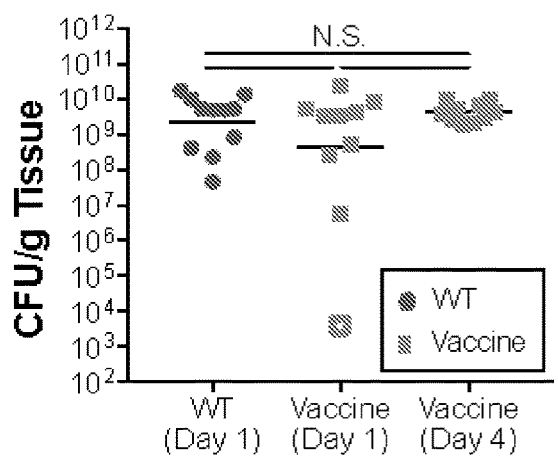

The distinct responses to HaitiWT or HaitiV inoculation were not associated with differences between intestinal colonization by the two strains. At 18HPI, there was no significant difference in *V. cholerae* colonization of the distal small intestine between littermates inoculated with HaitiV or HaitiWT (FIG. 4C). HaitiV burden showed no reduction by 90HPI (FIG. 4C), indicating that prolonged intestinal colonization by HaitiV does not cause disease. Although levels of intestinal colonization by HaitiV and HaitiWT were not statistically distinguishable in single inoculation experiments, when animals were co-inoculated with a 1:1 mixture of HaitiWT and HaitiV, the wild type strain outcompeted the vaccine strain (FIG. 4D). HaitiV's colonization is comparable to that of strains closely related to Peru-15 (see Rui et al. (2010)), an earlier live cholera vaccine candidate that was found to be safe and to confer protective immunity with a single dose (see Cohen et al. (2002)); thus, a single dose of HaitiV is expected to prompt protective adaptive immunity.

TABLE 5

Genetic alterations present in the exemplary HaitiV live attenuated cholera vaccine

| Mutation | Rationale |
| --- | --- |
| ΔCTXΦ | Attenuates by removing the genes encoding cholera toxin and the multifunctional toxin MARTX (see Fullner et al. (2002) *J. Exp. Med.* 195(11): 1455-62); protects against toxigenic reversion by preventing chromosomal integration of CTXΦ (see Waldor and Mekalanos (1996) *Science* 272(5270): 1910-4). |
| ΔflaBDE/ΔflaAC | Attenuates and reduces potential reactogenicity (see Rui et al. (2010) *Proc. Natl. Acad. Sci. U.S.A.* 107(9): 4359-64). |
| ΔfloR-strAB-sul2/ΔdfrA | Prevents the dispersal of antibiotic resistance genes. |
| N900_115550::Phtpg-ctxB | Constitutive expression of CtxB (FIG. 7) promotes anti-CtxB immune response that may protect against diarrheal disease caused by *V. cholerae* and enterotoxigenic *E. coli* (ETEC) (see Kauffman et al. (2016) *MBio.* 7(6): e 02021-16). |
| ΔhupB | Protects from toxigenic reversion by inactivating the HU complex, which is necessary for extrachromosomal replication of CTXΦ (see Martinez et al. (2015) *PLoS Genet.* 11(5): e1005256). |
| lacZ::cas9-sgRNA_ctxA | Endonuclease targeting of ctxA prevents toxigenic reversion. |
| ΔrecA | Prevents homologous recombination-dependent gene acquisition. |

HaitiV is an Attenuated *V. cholerae* Bacterial Strain

Comparative studies of oro-gastrically inoculated HaitiV as compared to the wild type *V. cholerae* isolate from which it was derived (referred to herein as HaitiWT) were performed in infant rabbits, a small animal model that recapitulates many aspects of human cholera, including rapid mortality (see Ritchie et al. (2010) *MBio.* 1(1): e00047-10). All animals inoculated with HaitiWT progressed to a moribund state by 18 hours post-inoculation (18HPI). Upon necropsy, the ceca of these animals were filled with fluid (FIG. 4A) which has been previously found to resemble ctxAB-dependent choleric diarrhea (see Ritchie et al. (2010)). In marked contrast, minimal or no fluid accumulated by 18HPI in the ceca of littermates inoculated with HaitiV (FIG. 4A). Animals inoculated with HaitiV did not exhibit cholera-like illness during observation periods extending to 90HPI, although in rare cases animals showed mild and self-limited non-choleric diarrhea. Animals inocu- Inoculation with HaitiV Induces a Protective Response Against the Virulent *V. cholerae* Bacterial Strain HaitiWT Given HaitiV's robust and prolonged occupancy of the intestine, experiments were performed to determine whether HaitiV-colonized animals might exhibit resistance to colonization by HaitiWT even prior to the development of an adaptive immune response, for example due to alteration of the pathogen's intestinal niche. Animals were inoculated either with HaitiV (live vaccine), formalin-killed HaitiV (killed vaccine), or a buffer control (mock), and then challenged 24 hours later with a lethal dose of HaitiWT. Animals in the buffer and formalin groups developed severe cholera-like illness following HaitiWT challenge, and intestinal burdens of HaitiWT in these animals resembled those without pretreatment (FIGS. 5A, 5B, and 4C). Conversely, no animals that received live vaccine exhibited signs of severe disease within 18 hours of HaitiWT challenge, and lower levels of HaitiWT were recovered from the intestines of animals previously inoculated with live vaccine versus those inoculated with killed vaccine (FIG. 5B). The reduction in HaitiWT burden varied in magnitude across animals previously inoculated with live vaccine, falling below the limit of detection in two animals. The live vaccine's antagonism of HaitiWT colonization (i.e., colonization resistance) appeared to be dependent on prior inoculation with HaitiV; normal burdens of HaitiWT were observed in animals inoculated with the two strains simultaneously rather than sequentially (FIG. 4E versus FIG. 5B).

To assess the specificity of colonization resistance, the vaccine study was repeated, challenging with *V. cholerae* N16961, an early El Tor strain administered to human volunteers in studies of cholera vaccine efficacy (see Chen et al. (2016) *Clin. Infect. Dis.* 62(11): 1329-35). Importantly, the Haitian and N16961 strains were isolated independently and are of distinct serotypes (see Chin et al. (2011) *N. Engl. J. Med.* 364(1): 33-42). Animals inoculated with live HaitiV, but not killed HaitiV, also exhibited colonization resistance against the N16961 WT challenge (FIG. 5C), demonstrating that HaitiV-mediated colonization resistance is neither strain-nor serotype-specific.

Given the low levels of HaitiWT burden in animals inoculated with HaitiV, it was possible that the vaccine's occupancy of the intestine interfered with processes required for colonization by the challenge strain. Therefore, a forward genetic screen to identify mutations that allow HaitiWT to resist or evade vaccine-mediated antagonism was performed. Such mutations could provide insight into the mechanism(s) by which HaitiV mediates colonization resistance, and were predicted to confer a fitness advantage to HaitiWT, specifically in the HaitiV-colonized intestine. Animals were challenged with a pooled HaitiWT transposon insertion library (HaitiTn) in the absence of pretreatment (single inoculation, FIGS. 5D and 5E) or 24 hours post-inoculation with live vaccine (sequential inoculation, FIGS. 5F and 5G). HaitiTn colonization in the absence of pretreatment was indistinguishable from HaitiWT colonization of animals previously inoculated with a mock treatment or killed vaccine (FIG. 5D vs. FIGS. 5A and 5B). Additionally, the range of HaitiTn colonization in vaccine-pretreated animals recapitulated the highly variable HaitiWT burden observed upon sequential inoculation of HaitiV and HaitiWT (FIG. 5F vs. FIG. 5B).

To identify enriched mutants, the transposon junctions from HaitiTn recovered from the distal small intestine were sequences and a genome-wide comparison of mutant abundance in animals subjected to HaitiTn challenge without pretreatment (FIG. 5) or following HaitiV inoculation (FIG. 5G) was performed. To ensure requisite statistical power, the analysis was restricted to animals colonized by sufficiently diverse HaitiTn populations encompassing multiple independent disruptions per gene (rabbits r3-r6 for single inoculation, rabbits r4-r7 for sequential inoculation). Notably, insertions disrupting cqsS and hapR, components of a *Vibrio*-specific quorum sensing (QS) pathway, were enriched in multiple animals, independent of pretreatment (FIGS. 5E and 5G, FIGS. 8A-9D). QS down-regulates expression of virulence and colonization factors at high cell densities (Rutherford and Bassler (2012) *Cold Spring Harb. Perspect. Med.* 2(11): pii: a012427; Zhu et al. (2002) *Proc. Natl. Acad. Sci. U.S.A.* 99: 3129-34; Duan and March (2010) *Proc. Natl. Acad. Sci. U.S.A.* 107: 11260-4; and Hsiao et al. (2014) *Nature* 515: 423-6), and enrichment of cqsS and hapR mutants, which are blind to this inhibition, suggests that QS pathways constrain HaitiWT growth in the intestine. Corresponding enrichment of QS mutants was not identified in similar analyses of closely related *V. cholerae* isolates (Kamp et al. (2013) *PLoS Pathog.* 9: e1003800), suggesting that QS may play a distinct role in the pathogenesis of variant El Tor strains. The genome-wide screen failed to identify any mutants that were consistently and specifically enriched in vaccine-colonized animals, indicative that single loss-of-function mutations are unlikely to enable HaitiWT to resist or evade vaccine-mediated antagonism.

The genetic diversity intrinsic to the HaitiTn library utilized in the experiments described above allowed for an assessment as to whether HaitiV-mediated colonization resistance was associated with changes in the severity of the infection bottleneck that *V. cholerae* encounters in vivo (Abel et al. (2015) *Nat. Methods* 12: 223-6; Abel et al. (2015) *PLoS Pathog.* 11: e1004823). *V. cholerae* recovered from the intestine arise from a founding population of organisms that persist following a stochastic constriction of the bacterial inoculum (Abel et al. (2015) *Nat. Methods* 12: 223-6). The severity of this infection bottleneck can be estimated from the number of unique transposon insertion mutants recovered from the intestine (Chao et al. (2016) *Nat. Rev. Microbiol.* 14: 119-28). A subset of animals previously inoculated with live vaccine were colonized by relatively few unique insertion mutants and showed low HaitiTn burdens (FIG. 5F, rabbits r1-r3), suggesting that HaitiV-mediated colonization resistance is, in some cases, associated with a highly restrictive infection bottleneck. Importantly, there was no overlap in the mutants recovered from low diversity animals, which indicates that the restrictive infection bottlenecks observed in some HaitiV-inoculated animals are stochastic and genotype-independent. Reduced colonization was also observed in animals in which the vaccine did not appear to impose a bottleneck (FIG. 5F, rabbits r4-7). The variable bottlenecks observed in vaccine-colonized animals, along with the inability to identify mutants resistant to vaccine antagonism, highlights the possibility that the mechanism(s) underlying colonization resistance may be complex and/or multi-factorial. However, the lower burdens of HaitiWT and the absence of severe disease following challenge of vaccine-colonized animals suggests that inoculation with HaitiV may be sufficient to protect against cholera-like illness.

HaitiV Induces Protection Against the Virulent *Vibrio cholerae* Strain HaitiWT within 24 Hours of Administration To quantify HaitiV-dependent protection from cholera-like disease, infant rabbits were inoculated with live or killed vaccine, challenged with HaitiWT 24 hours later, and monitored regularly to assess their status. All animals inoculated with killed vaccine developed diarrhea (median onset 15 hours) and progressed to a moribund state within 29 hours of HaitiWT inoculation (median 18.8 hours) (FIG. 6A). In stark contrast, animals inoculated with live vaccine were significantly slower to develop diarrhea (median 28.3 hours; one animal did not develop visible diarrhea) and showed a marked increase in survival time post lethal challenge (median>41.3 hours; FIG. 6A) and in survival post onset of diarrhea (>13 hours versus 5 hours in control animals; FIG. 6B). Additionally, 4 animals inoculated with live vaccine had not reached a moribund state when the study was concluded 40 hours post lethal challenge despite detectable HaitiWT colonization in all animals (FIGS. 6A and 6C). Thus, HaitiV may protect from disease even in the absence of absolute colonization resistance. The rapidity of HaitiV-induced colonization resistance and disease protection, and the observation of these phenotypes in a neonatal model of infection, are not consistent with vaccine-elicited adaptive immune protection. Instead, the data indicate that HaitiV colonizes the intestine and mediates viability-dependent protection against cholera, properties consistent with the definition of a probiotic agent (see Hill et al. (2014) *Nat. Rev. Gastroenetrol. Hepatol.* 11: 506-514).

Figure 11A:
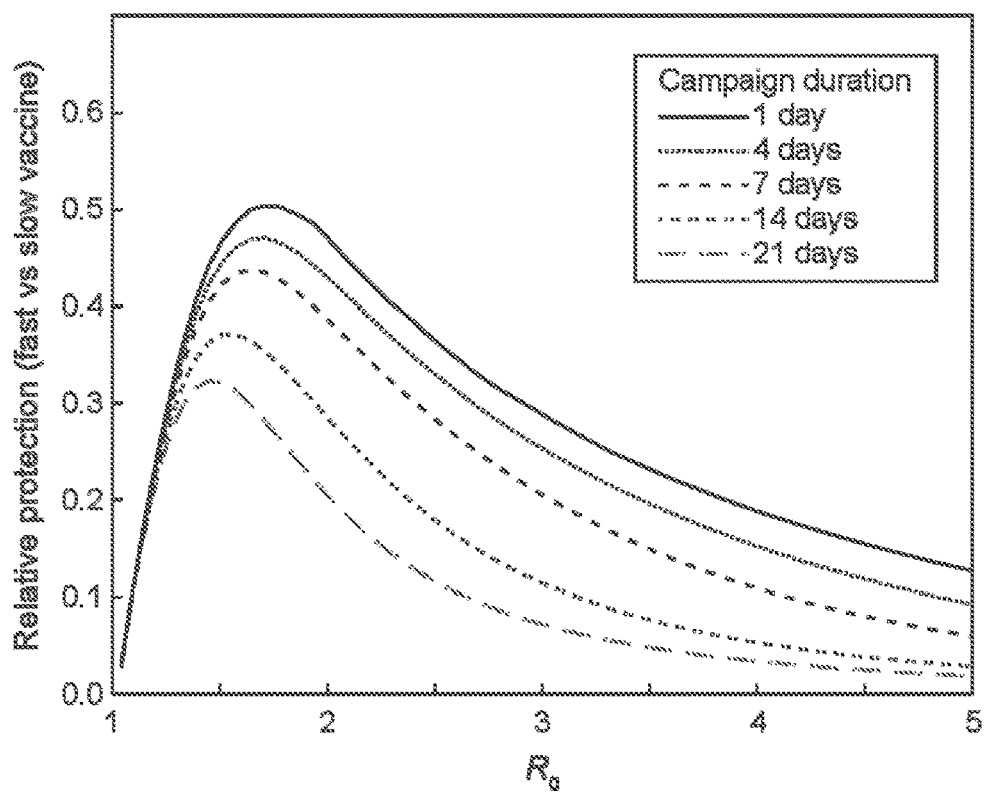
Figure 11B:
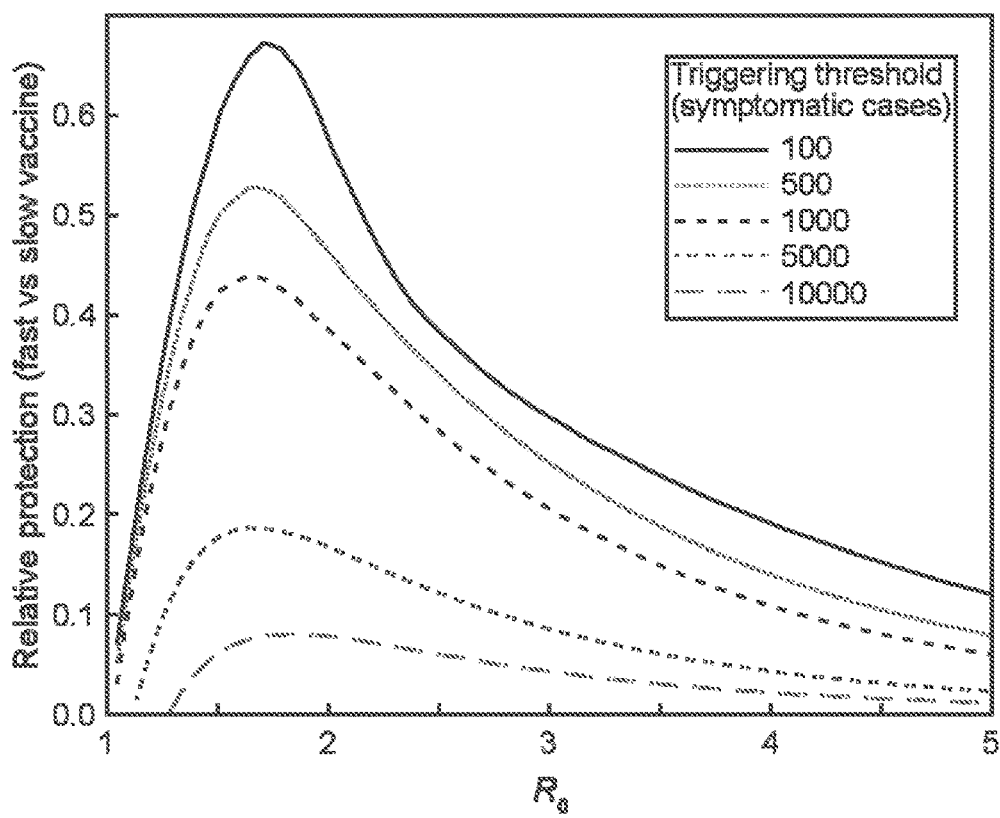
Figure 12A:
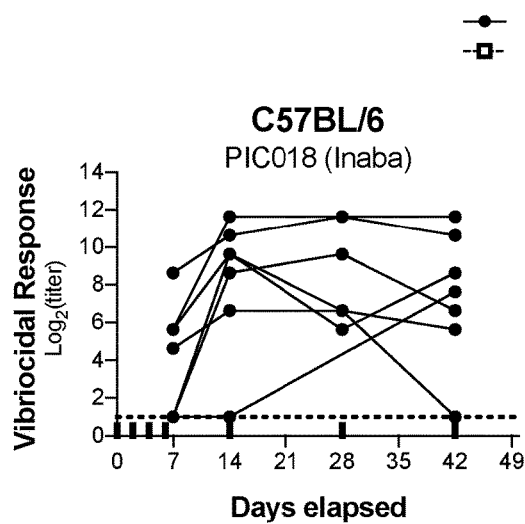
Figure 12B:
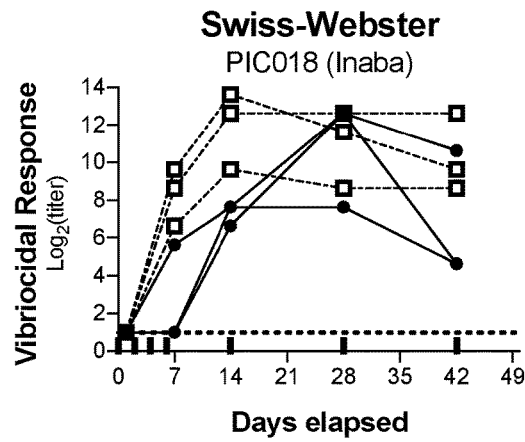
Figure 12C:
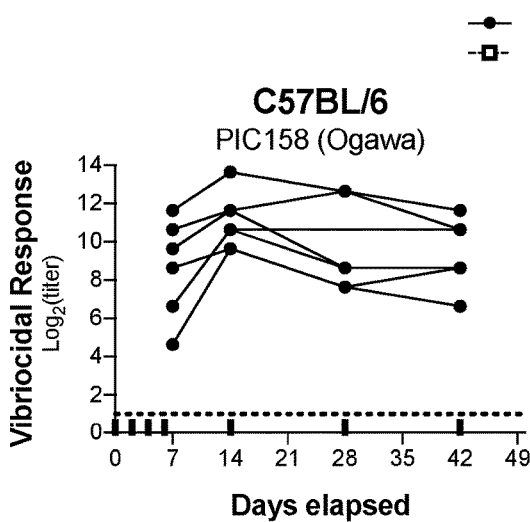
Figure 12D:
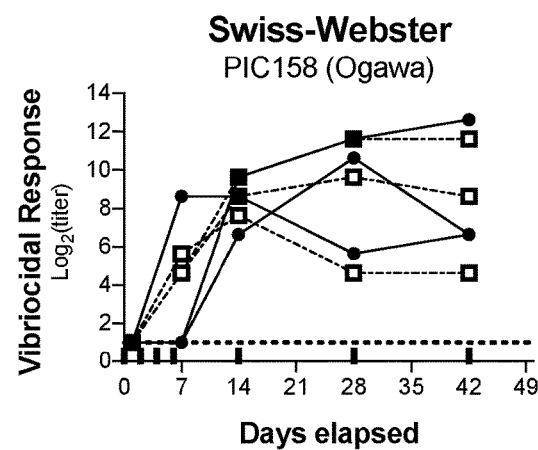
Figure 13A:
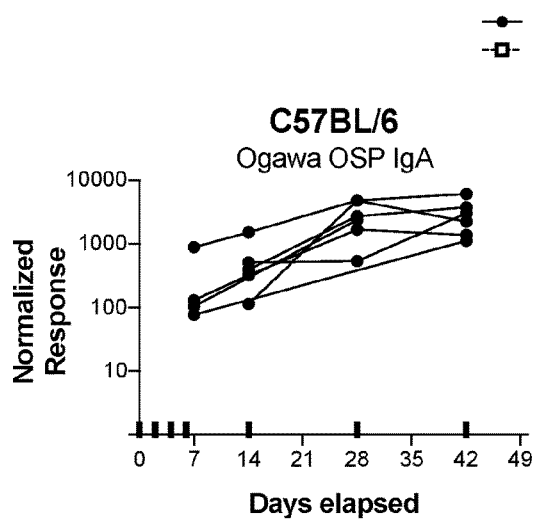
Figure 13B:
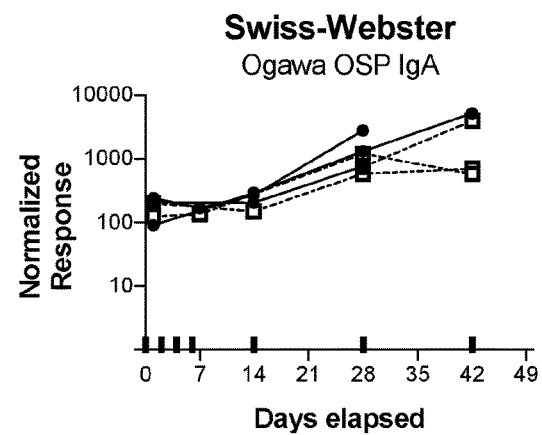
Figure 13C:
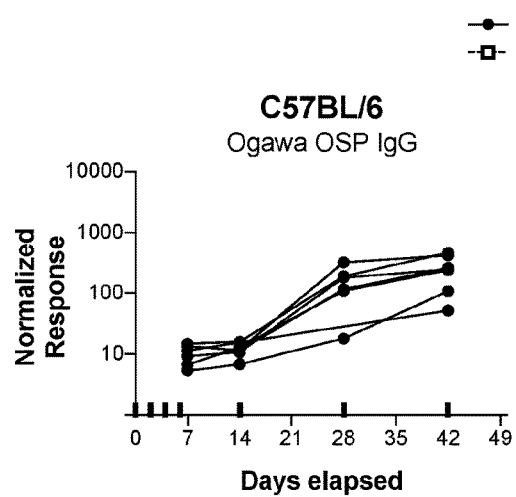
Figure 13D:
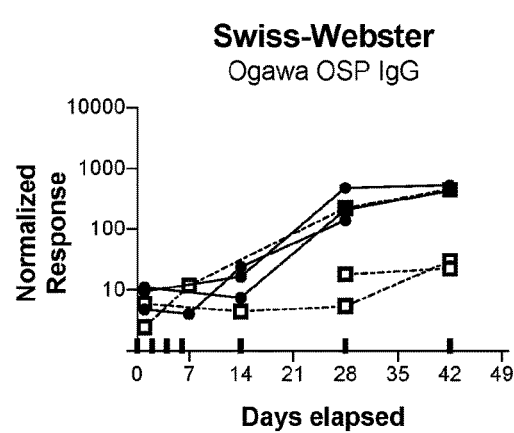
Figure 14A:
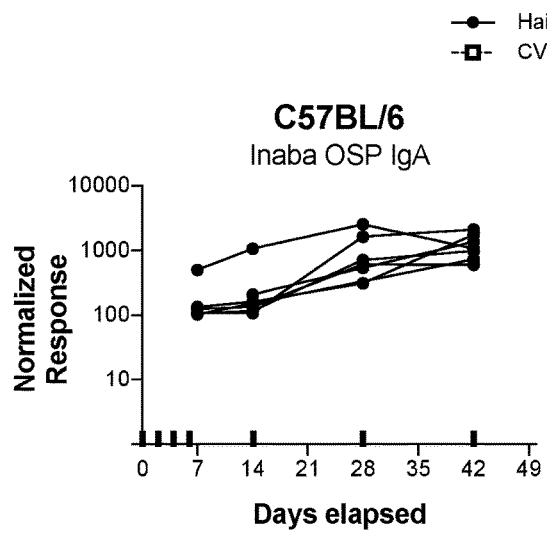
Figure 14B:
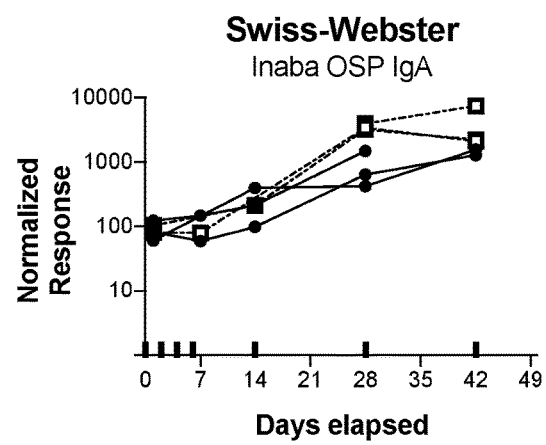
Figure 14C:
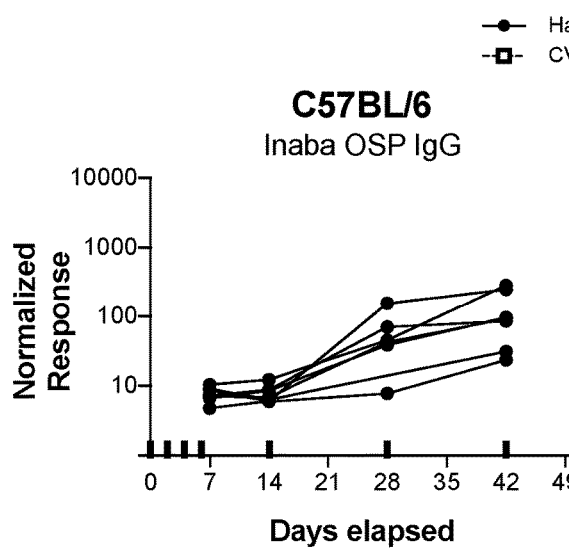
Figure 14D:
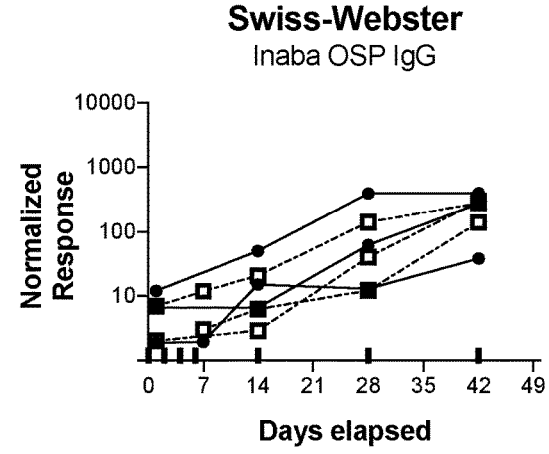

To investigate how HaitiV's rapid protection might impact reactive vaccination campaigns, a previously-published mathematical model of a cholera outbreak in a susceptible population, an epidemic context prioritized for reactive OCV interventions, was modified (Azman (2015) *PLoS Med.* 12: e1001867; Reyburn et al. (2011) *PLoS Negl. Trop. Dis.* 5: e952). Modifications to the mathematical model (FIG. 10A) allowed for the computation of the effects of vaccines that confer equal degrees of protection in 1 day (fast vaccine—based on observations in FIG. 5A-5G, 6A, and 6B) or in 10 days (slow vaccine—when some recipients of killed OCVs manifest vibriocidal titers (Matias et al. (2016) *PLoS Negl. Trop. Dis.* 10: e0004753). Varying different model parameters revealed that maximal benefit of a fast vaccine, relative to a slow vaccine, occurs under transmission dynamics consistent with recent outbreaks (R0: 1.5 to 3) and with rapid vaccine administration (FIGS. 10B, 11A and 11B). These simulations revealed that, compared to a slow vaccine, an equally efficacious fast vaccine could avert an additional 20,000 infections in a population of 100,000 (FIG. 6D) by preventing infections that could be acquired in the window between administration of the slow vaccine and the emergence of protective immunity.

Provided herein is the design and characterization of a new live attenuated cholera vaccine candidate, HaitiV. The studies above indicate that HaitiV is refractory to toxigenic reversion and that it colonizes an animal model of cholera without causing cholera-like disease or other untoward effects. The infant rabbit model is well-suited for the intestinal colonization and disease progression studies reported above. The study is limited by the poorly characterized intestinal microbiota and adaptive immune capacity of rabbit neonates, which restrict further investigation of HaitiV's mechanism(s) of action and immunogenicity in this system. There are no robust animal models to investigate adaptive immunity to cholera; as with previous cholera vaccines, evaluating the adaptive immune response elicited by HaitiV will require human volunteer studies. Encouragingly, HaitiV's colonization was comparable to that of strains closely related to Peru-15 in the same model (Rui et al. (2010) *Proc. Nat'l. Acad. Sci. USA* 107(9): 4359-64), an earlier live cholera vaccine candidate found to be safe in humans and to confer protection with a single dose (Cohen et al. (2002) *Infect. Immun.* 70: 1965-70) even in children under 5 who are not protected by killed OCVs (Qadri (2007) *Vaccine* 25: 231-8. Surprisingly, HaitiV was found to confer protection within 24 hours of administration, an interval that is not consistent with adaptive immunity and unprecedented among existing vaccines. Notably, these effects required use of viable HaitiV; formalin-killed HaitiV did not provide acute protection from disease, suggesting that rapid protection requires a probiotic effect that is unlikely to be elicited by killed OCVs. Human challenge studies are a well-established system for assessing the adaptive immune protection elicited by OCVs (Chen et al. (2016) *Clin. Infect. Dis.* 62(11): 1329-35 and Cohen et al. (2002) *Infect. Immun.* 70: 1965-70). Incorporating additional acute challenges (e.g., within 24 hours post-vaccination) will illuminate the onset and duration of OCV protection, thereby assessing whether HaitiV or other OCVs elicit protection prior to adaptive immune responses, as observed in the infant rabbit model.

Although the mechanisms underlying HaitiV's acute protection are likely complex and require further elucidation, the mathematical modeling described in this study indicates that the public health impacts of HaitiV's rapid protection could be transformative in the context of reactive vaccination during cholera epidemics. Relative to controls, HaitiV-inoculated animals challenged with a lethal dose of HaitiWT survived longer following the onset of diarrhea, displayed lower levels of HaitiWT colonization, and in some cases, were completely protected from cholera. HaitiV-induced delay of disease progression suggests that individuals who are infected with pathogenic *V. cholerae* after being inoculated with HaitiV may have more time to access life-saving treatment following the onset of symptoms. The time that elapses between onset of symptoms and administration of treatment is often the determinant of case fatality rates during cholera outbreaks, because re-hydration therapy is sufficient to prevent death in virtually all symptomatic individuals (Farmer et al. (2011) *PLoS Negl. Trop. Dis.* 5: e1145). Additionally, the colonization resistance mediated by HaitiV, but not formalin-killed HaitiV, suggests that inoculation with HaitiV may reduce shedding of toxigenic *V. cholerae* into the environment, the transmission route that perpetuates outbreaks. Although HaitiV's potential effects on transmission were not incorporated into the modeling studies, a reduction in transmission is likely to potentiate the already dramatic impact that HaitiV could have on outbreak control. Overall, the above studies suggest that probiotic vaccines, mediating rapid protection from disease while eliciting adaptive immunity, could constitute a new class of therapeutics with a transformative impact on outbreak control.

Example 2. HaitiV Induces a Vibriocidal Antibody Response and Anti-OSP Antibodies in Mice HaitiV Induces a Vibriocidal Antibody Response in Mice To determine whether inoculation with HaitiV induces a vibriocidal antibody response, C57BL/6 and Swiss-Webster mice were inoculated with either HaitiV or a spontaneous streptomycin resistant mutant derived from the *V. cholerae* bacterial strain CVD103-HgR, referred to herein as CVD103-HgR* (control). CVD-103HgR (Vaxchora™; PaxVax, Inc., Redwood City, Calif., USA) is currently approved for the prevention of cholera caused by *V. cholerae* O1 in adult travelers. Sera vibriocidal activity was analyzed using an in vitro microdilution assay to assess complement-mediated cell lysis of *V. cholerae* PIC018 (Inaba serotype) or PIC158 (Ogawa serotype). As shown in FIGS. 12A-12D, a robust vibriocidal response was observed in sera collected from mice 7 days after initial inoculation with either HaitiV or CVD103-HgR*.

Anti-OSP IgA and IgG Titers Increase Over Time in Mice Inoculated with HaitiV

To determine whether inoculation with HaitiV induces an antibody response against O-antigen-specific polysaccharide (OSP), C57BL/6 and Swiss-Webster mice were inoculated with either HaitiV or CVD103-HgR* (control), and the abundance of anti-OSP IgA and anti-OSP IgG antibodies against either Ogawa-derived or Inaba-derived OSP was measured using ELISA. As shown in FIGS. 13A-13D and 14A-14D, the abundance of anti-OSP IgG and IgA antibodies increased over time. Mice inoculated with HaitiV exhibited a more pronounced IgG response to Ogawa-derived OSP than mice inoculated with CVD103-HgR*.

Materials and Methods

The following materials and methods were used in this Example.

To generate a streptomycin resistant strain of CVD103-HgR (Vaxchora™; PaxVax, Inc., Redwood City, Calif., USA), the bacterial strain was inoculated into 5 mL of LB broth and cultured with aeration (250 rpm) at 37° C. overnight. 1 mL of the overnight culture was plated on LB agar+streptomycin (1000 µg/mL) and incubated at 37° C.

overnight. Colonies that arose on LB agar+streptomycin (1000 µg/mL) were considered spontaneous streptomycin resistant mutants of CVD103-HgR, hereafter referred to as CVD103-HgR*.

HaitiV immunogenicity studies were conducted using female, germ-free C57BL/6 mice (n=7, Massachusetts Host-Microbiome Center) and female, germ-free Swiss-Webster mice (n=6, Taconic Farms) housed in a BL-2 animal facility for the duration of study. HaitiV or CVD103-HgR* bacteria were resuspended in 2.5% sodium bicarbonate solution (pH 9.0) to a final concentration of $10^{10}$ colony forming units per mL (CFU/mL). Mice were anesthetized via isoflurane inhalation and orally gavaged with 100 µL of the bacterial suspension ($10^9$ CFU per mouse). This procedure was repeated at 2, 4, 6, 14, 28, and 42 days following the initial immunization. Mice were monitored daily for signs of disease and weighed every 4-5 days and prior to each immunization. Fecal pellets were obtained at each weighing, and pellets were homogenized in 1× phosphate buffered saline (PBS) and serial dilutions were plated on LB+streptomycin (200 µg/mL) to enumerate fecal burdens of HaitiV. For the C57BL/6 cohort, blood samples were obtained via tail vein incision at 7, 14, 28, and 42 days post-immunization. For the Swiss-Webster cohort, blood samples were obtained via tail vein incision at 1, 7, 14, 28, and 42 days post-immunization. Blood was allowed to clot at room temperature for 1 hour, centrifuged at 13,000 rpm for 5 minutes, and the supernatant (serum) was collected and stored at −20° C. for subsequent analyses.

Vibriocidal antibody quantification was performed as previously described (Rollenhagen et al. (2009) *Vaccine* 27(36): 4917-22, and Tarique et al. (2012) *Clin. Vaccine Immunol.* 19(4): 594-60, each of which is incorporated herein by reference) via an in vitro microdilution assay of complement-mediated cell lysis of *V. cholerae* PIC018 (Inaba) or PIC158 (Ogawa). Vibriocidal responses are reported as titers (i.e., the dilution of serum) causing a 50% reduction in *V. cholerae* optical density compared to wells with no added serum. Antibody responses to either Inaba or Ogawa O-antigen-specific polysaccharide (OSP) were assessed via enzyme-linked immunosorbent assay (ELISA) as described in Aktar et al. (2016) *Clin. Vaccine Immunol.* 23(5): 427-35, incorporated herein by reference. Data are presented as normalized response, which is the ratio of ELISA signal for the test sample to a standardized pool of sera included on each plate.

REFERENCES

1. Balakrishnan (2017) *Lancet Infect. Dis.* 17: 700-1.
2. Ali et al. (2015) *PLoS Negl. Trop. Dis.* 9: e0003832.
3. Clemens et al. (2017) *Lancet* 390(10101): 1539-49.
4. Qadri et al. (2015) *Lancet* 386: 1362-1371.
5. Luquero (2014) *N. Engl. J. Med.* 370: 2111-2120.
6. Kabir (2014) *Clin. Vaccine Immunol.* 21: 1195-1205.
7. Chen et al. (2016) *Clin. Infect. Dis.* 62: 1329-1335.
8. Qadri et al. (2007) *Vaccine* 25: 231-238.
9. Calain et al. *Vaccine* 22: 2444-2451.
10. Chin et al. (2011) *N. Engl. J. Med.* 364: 33-42.
11. Cohen (2002) *Infect Immun* 70: 1965-1970.
12. Waldor and Mekalanos (1996) *Science* 272: 1910-1914 (1996).
13. Fullner et al. (2002) *J. Exp. Med.* 195: 1455-1462.
14. Martinez et al. (2015) *PLoS Genet.* 11: e1005256.
15. Rui et al. (2010) *Proc. Natl. Acad. Sci. U.S.A.* 107,4359-4364 (2010).
16. Kauffman et al. (2016) *mBio* 7(6): e02021-16.
17. Ritchie et al. (2010) MBio. 1(1): e00047-10.
18. Rutherford and Bassler (2012) *Cold Spring Harb. Perspect. Med.* 2(11): pii: a012427.
19. Zhu et al. (2002) *Proc. Natl. Acad. Sci. U.S.A.* 99: 3129-3134.
20. Duan and March (2010) *Proc. Natl. Acad. Sci. U.S.A.* 107: 11260-11264.
21. Hsiao et al. (2014) *Nature* 515: 423-426.
22. Kamp et al. (2013) *PLoS Pathog.* 9: e1003800.
23. Abel et al. (2015) *Nat. Methods* 12: 12(3): 223-6.
24. Abel et al. (2015) *PLoS Pathog.* 11: e1004823.
25. Chao et al. (2016) *Nat. Rev. Microbial.* 14: 119-128.
26. Azman et al. (2015) *PLoS Med.* 12: e1001867.
27. Reyburn et al. (2011) *PLoS Negl. Trop. Dis.* 5: e952.
28. Matias et al. (2016) *PLoS Negl. Trop. Dis.* 10: e0004753.
29. Farmer et al. (2011) *PLoS Negl. Trop. Dis.* 5: e1145.
30. Pritchard et al. (2014) *PLoS Genet.* 10: e1004782.
31. Ferriéres et al. (2010) *J. Bacteria* 192: 6418-6427.
32. Millet (2014) *PLoS Pathog.* 10: e1004405.
33. Kenner et al. (1995) *J. Infect. Dis.* 172: 1126-1129.
34. Butterton et al. (1995) *Infect. Immun.* 63: 2689-2696.
35. Lazar et al. (1998) *Infect. Immun.* 66: 394-397.
36. Chiang and Rubin (2002) *Gene* 296: 179-185.
37. Bashir et al. (2012) *Nat. Biotechnol.* 30: 701-707.
38. Jackson et al. (2013) *Am. J. Trop. Med. Hyg.* 89: 654-664.
39. Azman et al. (2013) *J. Infect.* 66: 432-438.
40. Weil et al. (2009) *Clin. Infect. Dis.* 49: 1473-1479.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11484585B2). An electronic copy of the "Sequence Listing" will also be available from the USPTO upon request and payment of the fee set forth in 37 CFR 1.19(b)(3).

What is claimed is:

1. A genetically engineered *Vibrio cholerae* bacterium comprising:
   (a) a deletion in a nucleic acid sequence encoding a cholera toxin subunit A wherein the deletion renders the bacterium incapable of expressing the cholera toxin subunit A;
   (b) a heterologous nucleic acid sequence encoding a Cas9 nuclease molecule, wherein the Cas9 nuclease molecule is integrated into the genome of the bacterium;
   (c) a heterologous nucleic acid sequence encoding a guide RNA (gRNA), wherein the gRNA comprises a targeting domain which is complementary with a target nucleic acid sequence of ctxA;
   (d) a deletion in a nucleic acid sequence encoding a multifunctional-autoprocessing repeats-in-toxin (MARTX) toxin, wherein the deletion renders the bacterium incapable of producing the MARTX toxin;
   (e) a deletion in a nucleic acid encoding a flagellin, wherein the deletion renders the bacterium incapable of producing the flagellin; and
   (f) a deletion in a nucleic acid sequence encoding a RecA protein, wherein the deletion renders the bacterium incapable of producing RecA, wherein the bacterium is derived from a parental strain belonging to the El Tor biotype.

2. The genetically engineered *Vibrio cholerae* bacterium of claim 1, wherein the deletion in the nucleic acid sequence encoding the cholera toxin subunit A is located in a ctxA gene that was integrated into the genome of the bacterium.

3. The genetically engineered *Vibrio cholerae* bacterium of claim 1, wherein the bacterium comprises a deletion in a nucleic acid sequence of the core region of a CTXΦ genome that was integrated into the genome of the bacterium.

4. The genetically engineered *Vibrio cholerae* bacterium of claim 1, wherein the bacterium comprises a deletion in a nucleic acid sequence of the RS2 region of a CTXΦ genome that was integrated into the genome of the bacterium.

5. The genetically engineered *Vibrio cholerae* bacterium of claim 1, wherein the bacterium comprises a complete deletion of a CTXΦ genome that was integrated into the genome of the bacterium.

6. The genetically engineered *Vibrio cholerae* bacterium of claim 1, wherein the gRNA comprises the nucleic acid sequence 5'-cctgatgaaataaagcagtcgttttagagctagaaat agcaagt-taaaataaggctagtccgttatcaacttgaaaaagtggcaccgagtcggtgc-3' (SEQ ID NO: 3).

7. The genetically engineered *Vibrio cholerae* bacterium of claim 1, wherein the nucleic acid sequence encoding the MARTX toxin is selected from the group consisting of rtxA, rtxB, rtxC, rtxD, and rtxE.

8. The genetically engineered *Vibrio cholerae* bacterium of claim 1, wherein the bacterium further comprises a deletion in a nucleic acid sequence encoding a DNA-binding protein HU-beta.

9. The genetically engineered *Vibrio cholerae* bacterium of claim 8, wherein the nucleic acid sequence encoding the DNA-binding protein HU-beta is a hupB gene.

10. The genetically engineered *Vibrio cholerae* bacterium of claim 1, wherein the nucleic acid sequence encoding a flagellin is selected from the group consisting of flaA, flaB, flaC, flaD, and FlaE.

11. The genetically engineered *Vibrio cholerae* bacterium of claim 1, wherein the bacterium comprises a heterologous nucleic acid, wherein the heterologous nucleic acid comprises a gene encoding cholera toxin subunit B that is operably-linked to a promoter.

12. The genetically engineered *Vibrio cholerae* bacterium of claim 11, wherein the gene encoding cholera toxin subunit B is a ctxB gene.

13. The genetically engineered *Vibrio cholerae* bacterium of claim 11, wherein the promoter is a $P_{htpg}$ promoter.

14. The genetically engineered *Vibrio cholerae* bacterium of claim 1, wherein the bacterium is derived from a Haiti parental strain, and/or is Inaba serotype, Ogawa serotype, or Hikojima serotype.

15. A pharmaceutical composition comprising the genetically engineered *Vibrio cholerae* bacterium of claim 1 and a pharmaceutically acceptable excipient.

16. The genetically engineered *Vibrio cholerae* bacterium of claim 1, wherein the bacterium comprises deletion of a dfrA gene, wherein the dfrA gene encodes a product that confers resistance to trimethoprim, and wherein the deletion prevents dispersal of the dfrA gene to other bacteria.

17. The genetically engineered *Vibrio cholerae* bacterium of claim 1, wherein the bacterium comprises deletion of a sul2 gene, wherein the sul2 gene encodes a product that confers resistance to sulfamethoxazole, and wherein the deletion prevents dispersal of the sul2 gene to other bacteria.

18. The genetically engineered *Vibrio cholerae* bacterium of claim 1, wherein the bacterium comprises deletion of a strAB gene, wherein the strAB gene encodes a product that confers resistance to streptomycin, and wherein the deletion prevents dispersal of the strAB gene to other bacteria.

19. The genetically engineered *Vibrio cholerae* bacterium of claim 1, wherein the bacterium comprises deletion of a floR gene, wherein the floR gene encodes a product that confers resistance to chloramphenicol, and wherein the deletion prevents dispersal of the floR gene to other bacteria.

20. The genetically engineered *Vibrio cholerae* bacterium of claim 1, wherein the deletion in the nucleic acid sequence encoding the cholera toxin subunit A is in a nucleic acid sequence of the core region of a CTXΦ genome that was integrated into the genome of the bacterium, and wherein the deletion protects against toxigenic reversion by preventing chromosomal integration of CTXΦ.

* * * * *